US008092791B2

(12) United States Patent
Federoff et al.

(10) Patent No.: US 8,092,791 B2
(45) Date of Patent: Jan. 10, 2012

(54) METHOD OF PRODUCING HERPES SIMPLEX VIRUS AMPLICONS, RESULTING AMPLICONS, AND THEIR USE

(75) Inventors: Howard J. Federoff, Rochester, NY (US); William J. Bowers, Webster, NY (US)

(73) Assignee: University of Rochester, Rochester, NY (US)

( * ) Notice: Subject to any disclaimer, the term of this patent is extended or adjusted under 35 U.S.C. 154(b) by 2362 days.

(21) Appl. No.: 10/296,551

(22) PCT Filed: May 23, 2001

(86) PCT No.: PCT/US01/16682
§ 371 (c)(1),
(2), (4) Date: Apr. 18, 2003

(87) PCT Pub. No.: WO01/89304
PCT Pub. Date: Nov. 29, 2001

(65) Prior Publication Data
US 2004/0105844 A1 Jun. 3, 2004

Related U.S. Application Data

(60) Provisional application No. 60/206,497, filed on May 23, 2000.

(51) Int. Cl.
*A01N 63/00* (2006.01)
*C12N 15/64* (2006.01)
*C12N 5/00* (2006.01)
*C12N 15/00* (2006.01)

(52) U.S. Cl. .... 424/93.2; 435/456; 435/325; 435/320.1; 435/91.4

(58) Field of Classification Search .................. 514/44; 424/93.2; 435/456, 325, 320.1, 91.4
See application file for complete search history.

(56) References Cited

U.S. PATENT DOCUMENTS

| | | | |
|---|---|---|---|
| 5,501,979 A | 3/1996 | Geller et al. ............... 435/320.1 |
| 5,661,033 A | 8/1997 | Ho et al. | |
| 5,763,217 A * | 6/1998 | Cynader et al. .............. 435/69.1 |
| 5,851,826 A | 12/1998 | Fraefel et al. ................. 435/325 |
| 5,928,913 A | 7/1999 | Efstathiou et al. ......... 435/172.3 |
| 5,965,441 A | 10/1999 | Breakefield et al. .......... 435/456 |
| 5,998,208 A | 12/1999 | Fraefel et al. ................. 435/455 |
| 6,051,428 A | 4/2000 | Fong et al. | |
| 6,344,445 B1 | 2/2002 | Boursnell et al. | |
| 6,635,478 B1 * | 10/2003 | Hippenmeyer et al. ....... 435/325 |
| 2002/0103152 A1 | 8/2002 | Kay et al. | |
| 2004/0047837 A1 | 3/2004 | Fog et al. | |
| 2005/0112764 A1 | 5/2005 | Ivics et al. | |

FOREIGN PATENT DOCUMENTS

| | | |
|---|---|---|
| CN | 1263159 | 8/2000 |
| WO | WO 96/29421 | 9/1996 |
| WO | WO 97/00085 | 1/1997 |
| WO | WO 98/15637 | 4/1998 |
| WO | WO 99/27944 | 6/1999 |
| WO | WO 00/08194 | 2/2000 |
| WO | WO 00/34497 | 6/2000 |
| WO | WO 01/89304 | 11/2001 |
| WO | WO 02/053576 | 7/2002 |
| WO | WO 02/056828 | 7/2002 |
| WO | WO 02/087625 | 11/2002 |

OTHER PUBLICATIONS

Everly et al, Journal of Virology 73(11): 9117-9129, 1999.*
Saeki et al, Human Gene Therapy, 9: 2787-2794, 1998.*
Johnson et al, Journal of Virology, 68(10): 6347-6362, 1994.*
Fraefel et al, Journal of Virology, 70(10): 7190-7197, 1996.*
Sun et al, human Gene Therapy, 10: 2005-2011, 1999.*
Lam et al, (The EMBO Journal, 15(10): 2575-2581, 1996.*
Stavropoulos et al, (Journal of Virology, 72(9): 7137-7143, 1998.*
Whitley et al, (Clinical Infectious Diseases, 26: 541-53, 1998.*
Alexander et al., "Transfer of Contaminants in Adeno-Associated Virus Vector Stocks Can Mimic Transduction and Lead to Artifactual Results"; *Human Gene Therapy*, 8:1911-1920 (1997).
Cunningham et al., "A Cosmid-Based System for Constructing Mutants of Herpes Simplex Virus Type 1"; *Virology*, 197:116-124 (1993).
El-Farrash et al., "Generation and Characterization of a Human Immunodeficiency Virus Type 1 (HIV-1) Mutant Resistant to an HIV-1 Protease Inhibitor"; *Journal of Virology*, 68:233-239 (1994).
Fraefel et al., "Helper Virus-Free Transfer of Herpes Simplex Virus Type 1 Plasmid Vectors into Neural Cells"; *Journal of Virology*, 70:7190-7197 (1996).
Hardwicke et al., "Differential Effects of Nerve Growth Factor and Dexamethasone on Herpes Simplex Virus Type 1 oriL- and oriS-Dependent DNA Replication in PC12 Cells"; *Journal of Virology*, 71:3580-3587 (1997).
Kutubuddin et al., "Eradication of Pre-Established Lymphoma Using Herpes Simplex Virus Amplicon Vectors"; *Blood*, 93:643-654 (1999).
Lam et al, "Herpes simplex virus VP16 rescues viral mRNA from destruction by the virion host shutoff function"; *The EMBO Journal*, 15:2575-2581 (1996).
Liu et al., "Pseudotransduction of Hepatocytes by Using Concentrated Pseudotyped Vesicular Stomatitis Virus G Glycoprotein (VSV-G)-Moloney Murine Leukemia Virus-Derived Retrovirus Vectors: Comparison of VSV-G and Amphotropic Vectors for Hepatic Gene Transfer"; *Journal of Virology*, 70:2497-2502 (1996).

(Continued)

*Primary Examiner* — Thaian N Ton
*Assistant Examiner* — Magdalene Sgagias
(74) *Attorney, Agent, or Firm* — McKeon, Meunier, Carlin & Curfman LLC

(57) ABSTRACT

The present invention relates to a method for producing herpes simplex virus (HSV) amplicon particles which includes co-transfecting a host cell with the following: (i) an amplicon vector comprising an HSV origin of replication, an HSV cleavage/packaging signal, and a heterologous transgene expressible in a patient, (ii) one or more vectors individually or collectively encoding all essential HSV genes but excluding all cleavage/packaging signals, and (iii) a vhs expression vector encoding a virion host shutoff protein; and then isolating HSV amplicon particles produced by the host cell, the HSV amplicon particles including the transgene. Also disclosed are a system and a kit for preparing HSV amplicon particles, HSV amplicon particles prepared according to the process of the present invention, and their use.

28 Claims, 19 Drawing Sheets

OTHER PUBLICATIONS

Rixon et al., "Assembly of enveloped tegument structures (L particles) can occur independently of virion maturation in herpes simplex virus type 1-infected cells"; *Journal of General Virology*, 73:277-284 (1992).

Smibert et al., "Identification and characterization of the virion-induced host shutoff product of herpes simplex virus gene UL41"; *Journal of General Virology*, 73:467-470 (1992).

Stavropoulos et al., "An Enhanced Packaging System for Helper-Dependent Herpes Simplex Virus Vectors"; *Journal of Virology*, 7137-7143 (1998).

Yu et al., "High efficiency in vitro gene transfer into vascular tissues using a pseudotyped retroviral vector without pseudotransduction"; *Gene Therapy*, 6:1876-1883 (1999).

Andreeff et al., "Discrimination of Human Leukemia Subtypes by Flow Cytometric Analysis of Cellular DNA and RNA", Blood, vol. 55, No. 2, pp. 282-293, (Feb. 1980).

Arvanian et al., "Removal of NMDA Receptor Mg+2 Block Extends the Action of NT-3 on Synaptic Transmission in Neonatal Rat Motoneurons", J. Neurophysiol., vol. 86, No. 1, pp. 123-129 (Jul. 2001).

Bogen et al., "Idiotope-Specific T Cell Clones That Recognize Syngeneic Immunoglobulin Fragments in the Context of Class II Molecules", Eur. J. Immunol., vol. 16, pp. 1373-1378, (1986).

Bogen et al., "Processing and Presentation of Idiotypes to MHC-Restricted T Cells", Intern. Rev. Immunol., vol. 10, pp. 337-355 (1993).

Bowers et al., "Expression of VHS and VP16 during HSV-1 helper virus-free amplicon packaging enhances titers," Society for Neuroscience Abstracts, vol. 26, No. 1-2, 2000, pp. Abstract No. 765.10, XP009062401 and 30th Annual Meeting of the Society of Neuroscience; New Orleans, LA, USA, (Nov. 4-9, 2000).

Bowers et al., "Discordance Between Expression and Genome Transfer Titering of HSV Amplicon Vectors: Recommendation for Standardized Enumeration", Molecular Therapy, vol. 1, No. 3, pp. 294-299 (Mar. 2000).

Bowers et al., "Neurotrophin-3 transduction attenuates cisplatin spiral ganglion neuron ototoxicity in the cochlea," Molecular Therapy, vol. 6, No. 1, pp. 12-18, Jul. 2002.

Caligaris-Cappio et al., "B-Cell Chronic Lymphocytic Leukemia: a Bird of a Different Feather", Journ. of Clinical Oncology, vol. 17, No. 1, pp. 399-408, (Jan. 1999).

Cantwell, et al., "Adenovirus Vector Infection of Chronic Lymphocytic Leukemia B Cells", Blood, vol. 88, No. 12, pp. 4676-4683, (Dec. 15, 1996).

Cardoso et al., "Pre-B Acute Lymphoblastic Leukemia Cells May Induce T-Cell Anergy to Alloantigen", Blood, vol. 88, No. 1, pp. 41-48, (Jul. 1, 1996).

Collins, M., "Retroviral Vectors for Cancer Gene Therapy", Springer-Verlag Berlin Heidelberg New York, ISSN 0947-6075 an ISBN 3-540-67298-2, pp. 100-105.

Croce et al., "The Use of Carbohydrate Antigens for the Preparation of Vaccines for Therapy in Breast Cancer", Drugs of Today, vol. 38, No. 11 pp. 759-768 (2002).

De Felipe et al., "Integrating Retoviral Cassette Extends Gene Delivery of HSV-1 Expression Vectors to Dividing Cells", Biotechniques, vol. 31, No. 2, pp. 394-402 (Aug. 2001).

Döhner et al., "Chromopsome Aberrations in B-Cell Chronic Lymphocytic Leukemia: Reassessment Based on Molecular Cytogenetic Analysis", J. Mol. Med., 77:266-281 (1999).

Diehl et al., "CD40 Activation in vivo Overcomes Peptide-Induced Peripheral Cytotoxic T-Lymphocyte Tolerance and Augments Anti-Tumor Vaccine Efficacy", Nature Medicine, vol. 5, No. 7, pp. 774-779 (Jul. 1999).

Everly, Jr., et al., "Mutational Analysis of the Virion Host shutoff Gene (LUL41) of Herpes Simplex Virus (HSV): Characterization of HSV Type 1 (HSV-1) HSV-2 Chimeras", Journal of Virology, vol. 71, No. 10, pp. 7157-7166, (Oct. 1997).

Everly, Jr., et al., "Site-Directed Mutagenesis of the Virion Host Shutoff Gene (UL41) of Herpes Simplex Virus (HSV): Analysis of Functional Differences between HSV Type 1 (HSV-1) and HSV-2 Alleles", Journal of Virology, vol. 73, No. 11, pp. 9117-9129, (Nov. 1999).

Fink et al., "Engineering herpes simplex virus vectors for gene transfer to neurons," Nature Medicine, vol. 3, No. 3, pp. 357-359, 1997.

Frenkel et al., "Minereview: the Herpes Simplex Virus Amplicon—A Versatile Defective Virus Vector", Gene Therapy, vol. 1, Suppl. 1, pp. S40-S46, (1994).

Frenkel et al., "The Herpes Simplex Virus Amplicon—A Novel Animal Virus Cloning Vector", Eukaryotic Viral Vectors, pp. 205-209, by Cold Spring Harbor Laboratory (1982).

Geller et al., "A Defective HSV-1 Vector Expresses, *Escherichia coli*β-Galactosidase in Cultured Peripheral Neurons", Science, vol. 241, pp. 1667-1169, (Sep. 23, 1988).

Geller, "A New Method to Propagate Defective HSV-1 Vectors", Nucleic Acids Research, vol. 16, No. 12, pp. 5690, (1988).

Geller et al., "An Efficient Deletion Mutant Packaging System for Defective Herpes Simplex Virus Vectors: Potential Applications to Human Gene Therapy and Neuronal Physiology", Proc. Natl. Acad. Sci., USA, vol. 87, No. 22, pp. 8950-8954, (Nov. 1990).

Geller et al., "Helper Virus-Free Herpes Simplex Virus-1 Plasmid Vectors for Gene Therapy of Parkinson's Disease and Other Neurological Disorders"; *Experimental Neurology*, vol. 144, No. 1, pp. 98-102 (1997).

Geschwind et al., "Transfer of the Never Growth Factor Gene into Cell Lines and Cultured Neurons Using a Defective Herpes Simplex Virus Vector. Transfer of the NGF Gene into Cells by a HSV-1 Vector", Molecular Brain Research, vol. 24, pp. 327-335, (1994).

Crewal et al., "The Role of CD40 Ligand in Costimulation and T-Cell Activation", Immunological Reviews, No. 153, pp. 86-105, (1996).

Gorantla et al., "Human dendritic cells transduced with herpex simplex virus amplicons encoding human immunodeficiency virus type 1 (HIV-1) gp120 elicit adaptive immune responses from human cells engrafted into NOD/SCID mice and confer partial protection against HIV-1 challenge," J. Virol., vol. 79, No. 4, pp. 2124-2132, Feb. 2005.

Gruss et al., "CD40/CD40 Ligand Interactions in Normal, Reactive and Malignant Lympho-Hematopoietic Tissues", Leukemia and Lymphoma, vol. 24, No. 5/6, pp. 393-422 (1997).

Haase et al., "Gene Therapy of Murine Motor Neuron Disease Using Adenorival Vectors for Neurotrophic Factors", Nat. Med., vol. 3, No. 4, pp. 429-436 (Apr. 1997).

Harris et al., "Keyhole Limpet Hemocyanin: Molecular Structure of a Potent Marine Immunoactivator", Euro. Urol., vol. 37 (Suppl. 3), pp. 24-33 (2000).

Hirano, et al., "Expression of Costimulatory Molecules in Human Leukemias", Leukemia, vol. 10, No. 7, pp. 1168-1176, (Mar. 21, 1996).

Hitt et al., "Human Adenovirus Vectors for Gene Transfer into Mammalian Cells", Gene Therapy, Advances in Pharmacology, vol. 40, pp. 137-206, (1997).

Hocknell et al., "Expression of human immunodeficiency virus type 1 gp120 from herpes simplex virus type 1-derived amplicons results in potent specific, and durable cellular and humoral immune responses," J. Virol., vol. 76, No. 11, pp. 5565-5580, Jun. 2002.

Howard et al., "Genetic Manipulation of Primitive Leukemic and Normal Hematopoietic Cells Using a Novel Method of Adenovirus-Mediated Gene Transfer", Leukemia, vol. 13, No. 10, pp. 1608-1616, (Oct. 1999).

Huang et al., "Efficient Adenovirus-Mediated Gene Transduction of Normal and Leukemic Hematopoietic Cells", Gene Therapy, vol. 4, No. 10, pp. 1093-1099 (Oct. 1997).

Karr et al., "The *Virion Host Shutoff* Function of Herpes Simplex Virus Degrades the 5' End of a Target mRNA before the 3' End", Virology, vol. 264, No. 1, pp. 195-204, (1999).

Khanna et al., "Cutting Edge: Engagement of CD40 Antigen with Soluble CD40 Ligand Up-Regulates Peptide Transporter Expression and Restores Endogenous Processing Function in Burkitt's Lymphoma Cells", The Journ. of Immunology, vol. 159, No. 12, pp. 5783-5785 (Dec. 15, 1997).

Kochanek, "High-Capacity Adenoviral Vectors for Gene Transfer and Somatic Gene Therapy", Human Gene Therapy, vol. 10, No. 15, pp. 2451-2459, (Oct. 10, 1999).

Kwak et al., "Induction of Immune Responses in Patients with B-Cell Lymphoma Against the Surface-Immunoglobulin Idiotype Expressed by Their Tumors", The New England Journal of Medicine, vol. 327, No. 17, pp. 1209-1215, (Oct. 22, 1992).
Kwong et al., "The Herpes Simplex Virus Virion Host Shutoff Function", vol. 63, No. 11, pp. 4834-4839, (Nov. 1989).
Lanzavecchia,"Licence to Kill", Nature, vol. 393, pp. 413-414, (Jun. 4, 1998).
Lieb et al, "Gene Delivery to Neurons: Is Herpes Simplex Virus the Right tTool for the Job?", BioEssays, vol. 15, No. 8 pp. 547-554, (Aug. 1993).
Lillycrop et al., "The Octamer-Binding Protein Oct-2 Represses HSV Immediate-Early Genes in Cell Lines Derived from Latently Infectble Sensory Neurons", Neuron, vol. 7, No. 3, pp. 381-390,(Sep. 1991).
Lu et al., "Herpes Simplex Virus Type 1 Amplicon Vectors with Glucocorticoid-Inducible Gene Expression", Human Gene Therapy, vol. 6, No. 4, pp. 419-428, (Apr. 1995).
Mader et al., "A Steroid-Inducible Promotr for the Controlled Overexpression of Cloned Genes in Eukaryotic Cells", Proc. Natl. Acad. Sci. USA, vol. 90. pp. 5603-5607, (Jun. 1993).
Maguire-Zeiss Ka et al., "HSV Vector-Mediated Gene Delivery to the Central Nervous System", Current Opinion Molecular Therapy, vol. 3, No. 5, pp. 482-490 (Oct. 2001).
Marsh D.R. et al., Herpes Simplex Viral and Amplicon Vector-Mediated Gene Transfer into Glia and Neurons in Organotypic Spinal Cord and Dorsal Root Ganglion Cultures. Molec. Therap. May 2000, vol. 1. No. 5, pp. 464-478.
Martuza et al, "Experimental Therapy of Human Glioma by Means fo a Geneticlaly Engineered Virus Mutant", Science, vol. 252, pp. 854-856 (May 10, 1991).
Matzinger, "The JAM Test a Simple assay for DNA Fragmentation and Cell Death", Journ. of Immunological Methods, vol. 145, pp. 185-192 (1991).
McFarlane et al., "Hexamethylene Bisacetamide Stimulates Herpes Simplex Virus Immediate early Gene Expression in the Absence of Trans-Induction by Vmw65", Journal of General Virology, vol. 73, pp. 285-292, (1992).
Mellerick et al., "Physical State of the Latent Herpes Simplex Virus Genome in a Mouse Model System: Evidence Suggesting and Episomal State", Virology, vol. 158, pp. 265-275, (1987).
O'Hare et al., "Herpes Simplex Virus Regulatory Elements and the Immunoglobulin Octamer Domain Bind a Common kfactor and are both Targets for Virion Transactivation", Cell, vol. 52, pp. 435-445, (Feb. 12, 1988).
O'Hare, "The Virion Transactivator of Herpes Simplex Virus", Virology, vol. 4, pp. 145-155, (1993).
Olschowka et al., "Helper-free HSV-1 amplicons elicit a markedly less robust innate immune response in the CNS," Molecular Therapy; vol. 7, No. 2, pp. 218-227, Feb. 2003.
Palella et al., "Herpes Simplex Virsu-Mediated Human Hypoxanthine-Guanine Phosphoribosyltransferase Gene Transfer into Neuronal Cells", Molecular and Cellular Biology, vol. 8 No. 1, pp. 457-460 (Jan. 1988).
Paterson et al., "A Prominent Serine-Rich Region in Vmw175, the Major Transcriptional Regulator protein of Herpes Simplex Virus Type 1, is not Essential for Virus Growth in Tissue Culture", Journal of General Virology, vol. 71, pp. 1775-1783 (1990).
Post et al., "Regulation of a α Genes of Herpes Simplex Virus: Expression of Chimeric Genes Produced by Fusion of Thymidine Kinase with a α Gene Promoters", Cell, vol. 24, pp. 555-565, (May 1981).
Preston, et al., "A Complex Formed between Cell Components and an HSV Structural Polypeptide Binds to a Viral Immediate Early Gene Regulatory DNA Sequence", Cell, vol. 52, pp. 425-434, (Feb. 12, 1988).
Read et al., "Herpes Simplex Virus Mutants Defective in the Virion-Associated Shutoff of Host Polypeptide Synthesis and Exhibiting Abnormal Synthesis of α (Immedate Early) Viral Polypeptides", Journal of Virology, vol. 46, No. 2, pp. 498-512 (May 1983).
Roizman, "HSV Gene Functions: What Have we Learned that could be Generally Applicable to its Near and Distant Cousins?", Acta Virologia, vol. 43, pp. 75-80, (1999).
Saeki et al., "Herpes Simplex Virus Type 1 DNA Amplified as Bacterial Artificial Chromosome in *Escherichia coli*: Rescue of Replication-Competent Virus Progeny and Packaging of Amplicon Vectors", Human Gene Therapy, vol. 9, pp. 2787-2794 (Dec. 10, 1998).
Saeki et al., "Improved helper virus-free packaging system for HSV amplicon vectors using an ICP27-deleted, oversized HSV-1 DNA in a bacterial artificial chromosome," Molecular Therapy, vol. 3, No. 4, pp. 591-601, Apr. 2001.
Schmelter et al., "Identification and Characterization of a Small Modular domain in the Herpes Simplex Virus Host Shutoff Protein Sufficient for Interaction with VP16", Journal of Virology, vol. 7, No. 4, pp. 2124-2131, (Apr. 1996).
Sena-Estaves et al., "HSV-1 Amplicon Vectors—Simplicity and Versatility", Molecular Therapy, vol. 2, No. 1, pp. 9-15 (Jul. 2000).
Smibert et al., "Herpes Simplex Virus VP16 Forms a Complex with the Virion Host Shutoff Protein vhs", Journal of Virology, vol. 68, No. 4, pp. 2339-2346 (Apr. 1994).
Sotomayor et al., "Conversion of Tumor-Specific CD4+T-Cell Tolerance to T-Cell Priming through in vivo ligation of CD40", Nature Medicine, vol. 5, No. 7, pp. 780-784 (Jul. 1999).
Spaete et al., "The Herpes Simplex Virus Amplicon: A New Eucaryotic Defective-Virus Cloning-Amplifying Vector", Cell, vol. 30, pp. 295-304 (Aug. 1982).
Spector et al., "Replication-defective Herpesvirus Amplicon Vectors and Their Use for Gene Transfer", Cells: a Laboratory Manual, vol. 2: Light Microscopy and Cell Structure, pp. 91.1-91.10 (1997).
Stern et al., "The Oct-1 Homoeodomain Directs Formation of a Multiprotein-DNA Complex with the HSV Transactivator VP16", Nature, vol. 341, pp. 624-630 (Oct. 19, 1989).
Sun et al., "Improved Titers for Helper Virus-Free Herpes Simplex Virus Type 1 Plasmid Vectors by Optimization of the Packaging Protocol and Addition of Noninfectious Herpes Simplex Virus-Related Particles (Previral DNA Replication Enveloped Particles) to the Packaging Procedure", Human Gene Therapy, vol. 10, pp. 2005-2011 (Aug. 10, 1999).
Tolba et al., "Development of Herpes Simplex Virus-1 Amplicon-Based Immunotherapy for Chronic Lymphocytic Leukemia", Blood, vol. 98, No. 2, pp. 287-295 (Jul. 15, 2001).
Tolba et al., "Herpes simplex virus (HSV) amplicon-mediated codelivery of secondary lymphoid tissue chemokine and CD40L results in augmented antitumor activity," Cancer Research, vol. 62, No. 22, pp. 6545-6551, Nov. 15, 2002.
Trojan et al., "Immunoglobulin Framework-Derived Peptides Function as Cytotoxic T-Cell Epitopes Commonly Expressed in B-Cell Malignancies", Nature Medicine, vol. 6, No. 6, pp. 667-672 (Jun. 2000).
Van Kooten et al., "Functions of CD40 on B Cells, Dendritic Cells and other Cells", Immunology, vol. 9, No. 3, pp. 330-337 (Jun. 1997).
Vile et al., "Retroviral Vectors: From Laboratory Tools to Molecular Medicines", Molecular Biotechnology, vol. 5, pp. 139-158 (1996).
Wang et al., "HSV-1 amplicon vectors are a highly efficient gene delivery system for skeletal muscle myoblasts and myotubules," Am. J. Physiol., 278(3):C619-26, Mar. 2000.
Wang et al., "Cellular immune responses to helper-free HSV-1 amplicon particles encoding HSV-1 gp120 are enhanced by DNA priming," Vaccine, vol. 21, No. 19-20, pp. 2288-2297, Jun. 2, 2003.
Wigdahl et al., "Herpes Simplex Virus Latency in Isolated Human Neurons", Proc. Natl. Acad. Sci. USA, vol. 81, No. 19, pp. 6217-6221, (Oct. 1984).
Wilson et al., "The VP16 Accessory Protein HCF Is a Family of Polypeptides Processed from a Large Precursor Protein", Cell, vol. 74, pp. 115-125 (Jul. 16, 1993).
Xiao et al., "A Cellular Factor Binds to the Herpes Simplex Virus Type 1 Transactivator Vmw65 and Is Required for Vmw65-Dependent Protein-DNA Complex Assembly with Oct. 1", Molecular and Cellular Biology vol. 10, No. 9, pp. 4974-4977 (Sep. 1990).
Zhang et al., "An efficient selection system for packaging herpes simplex virus amplicons"; *Journal of General Virology*, vol. 79, Part 1, pp. 125-131 (1998).
Bowers, W.J. et al., "Expression of vhs and VP16 during HSV-1 helper virus-free amplicon packaging enhances titers", Gene Therapy, vol. 8, No. 2, pp. 111-120, Jan. 2001.
Bowers, W.J. et al., "Development of integrating HSV-1 amplicon vectors for CNS gene transfer", Society for Neuroscience Abstract, vol. 2002, Abstract No. 387.13, Nov. 2, 2002.

Chen, Xiaowei et al., "HSV amplicon-mediated neurotrophin-3 expression protects murine spiral ganglion neurons from cisplatin-induced damage", Molecular Therapy, vol. 3, No. 6, pp. 958-963, Jun. 6, 2001.

Chow et al., "Improvement of Hepatitis B Virus DNA Vaccines by Plasmids Coexpressing Hepatitis B Surface Antigen and Interleukin-2"; Journal of Virology, 71: 169-179, 1997.

Halterman, M.W. et al., "Restricted replication using VP16 in HSV-1 mutants produces amplicon vectors with reduced toxicity", Society for Neuroscience Abstracts, vol. 26, No. 1-2, Abstract No. 232-13, Nov. 4, 2000.

Johnson, Paul et al., "Improved cell survival by the reduction of immediate-early gene expression in replication-defective mutants of herpes simplex virus type 1 but not by mutation of the virion host shutoff function", Journal of Virology, vol. 68, No. 10, pp. 6347-6362, Oct. 1994.

Karpoff et al. "Prevention of Hepatic Tumor Metastases in Rats with Herpes Viral Vaccines and Gamma Interferon", Journal of Clinical Investigation, 99: 799-804, 1997.

Holscher et al., "Overexpression of nonconvertible $PrP^c$ $\Delta$114-121 in scrapie-infected mouse neuroblastoma cells leads to trans-dominant inhibition of wild type $PrP^{Sc}$ accumulation," J. Virol. 72(2):1153-9 (1998).

Yant et al., "Somatic integration and long term transgene expression in normal and haemophilia mice using a DNA transposon system," Nat. Gen. 25:35-41 (2000).

Yant et al Nature Genetics, 2000, 25, 35-41.

Bowers et al Gene Therapy, 2001, 8, 111-120.

Holscher et al J Virol. Feb. 1998:72(2):1153-9.

Gilboa et al., "Immunotherapy of cancer with dendritic-cell-based vaccines" *Cancer Immunol. Immunother.* 46:82-87 (1998).

Herrlinger et al., "Helper virus-free herpes simplex virus type 1 amplicon vectors for granulocyte-machrophage colony-stimulating factor-enhanced vaccination therapy for experimental glioma" *Human Gene Therapy* 11:1429-1438 (2000).

Morse et al., "Optimization of the sequence of antigen loading and CD40-ligand-induced maturation of dendritic cells" *Cancer Research* 58:2965-2968 (1998).

Guo et al., "Protein tolerance to random amino acid change," Proc. Natl. Acad. Sci. USA 101:9205-10 (2004).

Lesk and Whisstock, "Prediction of protein function from protein sequence and structure," Abstract: 27-28.

Read et al., "Isolation of a Herpes Simplex Virus Type 1 mutant with a deletion in the virion host shutoff gene and identification of multiple forms of the *vhs* (UL41) polypeptide," J. Virol. 67:7149-7160 (1993).

Bowers et al., "Neuronal precursor-restricted transduction via in vitro CNS gene delivery of a novel bipartite HSV amplicon/transposase hybrid vector," Mol. Ther. 13:580-8 (2006).

Plasterak et al., "Resident aliens: the Tc1/mariner superfamily of transposable elements," Trends in Genetics 15:326-32 (1999).

* cited by examiner

```
CGTCGACGACCACAGAGAAGGTGCGATGGGTATTTTCCCCGTACACCGTCTTGGCGTTGG
CGGCCGCCTGGCCCGCCTTGGTGAGCGCGTTGGACAGGATCTGGACCTGGGTGCTGGTGC
TGGACGACACGCCCTCCTCGCGGGCAGCAAAGGTGACGCAGGTACTCGTGGTGAACACGG
AAAATTTGCCGTTAACCCCGAGCTCGAACGTGGTGGGCGTGGCACTATCGGCCCCGGTCG
CGTTAAGGACCTTGGTGAGCTGCGGCCTCGTCAGGCGCAACTGAACGTCGGGGGTTCCCT     300
GGGGAACCAGCACCACAAAGCTCGTCAGTTCGCGCTTCATCAGCGTCTCGCTGGCTAGCT
CAACGGCCTCGCCGTCGGACGTCGTCGTCCATATGCGCTGAACCAGCGTGCGAAACGGGG
CCTGGCCCGTGATCGCCAACTCCACCCGACGTAGGTCCGGGTACTGGTTGGCGCGAAACA
CGCTCAGGAGGGAGCGCTTCTGGTCCACGAGAGACAGGAACGCCGCCGTGGGTCCGCGCC
AGCGATACCGACTGAATTGCGAGTGTTCCAGGGGCAGGAACACCTGCTCCCCAAAGATCG     600
TGTTATGGATAAGGATGCCCCGGTCGCCCATAACCAGAAGCGAGTCCAGAAGGCTCGTGC
GCAGCGGGGCAAACGCCTGTAGGATTCCATTAAGTTCGGCGCCCTGCAGGACCACCTGGC
AGGGCGCCCCTCCTCCGGCTGCCCGAGGGACGCGTCCGACGCGTCCTCCACGGGGGAGG
CGGGGGCCACACCGCCAGGGGAATCCGTCATCCCAACGCGGGCTGGGAACACCCCACAGT
GACGAGGTGGGCTTCGGTGGTGAGGGCAGCCGGGCCGGGGTCTCGGGTGCGGGACGCGGA     900
GGGGGCGTATGCCGCTGCGAGGGTGGGGTTTTGATGGCAGCCAGGGGACCCAAGCAACCG
GACCGTCGCTCACCGAGCCAGAAACTACGGCAGGCCCGCCGCGCTAGCCTGATTAAATAC
GCCCCCAGCTCGTTAGGCCACACCCTTTTGGAAGAGGCAATGAGCGGGGGGAAGGTTGGC
CCGCACCGGCGCATGCAGGGTGCTGCACCAATCCGCGTGGAGTTGGGCCATCGAAATTAT
AAAGAGCGTCCCCTAACGGATTATTGTCCTCTTGTGTCGGTGTTGTTGTCTGGGTCACCA   1200
TACACAGAGAGACAGGCTCGGGTGTCCCGGACCGTCGCACCAACCACGCCTTAGTTAGGC
CGATCCGCAGTTACAATTGACCTGACATGGGTTTGTTCGGGATGATGAAGTTTGCCCACA
CACACCATCTGGTCAAGCGCCGGGGCCTTGGGGCCCCGGCCGGGTACTTCACCCCCATTG
CCGTGGACCTGTGGAACGTCATGTACACGTTGGTGGTCAAATATCAGCGCCGATACCCCA
GTTACGACCGCGAGGCCATTACGCTACACTGCCTCTGTCGCTTATTAAAGGTGTTTACCC   1500
AAAAGTCCCTTTTTCCCCATCTTCGTTACCGATCGCGGGGTCAATTGTATGGAGCCGGTTG
TGTTTGGAGCCAAGGCCATCCTGGCCCGCACGACGGCCCAGTGCCGGACGGACGAGGAGG
CCAGTGACGTGGACGCCTCTCCACCGCCTTCCCCCATCACCGACTCCAGACCCAGCTCTG
CCTTTTCCAACATGCGCCGGCGCGGCACCTCTCTGGCCTCGGGGACCCGGGGGACGGCCG
GGTCCGGAGCCGCGCTGCCGTCCGCCGCGCCCTCGAAGCCGGCCCTGCGTCTGGCGCATC   1800
TGTTCTGTATTCGCGTTCTCCGGGCCCTGGGGTACGCCTACATTAACTCGGGTCAGCTGG
AGGCGGACGATGCCTGCGCCAACCTCTATCACACCAACACGGTCGCGTACGTGTACACCA
CGGACACTGACCTCCTGTTGATGGGCTGTGATATTGTGTTGGATATTAGCGCCTGCTACA
TTCCCACGATCAACTGTCGCGATATACTAAAGTACTTTAAGATGAGCTACCCCCAGTTCC
TGGCCCTCTTTGTCCGCTGCCACACCGACCTCCATCCCAATAACACCTACGCCTCCGTGG   2100
AGGATGTGCTGCGCGAATGTCACTGGACCCCCCGAGTCGCTCTCAGACCCGGCGGGCCA
TCCGCCGGGAACACACCAGCTCGCGCTCCACGGAAACCAGGCCCCCTCTGCCGCCGGCCG
CCGGCGGCACCGAGACGCGCGTCTCGTGGACCGAAATTCTAACCCAACAGATCGCCGGCG
GATACGAAGACGACGAGGACCTCCCCCTGGATCCCCGGGACGTTACCGGGGGCCACCCCG
GCCCCAGGTCGTCCTCCTCGGAGATACTCACCCCGCCCGAGCTCGTCCAGGTCCCGAACG   2400
CGCAGCTGCTGGAAGAGCACCGCAGTTATGTGGCCAACCCGCGACGCCACGTCATCCACG
ACGCCCCAGAGTCCCTGGACTGGCTCCCCGATCCCATGACCATCACCGAGCTGGTGGAAC
ACCGCTACATTAAGTACGTCATATCGCTTATCGGCCCCAAGGAGCGGGGCCGTGGACTC
TTCTGAAACGCCTGCCTATCTACCAGGACATCCGCGACGAAAACCTGGCGCGATCTATCG
TGACCCGGCATATCACGGCCCCTGATATCGCCGACAGGTTTCTGGAGCAGTTGCGGACCC   2700
```

*FIG. 4B*

```
AGGCCCCCCCACCCGCGTTCTACAAGGACGTCCTGGCCAAATTCTGGGACGAGTAGCCCA
AACGTCAGACGAGCGCGCTTGTCCCCGAACAAACGACCCACCAATAAAATTATGGTATCC
TATGCCCGCAGAATCTGGACGGACCTGGTTACTGCTTTTTGCGCCGCCTTTTATCCTCTC
CCACCCCCGCGTCCCTGACAAGAATCACAATGAGACCCAAAGTTTGGTTCAGAGGTTTAT
TATGGGCAAACACGGGTAGAAGCGCGCCGCGACACTCACAGATCGTTGACGACCGCCCG   3000
GCGTAGGAGGTGCTGCGACACTCGAAAAAATTGGTGTGTTTGTCGGTGGACATGAGGCTC
AGCGGAAAGCTGGCGTCGGGGGGTGGGCGGAAAACAGTGGCTTCATGTGGATAAGGCCC
AACAGGCGATCCGCGCTGAATCGCACGTAGTTTTCGATGGCCGCCAGCGCCGCCGGGCTC
AGGATATGGCTGTCCGTCGGCGCCTGGGATCGGATAAATCCGATCTCGATCTCGACCGCC
TGGCGGAACAGCCCGTACACGCGGTCGGGCGGGGGCTTGGCGTGCCCGCCGAGGTAGTTG   3300
TTGTAGATGTAACACGAGGCCGTCGTGTGCACGGCCTCGTCCCGGCTGATGAGGTCGTTT
GACTGGCAGGTGACCCGCAGAAGGTTGTTGGTGCGAAGGTAGGCGATGGCGGCAAACGAG
GCGGCAAAAAGATGCCCTCGATGAGGATCATGAGAATGAACTTTTCCGGAACGGAGGCG
CATTCCCGCACCCGCGCTTCCAACCAGTCCACCTTGGCGCGGATGGCCGGGTGGTTGATG
GTACCGGCCACGTACTCGCGGCGCGCCTGGTCGTTGTTGTGGAAAAGCACCAGCTGGATG   3600
ATGTTGTACACGCGCGAGTGTACGACTTCGATGCATTCCTGCTCCACGTAGTAGTGGAGA
ATGTCCTTCTGCTCAAACAGGCCGGAGAGGCCGCCCAGGTTTTCCGTAACCAGGTCGTCG
GCGGCCGACAGGAAAGCGAAGAGGAAGCGGTAAAAGCTGAGCTCGCCCTCGGAAAGCTTG
GAGACGTCCTCCTCGTCCCCCACGAAAACAAGCTCGGTTTCCAGCCAGCGGTTAAGGATG
CTGAGGGAGCGCAGGTGGTTAATGTCGGGACACTGGGAGGTGTAGAAGTACCTCTCGGGG   3900
TCGGGGCACTTTGGAATCTGGATCGCCAGGTCCGCCGTCGCGCTCTGGTCCGTAAGGGCC
GTCAGAGCGGGGGAGAGGGCTGGGGCCGCGGAATCCATGGCAGCAGGGGAGAGCGTGGGA
CGGCGACGACAGTGGCGGCGGGCCTGGCGCGGAGGGGGTTTGTCGGTCACAGCGCGCAGC
TCATGCAGACAATGTTGTCGTCGCCGCCAAAGACCCCGCTGTTGGTCGCCTTGCGAACCT
TGCAGTAGTACATCCCTGTTTTTAGTCCGCGCTTATATGCGTGGACCAGAAGGCGGACCA   4200
GGGTGGAGGCTGGGAGGGTCCCGTCCGCCTTCTCCGTGACATACAGGGTCATGGATTGGC
TATGGT
```

*FIG. 4C*

METHOD OF PRODUCING HERPES SIMPLEX VIRUS AMPLICONS, RESULTING AMPLICONS, AND THEIR USE

This application claims benefit of U.S. Provisional Application Serial No. 60/206,497, filed May 23, 2000, which is hereby incorporated by reference in its entirety.

The present invention was made, at least in part, with support from the National Institutes of Health Grant Nos. R01-NS36420 and R21-DK53160, and AFAR Research Grant. The U.S. government may have certain rights in this invention.

FIELD OF THE INVENTION

The present invention relates to an improved method for producing herpes simplex virus ("HSV") amplicons, the resulting HSV amplicons, and their use in gene therapy.

BACKGROUND OF THE INVENTION

The ability to deliver genes to the nervous system, and to manipulate their expression, may make possible the treatment of numerous neurological disorders. Unfortunately, gene transfer into the central nervous system ("CNS") presents several problems including the relative inaccessibility of the brain and the blood-brain-barrier, and that neurons of the postnatal brain are post-mitotic. The standard approach for somatic cell gene transfer, i.e., that of retroviral vectors, is not feasible for the brain, as retrovirally mediated gene transfer requires at least one cell division for integration and expression. A number of new vectors and non-viral methods have therefore been used for gene transfer in the CNS. Although the first studies of gene transfer in the CNS used an ex vivo approach, i.e., the transplantation of retrovirally-transduced cells, more recently several groups have also used an in vivo approach.

The in vivo approach was initially largely based on the use of the neurotropic herpes simplex virus ("HSV"), however, HSV vectors present several problems, including instability of expression and reversion to wild-type.

The genome of HSV-1 is about 150 kb of linear, double-stranded DNA, featuring about 70 genes. Many viral genes may be deleted without the virus losing its ability to propagate. The "immediately early" ("IE") genes are transcribed first. They encode trans-acting factors which regulate expression of other viral genes. The "early" ("E") gene products participate in replication of viral DNA. The late genes encode the structural components of the virion as well as proteins which turn on transcription of the IE and E genes or disrupt host cell protein translation.

After viral entry into the nucleus of a neuron, the viral DNA can enter a state of latency, existing as circular episomal elements in the nucleus. While in the latent state, its transcriptional activity is reduced. If the virus does not enter latency, or if it is reactivated, the virus produces numerous infectious particles, which leads rapidly to the death of the neuron. HSV-1 is efficiently transported between synaptically connected neurons, and hence can spread rapidly through the nervous system.

Two types of HSV vectors previously have been utilized for gene transfer into the nervous system. Recombinant HSV vectors involve the removal of an immediate-early gene within the HSV genome (ICP4, for example), and replacement with the gene of interest. Although removal of this gene prevents replication and spread of the virus within cells which do not complement for the missing HSV protein, all of the other genes within the HSV genome are retained. Replication and spread of such viruses in vivo is thereby limited, but expression of viral genes within infected cells continues. Several of the viral expression products may be directly toxic to the recipient cell, and expression of viral genes within cells expressing MHC antigens can induce harmful immune reactions. In addition, nearly all adults harbor latent herpes simplex viruses within neurons, and the presence of recombinant HSV vectors could result in recombinations which can produce an actively replicating wild-type virus. Alternatively, expression of viral genes from the recombinant vector within a cell harboring a latent virus might promote reactivation of the virus. Finally, long-term expression from the recombinant HSV vector in the CNS has not been reliably demonstrated. It is likely that, except for conditions in which latency is induced, the inability of HSV genomes to integrate within host DNA results in susceptibility to degradation of the vector DNA.

In an attempt to circumvent the difficulties inherent in the recombinant HSV vector, defective HSV vectors were employed as gene transfer vehicles within the nervous system. The defective HSV vector is a plasmid-based system, whereby a plasmid vector (termed an amplicon) is generated which contains the gene of interest and two cis-acting HSV recognition signals. These are the origin of DNA replication and the cleavage packaging signal. These sequences encode no HSV gene products. In the presence of HSV proteins provided by a helper virus, the amplicon is replicated and packaged into an HSV coat. This vector therefore expresses no viral gene products within the recipient cell, and recombination with or reactivation of latent viruses by the vector is limited due to the minimal amount of HSV DNA sequence present within the defective HSV vector genome. The major limitation of this system, however, is the inability to eliminate residual helper virus from the defective vector stock. The helper virus is often a mutant HSV which, like the recombinant vectors, can only replicate under permissive conditions in tissue culture. The continued presence of mutant helper HSV within the defective vector stock, however, presents problems which are similar to those enumerated above in regard to the recombinant HSV vector. This would therefore serve to limit the usefulness of the defective HSV vector for human applications.

While HSV vectors of reduced toxicity and replication ability have been suggested, they can still mutate to a more dangerous form, or activate a latent virus, and, since the HSV does not integrate, achieving long-term expression would be difficult.

To avoid the difficulties raised with the use of helper viruses, newer methods of packaging have been developed that result in "helper virus-free" amplicon stocks (Fraefel et al., "Helper virus-free transfer of herpes simplex virus type 1 plasmid vectors into neural cells," *J. Virol.*, 70:7190-7197 (1996); Stavropoulos and Strathdee, "An enhanced packaging system for helper-dependent herpes simplex virus vectors," *J. Virol.*, 72:7137-43 (1998)). Stocks produced by these means, however, are typically of low titer (approximately $10^5$ expression units/ml or less), allowing for only modest in vitro experimentation. Such low titers discourage investigators from performing the large animal studies required to develop and assess amplicon-directed therapies in mammals, including humans.

The present invention is directed to overcoming these deficiencies in the art.

SUMMARY OF THE INVENTION

A first aspect of the present invention relates to a method for producing herpes simplex virus ("HSV") amplicon particles, which includes co-transfecting a host cell with the following: (i) an amplicon vector comprising an HSV origin of replication, an HSV cleavage/packaging signal, and a heterologous transgene expressible in a patient, (ii) one or more vectors individually or collectively encoding all essential HSV genes but excluding all cleavage/packaging signals, and (iii) a vhs expression vector encoding a virion host shutoff protein; and then isolating HSV amplicon particles produced by the host cell, the HSV amplicon particles including the transgene.

A second aspect of the present invention relates to HSV amplicon particles produced according to the method of the present invention.

A third aspect of the present invention relates to a system for preparing HSV amplicon particles which includes: an amplicon vector comprising an HSV origin of replication, an HSV cleavage/packaging signal, and a transgene insertion site; one or more vectors individually or collectively encoding all essential HSV genes but excluding all cleavage/packaging signals; and a vhs expression vector encoding a virion host shutoff protein; wherein upon introduction of the system into a host cell, the host cell produces herpes simplex virus amplicon particles.

A fourth aspect of the present invention relates to a kit for preparing HSV amplicon particles which includes: an amplicon vector comprising an HSV origin of replication, an HSV cleavage/packaging signal, and a transgene insertion site; one or more vectors individually or collectively encoding all essential HSV genes but excluding all cleavage/packaging signals; a vhs expression vector encoding an virion host shutoff protein; a population of host cells susceptible to transfection by the amplicon vector, the vhs expression vector, and the one or more vectors; and directions for transfecting the host cells under conditions to produce HSV amplicon particles.

A fifth aspect of the present invention relates to a method of treating a neurological disease or disorder which includes providing HSV amplicon particles of the present invention that include a transgene encoding a therapeutic transgene product and exposing neural or pre-neural cells of a patient to the HSV amplicon particles under conditions effective for infective transformation of the neural or pre-neural cells, wherein the therapeutic transgene product is expressed in vivo in the neural or pre-neural cells, thereby treating the neurological disease or disorder.

A sixth aspect of the present invention relates to a method of inhibiting development of a neurological disease or disorder which includes providing HSV amplicon particles of the present invention that include a transgene encoding a therapeutic transgene product and exposing neural or pre-neural cells of a patient susceptible to development of a neurological disease or disorder to the HSV amplicon particles under conditions effective for infective transformation of the neural or pre-neural cells of the patient, wherein the therapeutic transgene product is expressed in vivo in the neural or pre-neural cells, thereby inhibiting development of the neurological disease or disorder.

A seventh aspect of the present invention relates to a method of expressing a therapeutic gene product in a patient which includes providing HSV amplicon particles of the present invention that include a transgene encoding a therapeutic transgene product and exposing patient cells to the HSV amplicon particles under conditions effective for infective transformation of the cells, wherein the therapeutic transgene product is expressed in vivo in transformed cells.

In an effort to enhance amplicon titers, the present invention involves introduction in trans of a vector including a sequence which encodes a virion host shutoff protein. Co-transfection of this plasmid, specifically one containing the HSV virion host shutoff ("vhs") protein-encoding gene UL41, with the amplicon and packaging reagents results in a 10-fold higher amplicon titer and stocks that do not exhibit the pseudotransduction phenomenon. To further enhance packaging efficiency, the HSV transcriptional activator VP16 was introduced into packaging cells prior to the packaging components. Pre-loading of packaging cells with VP16 led to an additional enhancement of amplicon titers, an effect that did not occur in the absence of vhs. Increased helper virus-free amplicon titers resulting from these modifications will make in vivo transduction experiments more feasible.

BRIEF DESCRIPTION OF THE DRAWINGS

FIG. 1A is a map of the empty amplicon vector pHSVlac, which includes the HSV-1 a segment (cleavage/packaging or pac signal), the HSV-1 c region (origin of replication), an ampicillin resistance marker, and an E. coli lacZ marker under control of HSV IE4 promoter and SV40 polyadenylation signal. FIG. 1B illustrates insertion of a transgene into BamHI site adjacent the HSV-1 a segment, forming pHSVlac/trans.

In FIG. 2B, the deleted a sequences in cos 6Δa and cos 48Δa are indicated by "X".

FIGS. 4B-C show the nucleotide sequence of a 4.3 kb fragment of the HSV-1 genome which contains the vhs gene with its native promoter and polyadenylation signal sequences (SEQ ID No: 1). The vhs coding sequence is underlined.

(FIG. 7B) was used to transduce NIH 3T3 fibroblasts. LacZ-positive cells were visualized by X-gal histochemistry and images were digitally acquired. Ten microliters of BAC-packaged HSVPrPUC/CMVegfp produced either without (FIG. 7C) or in the presence of pBS(vhs) (FIG. 7D) was used to transduce NIH 3T3 fibroblasts. Green fluoresecent protein (GFP)-positive cells were visualized with a fluorescent microscope and images digitally acquired. Three microliters of the same virus samples packaged either in the absence (FIG. 7E) or in the presence of pBS(vhs) (FIG. 7F) was stereotactically delivered into the striata of C57BL/6 mice. Animals were sacrificed four days later and prepared for visualization and quantitation of GFP-positive cells. Images used for morphological analyses were digitally acquired at 200× magnification on 40-µm sections. All compartments were processed for cell counting and GFP-positive cell numbers reflect cell counts throughout the entire injection site (FIG. 7G). The asterisk indicates a statistically significant difference (p<0.001) between amplicon stocks packages with BAC alone and those packaged with BAC in the presence of pBS(vhs).

(FIG. 8A), 22° C. (FIG. 8B), or 37° C. (FIG. 8C) for varying time periods. At 0, 30, 60, 120, and 180 minutes following initiation of the incubations, aliquots were removed, titered on NIH 3T3 cells, and expression titer data represented as green-forming units per milliliter. Another set of HSVPrPUC/CMVegfp stocks were subjected to a series of freeze-thaw cycles to determine sensitivity of viral particles to freeze fracture. Following each cycle, aliquots were removed, titered on NIH 3T3 cells, and expression titer data represented as green-forming units per milliliter (gfu/ml; FIG. 8D).

FIGS. 9A-B). Error bars represent standard deviation. Western blot analysis was performed to determine levels of VP16 expression in various combinations of helper virus-free packaging components (FIG. 9C). Lysates were harvested 48 h following introduction of BAC reagent. Lane designations are the following: BHK cells alone (Lane 1); BHK cells transfected with BAC only (Lane 2); BHKs transfected with pGRE$_5$vp16 24 h prior to BAC transfection in the absence of dexamethasone (Lane 3); and BHKs transfected with pGRE$_5$vp16 24 h prior to BAC transfection in the presence of 100 nM dexamethasone (Lane 4). The 65-kDa VP16 protein was detected using a VP16-specific monoclonal antibody and goat anti-mouse secondary antibody in combination with a chemiluminescent detection kit.

FIG. 16B is an enlarged view of the most crowded region. See Table 2, Example 4, for spot numbering and measurements.

FIGS. 17B-C are enlarged views of the two most crowded regions. See Table 2, Example 4, for spot numbering and measurements.

DETAILED DESCRIPTION OF THE INVENTION

Figure 1A:
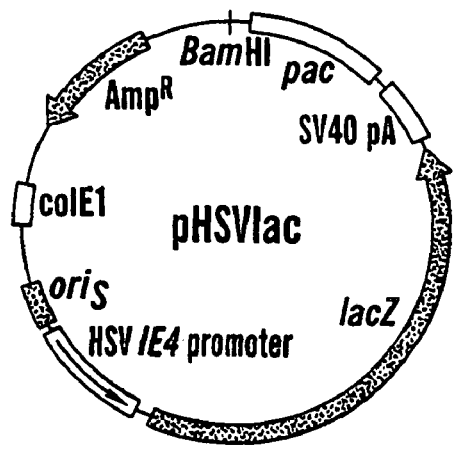
FIGS. 1A-B are maps of suitable amplicon vectors.
Figure 1B:
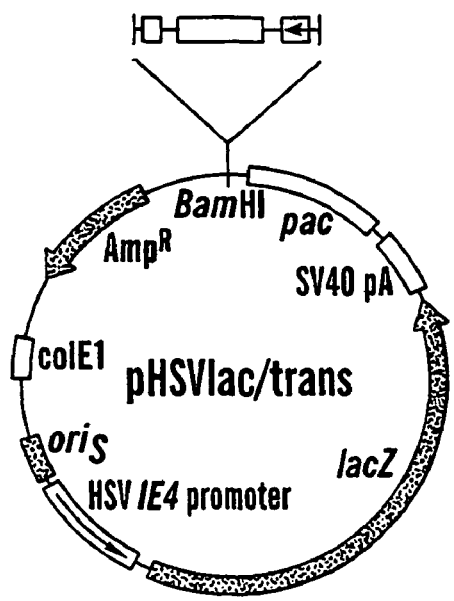
Figure 2A:
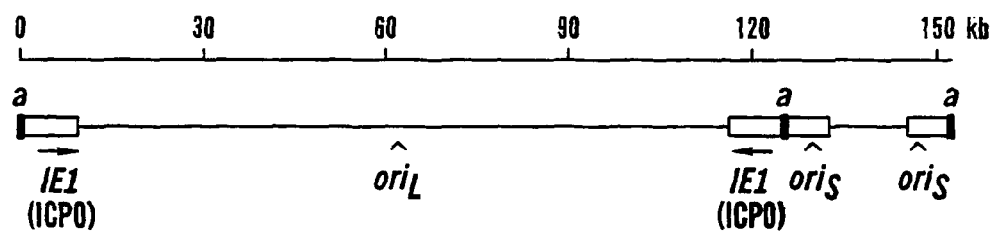
FIGS. 2A-B are maps of the HSV-1 genome and the overlapping 5 cosmid set C6Δa48Δa (cos 6Δα, cos 28, cos 14, cos 56, and cos 48Δa) (Fraefel et al., "Helper virus-free transfer of herpes simplex virus type 1 plasmid vectors into neural cells," J. Virol., 70:7190-7197 (1996), which is hereby incorporated by reference in its entirety). In the HSV-1 genome of FIG. 2A, only the IE4 gene, $ori_S$, and $ori_L$ are shown. The a sequences, which contain the cleavage/packaging sites, are located at the junction between long and short segments and at both termini.
Figure 2B:
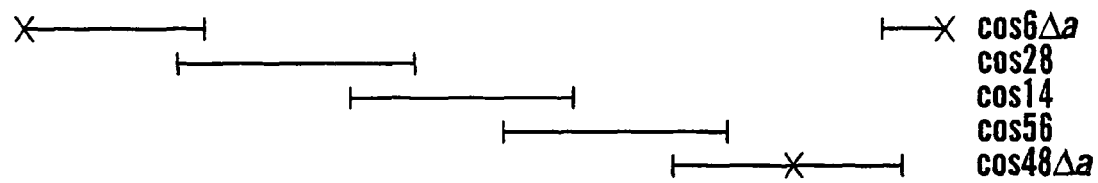
Figure 3:
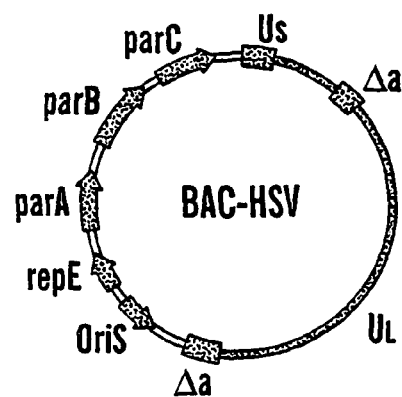
FIG. 3 is a map of the HSV bacterial artificial chromosome (HSV-BAC).

One aspect of the present invention relates to a method for producing herpes simplex virus (HSV) amplicon particles. This method is carried out by co-transfecting a host cell with several vectors and then isolating HSV amplicon particles produced by the host cell. The vectors used to transfect the host cell include: (i) an amplicon vector comprising an HSV origin of replication, an HSV cleavage/packaging signal, and a heterologous transgene expressible in a patient; (ii) one or more vectors individually or collectively encoding all essential HSV genes but excluding all cleavage/packaging signals; and (iii) a vhs expression vector encoding a virion host shutoff protein. As a result of the transgene being included in the HSV amplicon vector, the HSV amplicon particles include the transgene.

The amplicon vector is any HSV amplicon vector which includes an HSV origin of replication, an HSV cleavage/packaging signal, and a heterologous transgene expressible in a patient. The amplicon vector can also include a selectable marker gene and an antibiotic resistance gene.

The HSV cleavage/packaging signal can be any suitable cleavage/packaging signal such that the vector can be packaged into a particle that is capable of adsorbing to a cell (i.e., which is to be transformed). A suitable packaging signal is the HSV-1 a segment located at approximately nucleotides 127-1132 of the a sequence of the HSV-1 virus or its equivalent (Davison et al., "Nucleotide sequences of the joint between the L and S segments of herpes simplex virus types 1 and 2," *J. Gen. Virol.* 55:315-331 (1981), which is hereby incorporated by reference in its entirety).

The HSV origin of replication can be any suitable origin of replication which allows for replication of the amplicon vector in the host cell which is to be used for replication and packaging of the vector into the HSV amplicon particles. A suitable origin of replication is the HSV-1 c region which contains the HSV-1 $ori_s$ segment located at approximately nucleotides 47-1066 of the HSV-1 virus or its equivalent (McGeogh et al., *Nucl. Acids Res.* 14:1727-1745 (1986), which is hereby incorporated by reference in its entirety). Origin of replication signals from other related viruses (e.g., HSV-2) can also be used.

Selectable marker genes are known in the art and include, without limitation, galactokinase, beta-galactosidase, chloramphenicol acetyltransferase, beta-lactamase, green fluorescent protein ("gfp"), alkaline phosphate, etc.

Antibiotic resistance genes are known in the art and include, without limitation, ampicillin, streptomycin, spectromycin, etc.

A number of suitable empty amplicon vectors have previously been described in the art, including without limitation: pHSVlac (ATCC Accession 40544; U.S. Pat. No. 5,501,979 to Geller et al.; Stavropoulos and Strathdee, "An enhanced packaging system for helper-dependent herpes simplex virus vectors," *J. Virol.*, 72:7137-43 (1998), which are hereby incorporated by reference in their entirety) and pHENK (U.S. Pat. No. 6,040,172 to Kaplitt et al., which is hereby incorporated by reference. The pHSVlac vector includes the HSV-1 a segment, the HSV-1 c region, an ampicillin resistance marker, and an *E. coli* lacZ marker. The pHENK vector include the HSV-1 a segment, an HSV-1 ori segment, an ampicillin resistance marker, and an *E. coli* lacZ marker under control of the promoter region isolated from the rat preproenkephalin gene (i.e., a promoter operable in brain cells).

These empty amplicon vectors can be modified by introducing therein, at an appropriate restriction site, either a complete transgene which has already been assembled or a coding sequence can be ligated into an empty amplicon vector which already contains appropriate regulatory sequences (promoter, enhancer, polyadenylation signal, transcription terminator, etc.) positioned on either side of the restriction site where the coding sequence is to be inserted, thereby forming the transgene upon ligation. Alternatively, when using the pHSVlac vector, the lacZ coding sequence can be excised using appropriate restriction enzymes and replaced with a coding sequence for the transgene.

The use of restriction enzymes for cutting DNA and the use of DNA ligase to ligate together two or more DNA molecules can be performed using conventional molecular genetic manipulation for subcloning gene fragments, as described by Sambrook et al., *Molecular Cloning: A Laboratory Manual*, Cold Springs Laboratory, Cold Springs Harbor, N.Y. (1989); Ausubel et al. (ed.), *Current Protocols in Molecular Biology*, John Wiley & Sons (New York, N.Y.) (1999 and preceding editions); and U.S. Pat. No. 4,237,224 issued to Cohen and Boyer, which are hereby incorporated by reference in their entirety.

Suitable transgenes will include one or more appropriate promoter elements which are capable of directing the initiation of transcription by RNA polymerase, optionally one or more enhancer elements, and suitable transcription terminators or polyadenylation signals.

Basically, the promoter elements should be selected such that the promoter will be operable in the cells of the patient which are ultimately intended to be transformed (i.e., during gene therapy). A number of promoters have been identified which are capable of regulating expression within a broad range of cell types. These include, without limitation, HSV immediate-early 4/5 (IE4/5) promoter, cytomegalovirus ("CMV") promoter, SV40 promoter, and β-actin promoter. Likewise, a number of other promoters have been identified which are capable of regulating expression within a narrow range of cell types. These include, without limitation, neural-specific enolase (NSE) promoter, tyrosine hydroxylase (TH) promoter, GFAP promoter, preproenkephalin (PPE) promoter, myosin heavy chain (MHC) promoter, insulin promoter, cholineacetyltransferase (CHAT) promoter, dopamine β-hydroxylase (DBH) promoter, calmodulin dependent kinase (CamK) promoter, c-fos promoter, c-jun promoter, vascular endothelial growth factor (VEGF) promoter, erythropoietin (EPO) promoter, and EGR-1 promoter.

The transcription termination signal should, likewise, be selected such that they will be operable in the cells of the patient which are ultimately intended to be transformed. Suitable transcription termination signals include, without limitation, polyA signals of HSV genes such as the vhs polyadenylation signal, SV40 polyA signal, and CMV IE1 polyA signal.

When used for gene therapy, the transgene encodes a therapeutic transgene product, which can be either a protein or an RNA molecule.

Therapeutic RNA molecules include, without limitation, antisense RNA, inhibitory RNA (RNAi), and an RNA ribozyme. The RNA ribozyme can be either cis or trans acting, either modifying the RNA transcript of the transgene to afford a functional RNA molecule or modifying another nucleic acid molecule. Exemplary RNA molecules include, without limitation, antisense RNA, ribozymes, or RNAi to nucleic acids for huntingtin, alpha synuclein, scatter factor, amyloid precursor protein, p53, VEGF, etc.

Therapeutic proteins include, without limitation, receptors, signaling molecules, transcription factors, growth factors, apoptosis inhibitors, apoptosis promoters, DNA replication factors, enzymes, structural proteins, neural proteins, and histone or non-histone proteins. Exemplary protein receptors include, without limitation, all steroid/thyroid family members, nerve growth factor (NGF), brain derived neurotrophic factor (BDNF), neurotrophins 3 and 4/5, glial derived neurotrophic factor (GDNF), cilary neurotrophic factor (CNTF), persephin, artemin, neurturin, bone morphogenetic factors (BMPs), c-ret, gp130, dopamine receptors (D1-D5), muscarinic and nicotinic cholinergic receptors, epidermal growth factor (EGF), insulin and insulin-like growth factors, leptin, resistin, and orexin. Exemplary protein signaling molecules include, without limitation, all of the above-listed receptors plus MAPKs, ras, rac, ERKs, NFKB, GSK3β, AKT, and PI3K Exemplary protein transcription factors include, without limitation, p300, CBP, HIF-1 alpha, NPAS1 and 2, HIF-1β, p53, p73, nurr 1, nurr 77, MASHs, REST, and NCORs. Exemplary neural proteins include, without limitation, neurofilaments, GAP-43, SCG-10, etc. Exemplary enzymes include, without limitation, TH, DBH, aromatic aminoacid decarboxylase, parkin, ubiquitin E3 ligases, ubiquitin conjugating enzymes, cholineacetyltransferase, neuropeptide processing enzymes, dopamine, VMAT and other catecholamine transporters. Exemplary histones include, without limitation, H1-5. Exemplary non-histones include, without limitation, ND10 proteins, PML, and HMG proteins. Exemplary pro- and anti-apoptotic proteins include, without limitation, bax, bid, bak, bcl-xs, bcl-xl, bcl-2, caspases, SMACs, and IAPs.

The one or more vectors individually or collectively encoding all essential HSV genes but excluding all cleavage/packaging signals can either be in the form of a set of vectors or a single bacterial-artificial chromosome ("BAC"), which is formed, for example, by combining the set of vectors to create a single, double-stranded vector. Preparation and use of a five cosmid set is disclosed in (Fraefel et al., "Helper virus-free transfer of herpes simplex virus type 1 plasmid vectors into neural cells," *J. Virol.*, 70:7190-7197 (1996), which is hereby incorporated by reference in its entirety). Ligation of the cosmids together to form a single BAC is disclosed in Stavropoulos and Strathdee, "An enhanced packaging system for helper-dependent herpes simplex virus vectors," *J. Virol.* 72:7137-43 (1998), which is hereby incorporated by reference in its entirety). The BAC described in Stavropoulos and Strathdee includes a pac cassette inserted at a BamHI site located within the UL41 coding sequence, thereby disrupting expression of the HSV-1 virion host shutoff protein.

By "essential HSV genes", it is intended that the one or more vectors include all genes which encode polypeptides that are necessary for replication of the amplicon vector and structural assembly of the amplicon particles. Thus, in the absence of such genes, the amplicon vector is not properly replicated and packaged within a capsid to form an amplicon particle capable of adsorption. Such "essential HSV genes" have previously been reported in review articles by Roizman ("The Function of Herpes Simplex Virus Genes: A Primer for Genetic Engineering of Novel Vectors," *Proc. Natl. Acad. Sci. USA* 93:11307-11312 (1996); "HSV Gene Functions: What Have We Learned That Could Be Generally Application to its Near and Distant Cousins?" *Acta Virologica* 43(2-3):75-80 (1999), which are hereby incorporated by reference in their entirety. Another source for identifying such essential genes is available at the Internet site operated by the Los Alamos National Laboratory, Bioscience Division, which reports the entire HSV-1 genome and includes a table identifying the essential HSV-1 genes. The genes currently identified as essential are listed in Table 1 below.

TABLE 1

Essential HSV-1 Genes

| Gene* | Protein (Function) | Genbank I.D. No. | Accession No.** |
|---|---|---|---|
| UL1 | virion glycoprotein L (gL) | 136775 | CAA32337 |
| UL5 | component of DNA helicase-primase complex | 74000 | CAA32341 |
| UL6 | minor capsid protein | 136794 | CAA32342 |
| UL7 | unknown | 136798 | CAA32343 |
| UL8 | DNA helicase/primase complex associated protein | 136802 | CAA32344 |
| UL8.5 | unknown*** | — | — |
| UL9 | oil-binding protein | 136806 | CAA32345 |
| UL15 | DNA cleavage/packaging protein | 139646 | CAA32330 |
| UL17 | tegument protein | 136835 | CAA32329 |
| UL18 | capsid protein, VP23 | 139191 | CAA32331 |
| UL19 | major capsid protein, VP5 | 137571 | CAA32332 |
| UL22 | virion glycoprotein H, gH | 138315 | CAA32335 |
| UL25 | DNA packaging virion protein | 136863 | CAA32317 |
| UL26 | serine protease, self-cleaves to form VP21 & VP24 | 139233 | CAA32318 |
| UL26.5 | capsid scaffolding protein, VP22a | 1944539 | CAA32319 |
| UL27 | virion glycoprotein B, gB | 138194 | CAA32320 |
| UL28 | DNA cleavage and packaging protein, ICP18.5 | 124088 | CAA32321 |
| UL29 | single-stranded DNA binding protein, ICP8 | 118746 | CAA32322 |
| UL30 | DNA polymerase | 118878 | CAA32323 |
| UL31 | UL34-associated nuclear protein | 136875 | CAA32324 |
| UL32 | cleavage and packaging protein | 136879 | CAA32307 |
| UL33 | capsid packaging protein | 136883 | CAA32308 |
| UL34 | membrane-associated virion protein | 136888 | CAA32309 |
| UL36 | very large tegument protein, ICP1/2 | 135576 | CAA32311 |
| UL37 | tegument protein, ICP32 | 136894 | CAA32312 |
| UL38 | capsid protein, VP19C | 418280 | CAA32313 |
| UL42 | DNA polymerase accessory protein | 136905 | CAA32305 |
| UL48 | alpha trans-inducing factor, VP16 | 114359 | CAA32298 |
| UL49 | putative microtubule-associated protein, VP22 | 136927 | CAA32299 |
| UL49.5 | membrane-associated virion protein | 1944541 | CAA32300 |
| UL52 | component of DNA helicase/primase complex | 136939 | CAA32288 |
| UL54 | regulation and transportation of RNA, ICP27 | 124180 | CAA32290 |
| α4 (RS1) | positive and negative gene regulator, ICP4 | 124141 | CAA32286 CAA32278 |
| US6 | virion glycoprotein D, gD | 73741 | CAA32283 |

*The complete genome of HSV-1 is reported at Genbank Accession No. X14112, which is hereby incorporated by reference in its entirety.
**Each of the listed Accession Nos. which report an amino acid sequence for the encoded proteins is hereby incorporated by reference in its entirety.
***UL8.5 maps to a transcript which overlaps and is in frame with the carboxyl terminal of UL9 (Baradaran et al., "Transcriptional analysis of the region of the herpes simplex virus type 1 genomecontaining the UL8, UL9, and UL10 genes and identification of a novel delayed-early gene product, OBPC," J. Virol. 68 (7):4251–4261 (1994), which is hereby incorporated by reference in its entirety).

The vhs vector can encode a virion host shutoff ("vhs") protein which is effective in regulating host cell transcription and translation activities. The vhs vector includes a DNA molecule encoding a vhs protein, which DNA molecule is operably coupled 5' to a promoter which is functional in the host cell and 3' to a transcription terminator which also is functional in the host cell.

One suitable vhs protein is the human herpesvirus 1 vhs protein, which has an amino acid sequence according to SEQ ID No: 2 as follows:

```
Met Gly Leu Phe Gly Met Met Lys Phe Ala His Thr His His Leu Val
 1               5                  10                  15
Lys Arg Arg Gly Leu Gly Ala Pro Ala Gly Tyr Phe Thr Pro Ile Ala
                20                  25                  30
Val Asp Leu Trp Asn Val

-continued

```
Pro Arg Arg His Val Ile His Asp Ala Pro Glu Ser Leu Asp Trp Leu
385                 390                 395                 400

Pro Asp Pro Met Thr Ile Thr Glu Leu Val Glu His Arg Tyr Ile Lys
            405                 410                 415

Tyr Val Ile Ser Leu Ile Gly Pro Lys Glu Arg Gly Pro Trp Thr Leu
                420                 425                 430

Leu Lys Arg Leu Pro Ile Tyr Gln Asp Ile Arg Asp Glu Asn Leu Ala
            435                 440                 445

Arg Ser Ile Val Thr Arg His Ile Thr Ala Pro Asp Ile Ala Asp Arg
        450                 455                 460

Phe Leu Glu Gln Leu Arg Thr Gln Ala Pro Pro Pro Ala Phe Tyr Lys
465                 470                 475                 480

Asp Val Leu Ala Lys Phe Trp Asp Glu
                485
```

This protein is encoded by a DNA molecule having a nucleotide sequence according to SEQ ID No: 3 as follows:

```
atgggtttgt tcgggatgat gaagtttgcc cacacacacc atctggtcaa gcgccggggc    60
cttgggcccc cggccgggta cttcacccccc attgccgtgg acctgtgaa cgtcatgtac   120
acgttggtgg tcaaatatca gcgccgatac cccagttacg accgcgaggc cattacgcta   180
cactgcctct gtcgcttatt aaaggtgttt acccaaaagt cccttttccc catcttcgtt   240
accgatcgcg gggtcaattg tatggagccg gttgtgtttg gagccaaggc catcctggcc   300
cgcacgacgg cccagtgccg gacggacgag gaggccagtg acgtggacgc ctctccaccg   360
ccttccccca tcaccgactc cagacccagc tctgcctttt ccaacatgcg ccggcgcggc   420
acctctctgg cctcggggac ccgggggacg gccgggtccg gagccgcgct gccgtccgcc   480
gcgccctcga agccggccct gcgtctggcg catctgttct gtattcgcgt tctccgggcc   540
ctggggtacg cctacattaa ctcgggtcag ctggaggcgg acgatgcctg cgccaacctc   600
tatcacacca acacggtcgc gtacgtgtac accacggaca ctgacctcct gttgatgggc   660
tgtgatattg tgttggatat tagcgcctgc tacattccca cgatcaactg tcgcgatata   720
ctaaagtact ttaagatgag ctaccccag ttcctggcct ctttgtccgc tgccacaccg   780
acctccatcc caataacacc tacgcctccg tggaggatgt gctgcgcgaa tgtcactgga   840
cccccccgag tcgctctcag acccggcggg ccatccgccg gaacacacc agctcgcgct   900
ccacggaaac caggcccct ctgccgccgg ccgccggcgg caccgagacg cgcgtctcgt   960
ggaccgaaat tctaacccaa cagatcgccg gcggatacga agacgacgag gacctccccc  1020
tggatccccg ggacgttacc gggggccacc ccggccccag gtcgtcctcc tcggagatac  1080
tcaccccgcc cgagctcgtc caggtcccga acgcgcagct gctggaagag caccgcagtt  1140
atgtggccaa cccgcgacgc cacgtcatcc acgacgcccc agagtccctg gactggctcc  1200
ccgatcccat gaccatcacc gagctggtgg aacaccgcta cattaagtac gtcatatcgc  1260
ttatcggccc caaggagcgg gggccgtgga ctcttctgaa acgcctgcct atctaccagg  1320
acatccgcga cgaaaacctg gcgcgatcta tcgtgacccg gcatatcacg gcccctgata  1380
tcgccgacag gtttctggag cagttgcgga cccaggcccc cccacccgcg ttctacaagg  1440
acgtcctggc caaattctgg gacgagtag                                    1469
```

The amino acid and encoding nucleotide sequences of human HSV-1 vhs are reported at Genbank Accession Nos. CAA96525 and Z72338, which are hereby incorporated by reference in their entirety. The above-listed nucleotide sequence corresponds to nt 1287-2756 of SEQ ID No: 1.

Other suitable vhs proteins include human herpesvirus 2 vhs protein, whose amino acid and encoding nucleotide sequences are reported, respectively, as Genbank Accession Nos. AAC58447 and AF007816, which are hereby incorporated by reference in their entirety; human herpesvirus 3 vhs protein, whose amino acid and sequence is reported as Genbank Accession No. P09275, which is hereby incorporated by reference in its entirety; bovine herpesvirus 1 vhs protein, whose amino acid and encoding nucleotide sequences are reported, respectively, as Genbank Accession Nos. CAA90927 and Z54206, which are hereby incorporated by reference in their entirety; bovine herpesvirus 1.1 vhs protein, whose amino acid and encoding nucleotide sequences are reported, respectively, as Genbank Accession Nos. NP_045317 and NC_001847, which are hereby incorporated by reference in their entirety; gallid herpesvirus 1 vhs protein, whose amino acid and encoding nucleotide sequences are reported, respectively, as Genbank Accession Nos. AAD56213 and AF168792, which are hereby incorporated by reference in their entirety; gallid herpesvirus 2 vhs protein, whose amino acid and encoding nucleotide sequences are reported, respectively, as Genbank Accession Nos. AAA80558 and L40429, which are hereby incorporated by reference in their entirety; suid herpesvirus 1 vhs protein, whose amino acid and sequence is reported as Genbank Accession No. P36314, which is hereby incorporated by reference in its entirety; baboon herpesvirus 2 vhs protein, whose amino acid and encoding nucleotide sequences are reported, respectively, as Genbank Accession Nos. AAG01880 and AF294581, which are hereby incorporated by reference in their entirety; pseudorabies virus vhs protein, whose amino acid and encoding nucleotide sequences are reported, respectively, as Genbank Accession Nos. AAB25948 and S57917, which are hereby incorporated by reference in their entirety; cercopithecine herpesvirus 7 vhs protein, whose amino acid and encoding nucleotide sequences are reported, respectively, as Genbank Accession Nos. NP_077432 and NC_002686, which are hereby incorporated by reference in their entirety; meleagrid herpesvirus 1 vhs protein, whose amino acid and encoding nucleotide sequences are reported, respectively, as Genbank Accession Nos. Np_073335 and NC_002641, which are hereby incorporated by reference in their entirety; equine herpesvirus 1 vhs protein, whose amino acid and encoding nucleotide sequences are reported, respectively, as Genbank Accession Nos. NP_041028 and NC_001491, which are hereby incorporated by reference in their entirety; and equine herpesvirus 4 vhs protein, whose amino acid sequence is reported as Genbank Accession No. T42562, which is hereby incorporated by reference in its entirety.

Figure 4A:
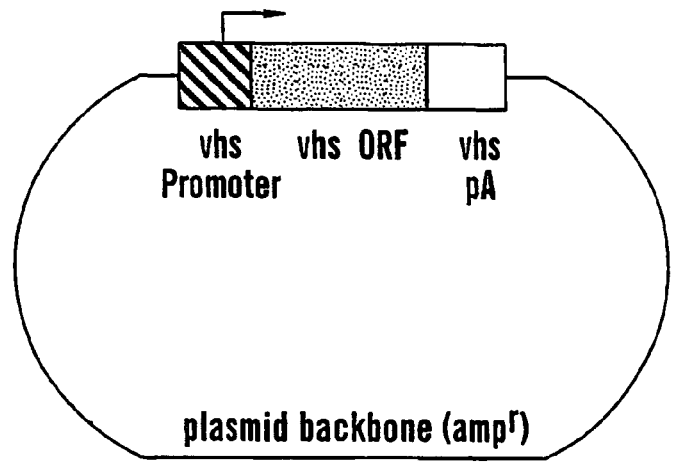
FIG. 4A is a map of pBSKS(vhs), a plasmid vector which includes the HSV-1 vhs coding region (SEQ ID No: 3) operatively coupled to its native transcriptional control elements.

According to one approach, the vhs vector includes a DNA molecule encoding the HSV virion host shutoff protein operatively coupled to its native transcriptional control elements. A vector of this type is prepared by excising an approximately 4.3 kb HpaI/HindIII restriction fragment from the previously reported cosmid56 (Cunningham and Davison, "A cosmid-based system for construction mutants of herpes simplex type 1," *Virology*, 197:116-124 (1993), which is hereby incorporated by reference in its entirety) and cloning the fragment into pBSKSII (Stratagene, Inc.) to create pBSKS(vhs). A map of pBSKS(vhs) is illustrated in FIG. 4A. The 4.3 kb fragment includes nts 89658-93923 (complement) of the HSV-1 genome (SEQ ID No: 1, see FIGS. 4B-C), as reported at Genbank Accession No. X14112, which is hereby incorporated by reference in its entirety.

Optionally, the host cell which is co-transfected also expresses a suitable VP16 tegument protein. This can be achieved either by (a) transfecting the host cell prior to the co-transfection step with a vector encoding the VP16 protein, or (b) co-transfecting a host cell which stably expresses the VP16 protein.

One suitable VP16 protein is the HSV-1 VP16 protein, which is characterized by an amino acid sequence according to SEQ ID No: 4 as follows:

```
Met Asp Leu Leu Val Asp Glu Leu Phe Ala Asp Met Asn Ala Asp Gly
 1               5                  10                  15

Ala Ser Pro Pro Pro Arg Pro Ala Gly Gly Pro Lys Asn Thr Pro
                20                  25                  30

Ala Ala Pro Pro Leu Tyr Ala Thr Gly Arg Leu Ser Gln Ala Gln Leu
            35                  40                  45

Met Pro Ser Pro Pro Met Pro Val Pro Pro Ala Ala Leu Phe Asn Arg
        50                  55                  60

Leu Leu Asp Asp Leu Gly Phe Ser Ala Gly Pro Ala Leu Cys Thr Met
 65                  70                  75                  80

Leu Asp Thr Trp Asn Glu Asp Leu Phe Ser Ala Leu Pro Thr Asn Ala
                85                  90                  95

Asp Leu Tyr Arg Glu Cys Lys Phe Leu Ser Thr Leu Pro Ser Asp Val
                100                 105                 110

Val Glu Trp Gly Asp Ala Tyr Val Pro Glu Arg Thr Gln Ile Asp Ile
            115                 120                 125

Arg Ala His Gly Asp Val Ala Phe Pro Thr Leu Pro Ala Thr Arg Asp
        130                 135                 140

Gly Leu Gly Leu Tyr Tyr Glu Ala Leu Ser Arg Phe Phe His Ala Glu
145                 150                 155                 160

Leu Arg Ala Arg Glu Glu Ser Tyr Arg Thr Val Leu Ala Asn Phe Cys
                165                 170                 175

Ser Ala Leu Tyr Arg Tyr Leu Arg Ala Ser Val Arg Gln Leu His Arg
            180                 185                 190
```

-continued

```
Gln Ala His Met Arg Gly Arg Asp Arg Asp Leu Gly Glu Met Leu Arg
        195                 200                 205

Ala Thr Ile Ala Asp Arg Tyr Tyr Arg Glu Thr Ala Arg Leu Ala Arg
    210                 215                 220

Val Leu Phe Leu His Leu Tyr Leu Phe Leu Thr Arg Glu Ile Leu Trp
225                 230                 235                 240

Ala Ala Tyr Ala Glu Gln Met Met Arg Pro Asp Leu Phe Asp Cys Leu
                245                 250                 255

Cys Cys Asp Leu Glu Ser Trp Arg Gln Leu Ala Gly Leu Phe Gln Pro
            260                 265                 270

Phe Met Phe Val Asn Gly Ala Leu Thr Val Arg Gly Val Pro Ile Glu
        275                 280                 285

Ala Arg Arg Leu Arg Glu Leu Asn His Ile Arg Glu His Leu Asn Leu
    290                 295                 300

Pro Leu Val Arg Ser Ala Ala Thr Glu Glu Pro Gly Ala Pro Leu Thr
305                 310                 315                 320

Thr Pro Pro Thr Leu His Gly Asn Gln Ala Arg Ala Ser Gly Tyr Phe
                325                 330                 335

Met Val Leu Ile Arg Ala Lys Leu Asp Ser Tyr Ser Ser Phe Thr Thr
            340                 345                 350

Ser Pro Ser Glu Ala Val Met Arg Glu His Ala Tyr Ser Arg Ala Arg
        355                 360                 365

Thr Lys Asn Asn Tyr Gly Ser Thr Ile Glu Gly Leu Leu Asp Leu Pro
    370                 375                 380

Asp Asp Asp Ala Pro Glu Glu Ala Gly Leu Ala Ala Pro Arg Leu Ser
385                 390                 395                 400

Phe Leu Pro Ala Gly His Thr Arg Arg Leu Ser Thr Ala Pro Pro Thr
                405                 410                 415

Asp Val Ser Leu Gly Asp Glu Leu His Leu Asp Gly Glu Asp Val Ala
            420                 425                 430

Met Ala His Ala Asp Ala Leu Asp Asp Phe Asp Leu Asp Met Leu Gly
        435                 440                 445

Asp Gly Asp Ser Pro Gly Pro Gly Phe Thr Pro His Asp Ser Ala Pro
    450                 455                 460

Tyr Gly Ala Leu Asp Met Ala Asp Phe Glu Phe Glu Gln Met Phe Thr
465                 470                 475                 480

Asp Ala Leu Gly Ile Asp Glu Tyr Gly Gly
                485                 490
```

The DNA molecule encoding HSV-1 vp16 has a nucleotide sequence according to SEQ ID No: 5 as follows:

```
atggacctct tggtcgacga gctgtttgcc gacatgaacg cggacggcgc ttcgccaccg    60
cccccccgcc cggccggggg tcccaaaaac accccggcgg cccccccgct gtacgcaacg   120
gggcgcctga gccaggccca gctcatgccc tccccaccca tgcccgtccc ccccgccgcc   180
ctctttaacc gtctcctcga cgacttgggc tttagcgcgg gccccgcgct atgtaccatg   240
ctcgatacct ggaacgagga tctgttttcg gcgctaccga ccaacgccga cctgtaccgg   300
gagtgtaaat tcctatcaac gctgcccagc gatgtggtgg aatgggggga cgcgtacgtc   360
cccgaacgca cccaaatcga cattcgcgcc cacggcgacg tggccttccc tacgcttccg   420
gccacccgcg acggcctcgg gctctactac gaagcgctct ctcgtttctt ccacgccgag   480
ctacgggcgc gggaggagag ctatcgaacc gtgttggcca acttctgctc ggccctgtac   540
```

```
                                    -continued
cggtacctgc gcgccagcgt ccggcagctg caccgccagg cgcacatgcg cggacgcgat    600
cgcgacctgg gagaaatgct gcgcgccacg atcgcggaca ggtactaccg agagaccgct    660
cgtctggcgc gtgttttgtt tttgcatttg tatctatttt tgacccgcga gatcctatgg    720
gccgcgtacg ccgagcagat gatgcggccc gacctgtttg actgcctctg ttgcgacctg    780
gagagctggc gtcagttggc gggtctgttc cagcccttca tgttcgtcaa cggagcgctc    840
accgtccggg gagtgccaat cgaggcccgc cggctgcggg agctaaacca cattcgcgag    900
caccttaacc tcccgctggt gcgcagcgcg gctacggagg agccaggggc gccgttgacg    960 accccctccca ccctgcatgg caaccaggcc cgcgcctctg ggtactttat ggtgttgatt    1020
cgggcgaagt tggactcgta ttccagcttc acgacctcgc cctccgaggc ggtcatgcgg    1080
gaacacgcgt acagccgcgc gcgtacgaaa aacaattacg ggtctaccat cgagggcctg    1140
ctcgatctcc cggacgacga cgcccccgaa gaggcgggc tggcggctcc gcgcctgtcc    1200
tttctccccg cgggacacac gcgcagactg tcgacggccc ccccgaccga tgtcagcctg    1260
ggggacgagc tccacttaga cggcgaggac gtggcgatgg cgcatgccga cgcgctagac    1320
gatttcgatc tggacatgtt gggggacggg gattccccgg ggccgggatt tacccccccac   1380 gactccgccc cctacggcgc tctggatatg gccgacttcg agtttgagca gatgtttacc    1440
gatgcccttg gaattgacga gtacggtggg tag                                 1473
```

The amino acid and encoding nucleotide sequence of human HSV-1 VP16 are reported, respectively, as Genbank Accession Nos. CAA32304 and X14112, which are hereby incorporated by reference in their entirety.

Other suitable VP16 proteins include human herpesvirus 2 VP16 protein, whose amino acid and encoding nucleotide sequences are reported, respectively, as Genbank Accession Nos. NP_044518 and NC_001798, which are hereby incorporated by reference in their entirety; bovine herpesvirus 1 VP16 protein, whose amino acid and encoding nucleotide sequences are reported, respectively, as Genbank Accession Nos. CAA90922 and Z54206, which are hereby incorporated by reference in their entirety; bovine herpesvirus 1.1 VP16 protein, whose amino acid and encoding nucleotide sequences are reported, respectively, as Genbank Accession Nos. NP_045311 and NC_001847, which are hereby incorporated by reference in their entirety; gallid herpesvirus 1 VP16 protein, whose amino acid and encoding nucleotide sequences are reported, respectively, as Genbank Accession Nos. BAA32584 and AB012572, which are hereby incorporated by reference in their entirety; gallid herpesvirus 2 VP16 protein, whose amino acid and encoding nucleotide sequences are reported, respectively, as Genbank Accession Nos. NP_057810 and NC_002229, which are hereby incorporated by reference in their entirety; meleagrid herpesvirus 1 VP16 protein, whose amino acid and encoding nucleotide sequences are reported, respectively, as Genbank Accession Nos. AAG30088 and AF282130, which are hereby incorporated by reference in their entirety; and equine herpesvirus 4 VP16 protein, whose amino acid and encoding nucleotide sequences are reported as Genbank Accession Nos. NP_045229 and NC_001844, which are hereby incorporated by reference in their entirety.

Figure 5:
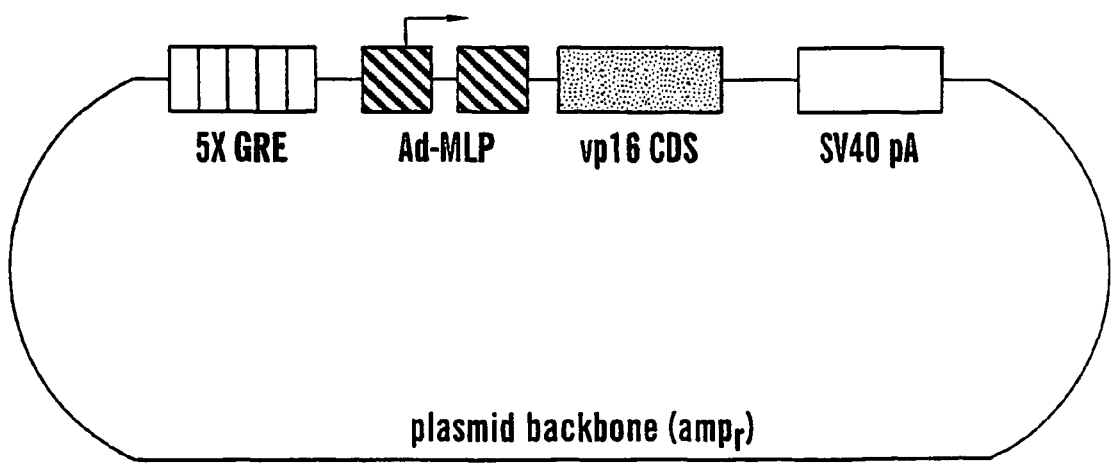
FIG. 5 is a map of pGRE$_5$vp16, a plasmid vector which includes five glucocorticoid responsive elements located upstream of a adenovirus major late promoter having a TATA box, an HSV vp16 coding sequence (SEQ ID No: 5), and an SV40 polyadenylation signal. The plasmid also includes an ampicillin resistance marker.

When performing an initial transfection step prior to co-transfection, the transfection with a vector encoding the VP16 protein can be carried out at least about 1 hour before the co-transfection step, more preferably at least about 4 hours before, and most preferably at least about 12 hours before. Maximal amplicon particle titers have been achieved following transfection of host cells (with VP16) about 24 hours prior to the co-transfection step described below. When prior transfection of the host cell is carried out, a preferred vector encoding the HSV-1 VP16 protein is vector pGRE$_5$vp16, whose structure is illustrated in FIG. 5.

In host cells transiently expressing VP16, the plasmid encoding VP16 is lost in up to about 50% of the cells per doubling of the cell population.

Stable expression of VP16 can be achieved either using a stable plasmid which is copied and partitioned among dividing host cells with acceptable fidelity or by integration of the VP16 into the host cell genome. Plasmids which are stable in vitro cell lines are known in the art and can be used to introduce UL48 thereon. Also, integration can be carried out according to known procedures.

Preparation of HSV amplicon particles can be carried out by co-transfecting a suitable host cell with (i) the amplicon vector, (ii) either the set of cosmid vectors or BAC, and (iii) the vhs expression vector. Basically, the various vectors are introduced into a single medium (e.g., Opti-MEM available from Gibco-BRL, Bethesda, Md.) within a container (e.g., sterile polypropylene tube), forming a DNA mix. The weight ratio of BAC:amplicon vector is between about 1-10:1, preferably about 5-10:1, and the weight ratio of 5 cosmid set (in total):amplicon vector is between about 1-10:1, preferably about 2-7:1. The DNA mix is later introduced into a container (with Lipofectanine reagent) which has been seeded with the host cells to be co-transfected. Thereafter, the transfection mix is diluted with an equal volume of a selection medium (e.g., DMEM plus 20% FBS, 2% penicillin/streptomycin, and 2 mM hexamethylene bis-acetamide (HMBA)) and incubated for several days. Virion particles are released from the host cells by sonication and purified from host cell protein/membrane components via ultracentrifugation.

When prior transfection is effected, allowing the host cells to express HSV-1 VP16 prior to co-transfection as described above, the cells plated for packaging were first allowed to adhere to a culture dish and subsequently transfected with pGRE$_5$vp16 using Lipofectamine reagent. Following suitable incubation, the transfection mix was removed, complete medium (e.g., DMEM plus 10% FBS, 1% penicillin/streptomycin) was added, and the cultures were incubated at 37° C. until the packaging co-transfection step described above.

Suitable host cells which can be co-transfected for preparation of HSV amplicon particles are eukaryotic cells, preferably mammalian cells. Exemplary host cells include, without limitation, BHK cells, NIH 3T3 cells, 2-2 cells, 293 cells, and RR1 cells.

When the HSV amplicon particles are harvested from the host cell medium, the amplicon particles are substantially pure (i.e., free of any other virion particles) and present at a concentration of greater than about $1\times10^6$ particles per milliliter. To further enhance the use of the amplicon particles, the resulting stock can also be concentrated, which affords a stock of isolated HSV amplicon particles at a concentration of at least about $1\times10^7$ particles per milliliter.

The resulting amplicon particles produced according to the present invention, i.e., in the presence of vhs and, optionally VP16, both of which can be expressed in host cells prior to packaging, are substantially different in kind from the virion particles which can be prepared using known helper virus methods (see Examples 1 and 4).

The concentrated stock of HSV amplicon particles is effectively a composition of the HSV amplicon particles in a suitable carrier. Alternatively, the HSV amplicon particles may also be administered in injectable dosages by dissolution or suspension of these materials in a physiologically acceptable diluent with a pharmaceutical carrier. Such carriers include sterile liquids, such as water and oils, with or without the addition of a surfactant and other pharmaceutically and physiologically acceptable carriers, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the HSV amplicon particles, in solution or suspension, may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The pharmaceutical composition is preferably in liquid form, such as a solution, suspension, or emulsion. Typically, the composition will contain at least about $1\times10^7$ amplicon particles/ml, together with the carrier, excipient, stabilizer, etc.

A further aspect of the present invention relates to a system for preparing HSV amplicon particles. The system includes (i) an empty amplicon vector as described above, which includes an HSV origin of replication, an HSV cleavage/packaging signal, and a transgene insertion site (at which a transgene may be inserted, as described above), (ii) one or more vectors individually or collectively encoding all essential HSV genes but excluding all cleavage/packaging signals, and (iii) a vhs expression vector encoding a virion host shutoff protein. The vhs expression vector is of the type described above. The system is characterized as being able to produce HSV amplicon particles of the present invention when the system is introduced (i.e., co-transfected) into a suitable host cell. The system may further include, as described above, a host cell which stably expresses an HSV VP16 protein and/or a vector encoding the HSV VP16 protein.

Yet another aspect of the present invention relates to a kit for preparing HSV amplicon particles of the present invention. The kits includes: (i) an amplicon vector comprising an HSV origin of replication, an HSV cleavage/packaging signal, and a transgene insertion site (at which a transgene may be inserted, as described above), (ii) one or more vectors individually or collectively encoding all essential HSV genes but excluding all cleavage/packaging signals, (iii) a vhs expression vector encoding an virion host shutoff protein, (iv) a population of host cells susceptible to transfection by the amplicon vector, the vhs expression vector, and the one or more vectors, and (v) directions for transfecting the host cells under conditions to produce HSV amplicon particles. The vhs expression vector is of the type described above. The kit may further include, as described above, a host cell which stably expresses an HSV VP16 protein and/or a vector encoding the HSV VP16 protein.

Yet another aspect of the present invention relates generally to a method of expressing a therapeutic gene product in a patient using the HSV amplicon particles of the present invention which contain a transgene encoding a therapeutic gene product. Basically, this method is carried out by providing such HSV amplicon particles and exposing patient cells to the HSV amplicon particles under conditions effective for infective transformation of the cells, wherein the therapeutic transgene product is expressed in vivo in transformed cells. As noted below, transformation of the patient cells can be carried out in vivo or ex vivo.

HSV-1 has a wide host range and infects many cell types in mammals and birds (including chickens, rats, mice, monkeys, humans) (Spear et al., *DNA Tumor Viruses*, pp. 615-746, Tooze, ed., Cold Spring Harbor Laboratory, Cold Spring Harbor, New York (1981), which is hereby incorporated by reference in its entirety). HSV-1 can lytically infect a wide variety of cells including, e.g., neurons, fibroblasts, and macrophages. In addition, HSV-1 infects post-mitotic neurons in adult animals and can be maintained indefinitely in a latent state (Stevens, *Curr. Topics in Microbiol. and Immunol.* 70:31-50 (1975), which is hereby incorporated by reference in its entirety). Two lines of evidence suggest that HSV-1 can infect most, if not all, kinds of neurons in the central nervous system. First, following inoculation of HSV-1 in the periphery, a burst of virus production ascends the neuroaxis, initially in the sensory or motor neurons innervating the site of inoculation, then in the spinal cord, brain stem, cerebellum, and cerebral cortex (Koprowski, *In Persistent Viruses*, pp. 691-699, Stevens, ed., Academic Press, New York, N.Y. (1978), which is hereby incorporated by reference in its entirety). Second, attempts to mimic HSV-1 latency in tissue culture with different preparations of neurons have required high temperature, DNA synthesis inhibitors, and antisera directed against HSV-1 virions to prevent lytic infection for spreading to all neurons (Wigdahl et al., *Proc. Natl. Acad. Sci. USA* 81:6217-6201 (1984), which is hereby incorporated by reference in its entirety).

Because HSV-1 infects a wide range of animals, the HSV amplicon particles of the present invention can be used on a wide variety of mammals and birds. Preferably, the HSV amplicon particles are used on mammals, most preferably humans, to effect expression of the therapeutic transgene product. Thus, as used herein, patient refers generally to mammals and birds, as well as humans specifically.

When exposing the patient cells to the HSV amplicon particles, an in vivo route of delivery is performed by administering the HSV amplicon particles directly to the patient cells which are to be transformed. The administering can be achieved in a manner which is suitable to effect delivery and subsequent patient cell transformation, including, without limitation, intraparenchymal, intramuscular, intravenous, intracerebroventricular, subcutaneous, or intramucosal delivery.

Alternatively, an ex vivo route of delivery is performed by providing patient cells (either removed from the patient or obtained from a donor), exposing the cells ex vivo to the HSV amplicon particles, and then introducing the transformed cells into the patient. Stem cells, embryonic or progenitor, can be effectively transformed and then introduced into the patient at a desired location. For non-motile transformed cells, such cells are preferably administered to the patient at the site where the cells are intended to reside. For actively or passively motile transformed cells, such cells may be administered in a manner which is effective to deliver the transformed cells into the patient. Suitable delivery routes include, without limitation, intraparenchymal, intramuscular, intravenous, intracerebroventricular, subcutaneous, or intramucosal delivery.

Still another aspect of the present invention relates to a method of treating a neurological disease or disorder using the HSV amplicon particles of the present invention which include a transgene encoding a therapeutic transgene product. Basically, this method is carried out by providing such HSV amplicon particles and exposing patient neural or pre-neural cells to the HSV amplicon particles under conditions effective for infective transformation of neural or pre-neural cells of the patient, wherein the therapeutic tansgene product is expressed in vivo by the neural or pre-neural cells, thereby treating the neurological disease or disorder.

As noted above, transformation can be effected either in vivo or ex vivo (i.e., using differentiated neural cells, neural stem cells, or embryonic stem cells which differentiate into neural cells). A preferred in vivo route of delivery is administering the HSV amplicon particles directly to neural cells which are to be treated using, e.g., the delivery routes listed above.

Neuronal diseases or disorders which can be treated include lysosomal storage diseases (e.g., by expressing MPS 1-VIII, hexoaminidase A/B, etc.), Lesch-Nyhan syndrome (e.g., by expressing HPRT), amyloid polyneuropathy (e.g., by expressing β-amyloid converting enzyme (BACE) or amyloid antisense), Alzheimer's Disease (e.g., by expressing NGF, CHAT, BACE, etc.), retinoblastoma (e.g., by expressing pRB), Duchenne's muscular dystrophy (e.g., by expressing Dystrophin), Parkinson's Disease (e.g., by expressing GDNF, Bcl-2, TH, AADC, VMAT, antisense to mutant alpha-synuclein, etc.), Diffuse Lewy Body disease (e.g., by expressing heat shock proteins, parkin, or antisense or RNAi to alpha-synuclein), stroke (e.g., by expressing Bcl-2, HIF-DN, BMP7, GDNF, other growth factors), brain tumor (e.g., by expressing angiostatin, antisense VEGF, antisense or ribozyme to EGF or scatter factor, pro-apoptotic proteins), epilepsy (e.g., by expressing GAD65, GAD67, pro-apoptotic proteins into focus), or arteriovascular malformation (e.g., by expressing proapoptotic proteins).

Likewise, the HSV amplicon particles of the present invention which include a transgene encoding a therapeutic transgene product can also be used according to a method of inhibiting development of a neurological disease or disorder. Basically, this method is carried out by providing such HSV amplicon particles and exposing neural or pre-neural cells of the patient who is susceptible to development of a neurological disease or disorder to the HSV amplicon particles under conditions effective for infective transformation of the neural or pre-neural cells, wherein the therapeutic transgene product is expressed in vivo by the neural or pre-neural cells, thereby inhibiting development of the neurological disease or disorder.

As noted above, transformation can be effected either in vivo or ex vivo (i.e., using differentiated neural cells, neural stem cells, or embryonic stem cells which differentiate into neural cells). A preferred in vivo route of delivery is administering the HSV amplicon particles directly to the neural cells which are to be treated using, e.g., the delivery routes listed above. The neuronal disease or disorder whose development can be inhibited, and the therapeutic transgene product associated therewith, are those which are listed above by way of example.

In addition to the foregoing uses described, the HSV amplicon particles of the present invention can also be used for delivery of other therapeutic transgenes as reported previously in the literature (i.e., using other vectors or HSV-derived vectors prepared according to helper-virus procedures or previously reported helper virus-free procedures). By way of example, Kutubuddin et al., "Eradication of Pre-Established Lymphoma Using Herpes Simplex Virus Amplicon Vectors," *Blood* 93(2):643-654 (1999), which is hereby incorporated by reference in its entirety, reports on the use of helper virus-prepared HSV amplicon particles which transduce CD80 or RANTES, eliciting a protective immune response to pre-established lymphoma and generating tumor-specific cytotoxic T-cells immunity and immunologic memory.

EXAMPLES

The following examples are provided to illustrate an embodiment of the present invention but is by no means intended to limit its scope.

Materials & Methods

Cell Culture

Baby hamster kidney (BHK) cells were maintained as described before (Lu and Federoff, "Herpes simplex virus type 1 amplicon vectors with glucocorticoid-inducible gene expression," *Hum. Gene Ther.* 6:421-430 (1995), which is hereby incorporated by reference in its entirety). The NIH-3T3 mouse fibroblast cell line was originally obtained from American Type Culture Collection and maintained in Dulbecco's modified Eagle medium (MEM) supplemented with 10% fetal bovine serum (FBS), penicillin, and streptomycin.

Plasmid Construction

The HSVPrPUC/CMVegfp amplicon plasmid was constructed by cloning the 0.8-kb cytomegalovirus (CMV) immediate early promoter and 0.7-kb enhanced green fluorescent protein cDNA (Clontech, Inc.) into the BamHI restriction enzyme site of the pHSVPrPUC amplicon vector.

A 3.5 kb Hpa I/Hind III fragment encompassing the UL41 (vhs) open reading frame and its 5' and 3' transcriptional regulatory elements was removed from cos56 (Cunningham and Davison, "A cosmid-based system for construction mutants of herpes simplex type 1," *Virology*, 197:116-124 (1993), which is hereby incorporated by reference in its entirety) and cloned into pBSKSII (Stratagene, Inc.) to create pBSKS(vhs).

For construction of pGRE$_5$vp16, the VP16 coding sequence was amplified by PCR from pBAC-V2 using gene-specific oligonucleotides that possess EcoRI and HindIII restriction enzyme sequences that facilitates cloning into the pGRE$_5$-2 vector (Mader and White, "A steroid-inducible promoter for the controlled overexpression of cloned genes in eukaryotic cells," *Proc. Natl. Acad. Sci. USA*, 90:5603-5607 (1993), which is hereby incorporated by reference in its entirety). The oligonucleotide possessing the EcoRI site has a nucleotide sequence according to SEQ ID No: 6 as follows:

cggaattccg caggttttgt aatgtatgtg ctcgt    35

The oligonucleotide possessing the HindIII site has a nucleotide sequence according to SEQ ID No: 7 as follows:

ctccgaagct taagcccgat atcgtctttc ccgtatca    38

Helper Virus-Free Amplicon Packaging

On the day prior to transfection, 2×1⁶ BHK cells were seeded on a 60-mm culture dish and incubated overnight at 37° C. For cosmid-based packaging: The day of transfection, 250 µl Opti-MEM (Gibco-BRL, Bethesda, Md.), 0.4 µg of each of the five cosmid DNAs and 0.5 µg amplicon vector DNA with or without varying amounts of pBSKS(vhs) plasmid DNA were combined in a sterile polypropylene tube (Fraefel et al., "Helper virus-free transfer of herpes simplex virus type 1 plasmid vectors into neural cells," *J. Virol.* 70:7190-7197 (1996), which is hereby incorporated by reference in its entirety). For BAC-based packaging: 250 µl Opti-MEM (Gibco-BRL, Bethesda, Md.), 3.5 µg of pBAC-V2 DNA and 0.5 µg amplicon vector DNA with or without varying amounts of pBSKS(vhs) plasmid DNA were combined in a sterile polypropylene tube (Stavropoulos and Strathdee, "An enhanced packaging system for helper-dependent herpes simplex virus vectors," *J. Virol.*, 72:7137-43 (1998), which is hereby incorporated by reference in its entirety). The protocol for both cosmid- and BAC-based packaging was identical from the following step forward. Ten microliters of Lipofectamine Plus Reagent (Gibco-BRL) were added over a 30-second period to the DNA mix and allowed to incubate at RT for 20 min. In a separate tube, 15 µl Lipofectamine (Gibco-BRL) were mixed with 250 µl Opti-MEM. Following the 20-min incubation, the contents of the two tubes were combined over a 1-min period, and incubated for an additional 20 min at RT. During the second incubation, the medium in the seeded 60-mm dish was removed and replaced with 2 ml Opti-MEM. The transfection mix was added to the flask and allowed to incubate at 37° C. for 5 hrs. The transfection mix was then diluted with an equal volume of DMEM plus 20% FBS, 2% penicillin/streptomycin, and 2 mM hexamethylene bis-acetamide (HMBA), and incubated overnight at 34° C. The following day, medium was removed and replaced with DMEM plus 10% FBS, 1% penicillin/streptomycin, and 2 mM HMBA. The packaging flask was incubated an additional 3 days and virus harvested and stored at −80° C. until purification. Viral preparations were subsequently thawed, sonicated, and clarified by centrifugation (3000×g, 20 min.). Viral samples were stored at −80° C. until use. For packaging experiments examining the effect of VP16 on amplicon titers, the cells plated for packaging were first allowed to adhere to the 60-mm culture dish for 5 hours and subsequently transfected with pGRE₅vp16 using the Lipofectamine reagent as described above. Following a 5-hr incubation, the transfection mix was removed, complete medium (DMEM plus 10% FBS, 1% penicillin/streptomycin) was added, and the cultures were incubated at 37° C. until the packaging co-transfection step the subsequent day.

Viral Titering

Amplicon titers were determined by counting the number of cells expressing enhanced green fluorescent protein (HS-VPrPUC/CMVegfp amplicon) or β-galactosidase (HSVlac amplicon). Briefly, 10 µl of concentrated amplicon stock was incubated with confluent monolayers (2×10⁵ expressing particles) of NIH 3T3 cells plated on glass coverslips. Following a 48-hr incubation, cells were either fixed with 4% paraformaldehyde for 15 min at RT and mounted in Moiwol for fluorescence microscopy (eGFP visualization), or fixed with 1% glutaraldehyde and processed for X-gal histochemistry to detect the lacZ transgene product Fluorescent or X-gal-stained cells were enumerated, expression titer calculated, and represented as either green-forming units per ml (gfu/ml) or blue-forming units per ml (bfu/ml), respectively.

TaqMan Quantitative PCR System

To isolate total DNA for quantitation of amplicon genomes in packaged stocks, virions were lysed in 100 mM potassium phosphate pH 7.8 and 0.2% Triton X-100. Two micrograms of genomic carrier DNA was added to each sample. An equal volume of 2× Digestion Buffer (0.2 M NaCl, 20 mM Tris-Cl pH 8, 50 mM EDTA, 0.5% SDS, 0.2 mg/ml proteinase K) was added to the lysate and the sample was incubated at 56° C. for 4 hrs. Samples were processed further by one phenol:chloroform, one chloroform extraction, and a final ethanol precipitation. Total DNA was quantitated and 50 ng of DNA was analyzed in a PE7700 quantitative PCR reaction using a designed lacZ-specific primer/probe combination multiplexed with an 18S rRNA-specific primer/probe set. The lacZ probe sequence (SEQ ID No: 8) was as follows:

6FAM-accccgtacg tcttcccgag cg-TAMRA    22 where 6FAM is a (6-carboxyfluorescein) conjugated dye and TAMRA is a (6-carboxytetramethylrhodamine) conjugated quencher. The lacZ sense primer sequence (SEQ ID No: 9) was as follows:

gggatctgcc attgtcagac at    22

The lacZ antisense primer sequence (SEQ ID No: 10) was as follows:

tggtgtgggc cataattcaa    20

The 18S rRNA probe sequence (SEQ ID No: 11) was as follows:

JOE-tgctggcacc agacttgccc tc-TAMRA    22 where JOE is a (6-carboxy4',5'-dichloro-2',7'-dimethoxyfluorescein) conjugated dye. The 18S sense primer sequence (SEQ ID No: 12) was as follows:

cggctaccac atccaaggaa    20

The 18S antisense primer sequence (SEQ ID No: 13) was as follows:

gctggaatta ccgaggct    18

Each 25-µl PCR sample contained 2.5 µl (50 ng) of purified DNA, 900 nM of each primer, 50 nM of each probe, and 12.5 µl of 2× Perkin-Elmer Master Mix. Following a 2-min 50° C. incubation and 2-min 95° C. denaturation step, the samples were subjected to 40 cycles of 95° C. for 15 sec. and 60° C. for 1 min. Fluorescent intensity of each sample was detected automatically during the cycles by the Perkin-Elmer Applied Biosystem Sequence Detector 7700 machine. Each PCR run included the following: no-template control samples, positive control samples consisting of either amplicon DNA (for lacZ) or cellular genomic DNA (for 18S rRNA), and standard curve dilution series (for lacZ and 18S). Following the PCR run, "real-time" data were analyzed using Perkin-Elmer Sequence. Detector Software version 1.6.3 and the standard curves. Precise quantities of starting template were determined for each titering sample and results were expressed as numbers of vector genomes per ml of original viral stock.

Western Blot Analysis

BHK cell monolayers ($2\times10^6$ cells) transfected with varying packaging components were lysed with RIPA buffer (150 mM NaCl, 1% NP-40, 0.5% DOC, 0.5% SDS, and 50 mM Tris-Cl, pH 8). Equal amounts of protein were electrophoretically separated on a 10% SDS-PAGE gel and transferred to a PVDF membrane. The resultant blot was incubated with an anti-VP16 monoclonal antibody (Chemicon, Inc.), and specific VP16 immunoreactive band visualized using an alkaline phosphatase-based chemiluminescent detection kit (ECL).

Stereotactic Infections

Mice were anesthetized with Avertin at a dose of 0.6 ml per 25 g body weight. After positioning in an ASI murine stereotactic apparatus, the skull was exposed via a midline incision, and burr holes were drilled over the following coordinates (bregma, +0.5 mm; lateral −2.0 mm; and deep, −3.0 mm) to target infections to the striatum. A 33 GA steel needle was gradually advanced to the desired depth, and 3 µl of HSVPrPUC/CMVegfp virus was infused via a nicroprocessor-controlled pump over 10 minutes (UltraMicroPump, World Precision Instruments, Sarasota Springs, Fla.). The injector unit was mounted on a precision small animal stereotaxic frame (ASI Instruments, Warren, Mich.) micromanipulator at a 90° angle using a mount for the injector. Viral injections were performed at a constant rate of 300 nl/min. The needle was removed slowly over an additional 10-minute period.

Tissue Preparation and GFP Visualization

Infected mice were anesthetized four days later, a catheter was placed into the left ventricle, and intracardiac perfusion was initiated with 10 ml of heparinized saline (5,000 U/L saline) followed by 60 ml of chilled 4% PFA. Brains were extracted and postfixed for 1-2 hours in 4% PFA at 4° C. Subsequently, brains were cryoprotected in a series of sucrose solutions with a final solution consisting of a 30% sucrose concentration (w/v) in PBS. Forty micron serial sections were cut on a sliding microtome (Micron/Zeiss, Thomwood, N.Y.) and stored in a cryoprotective solution (30% sucrose (w/v), 30% ethylene glycol in 0.1 M phosphate buffer (pH 7.2)) at −20° C. until processed for GFP visualization. Sections were placed into Costar net wells (VWR, Springfield, N.J.) and incubated for 2 hrs in 0.1 M Tris buffered saline (TBS) (pH=7.6). Upon removal of cryoprotectant, two additional 10 min washes in 0.1 M TBS with 0.25% Triton X-100 (Sigma, St. Louis, Mo.) were performed. Sections were mounted with a fine paint brush onto subbed slides, allowed to air dry, and mounted with an aqueous mounting media, Mowiol. GFP-positive cells were visualized with a fluorescent microscope (Axioskop, Zeiss, Thornwood, N.Y.) utilizing a FITC cube (Chroma Filters, Brattleboro, Vt.). All images used for morphological analyses were digitally acquired with a 3-chip color CCD camera at 200× magnification (DXC-9000, Sony, Montvale, N.J.).

Morphological Analyses

Cell counts were performed on digital images acquired within 24 hrs of mounting. At the time of tissue processing coronal slices were stored serially in three separate compartments. All compartments were processed for cell counting and GFP(+) cell numbers reflect cell counts throughout the entire injection site. All spatial measurements were acquired using an image analysis program (Image-Pro Plus, Silver Spring, Md.) at a final magnification of 200×. Every section was analyzed using identical parameters in three different planes of focus throughout the section to prevent repeated scoring of GFP(+) cells. Each field was analyzed by a computer macro to count cells based on the following criteria: object area, image intensity (fluorescent signal) and plane of focus. Only cells in which the cell body was unequivocally GFP(+) and nucleus clearly defined were counted. Every section that contained a GFP-positive cell was counted. In addition, a watershed separation technique was applied to every plane of focus in each field to delineate overlapping cell bodies. The watershed method is an algorithm that is designed to erode objects until they disappear, then dilates them again such that they do not touch.

Example 1

Effect of Amplicon Co-Transfection With Vhs Vector

Figure 6A:
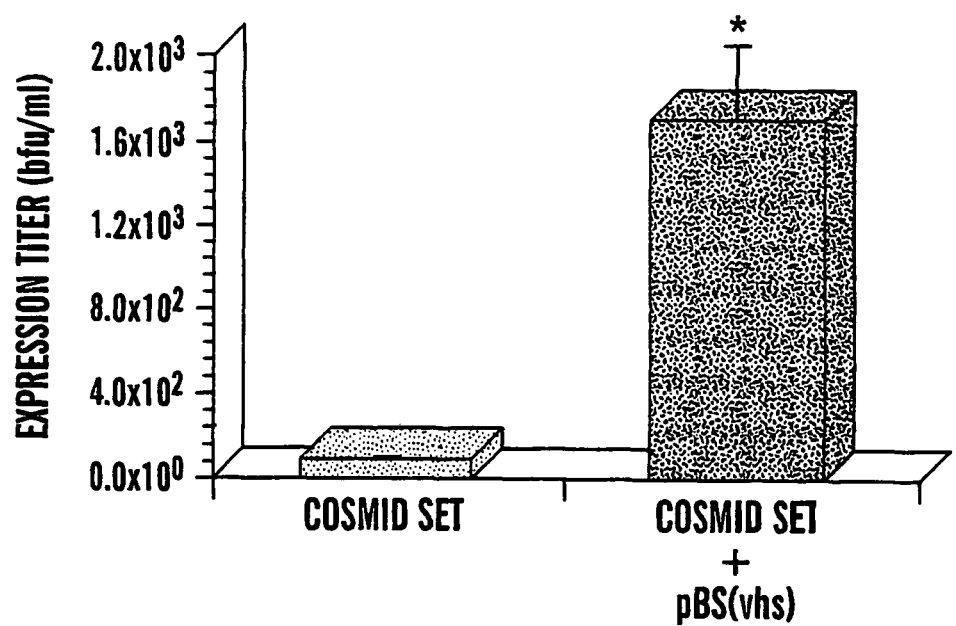
FIGS. 6A-B are graphs which illustrate the effect of vhs expression on helper virus-free amplicon packaging titers. The β-galactosidase-expressing (LacZ) HSV amplicon vector (HSVlac) was packaged in the absence or presence of pBS(vhs) by either the cosmid-(FIG. 6A) or BAC-based (FIG. 6B) helper virus-free production strategy. This pBS (vhs) plasmid possesses the vhs open reading frame as well as its entire 5' and 3' regulatory sequences. Amplicon stocks were harvested and used to transduce NIH 3T3 cells, and titers were determined one day later via enumeration of LacZ-positive cells. Titer data are expressed as blue-forming units per milliliter (bfu/ml) and error bars represent standard deviation.
Figure 6B:
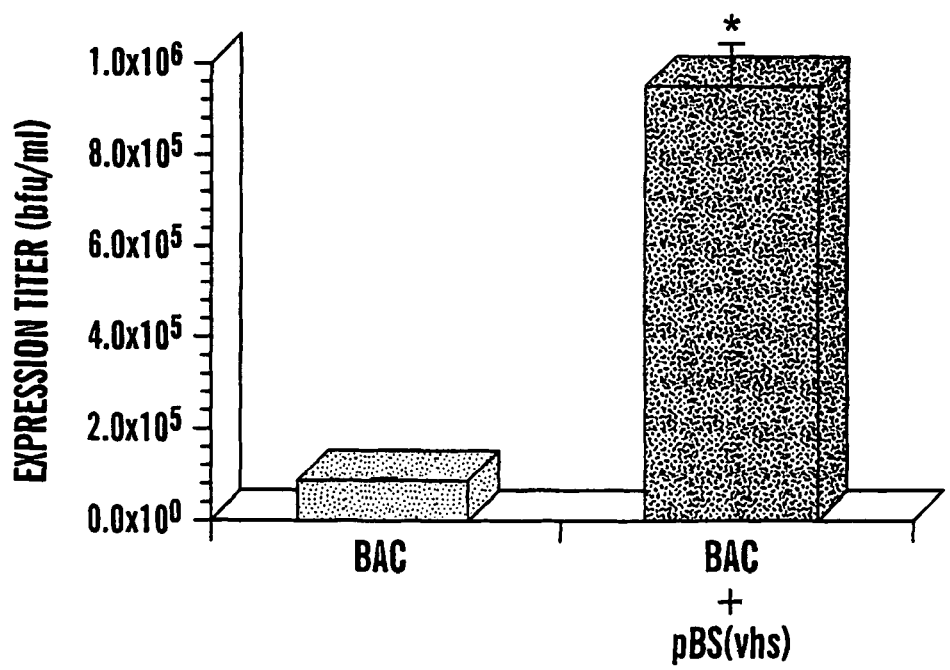

To determine if introduction of vhs into the packaging scheme could increase amplicon titers and quality, a genomic segment of the UL41 gene was cloned into pBluescript and the resulting plasmid (pBSKS(vhs)) was introduced into co-transfection protocols to provide vhs in trans. The genomic copy of UL41 contained the transcriptional regulatory region and flanking cis elements believed to confer native UL41 gene expression during packaging. When pBSKS(vhs) was added to the packaging protocols for production of a β-galactosidase (lacZ)-expressing amplicon (HSVlac), a maximum of 10-fold enhanced amplicon expression titers was observed for both cosmid- and BAC-based strategies (FIGS. 6A and B, respectively). As observed previously, the expression titers for HSVlac virus produced by the BAC-based method were approximately 500- to 1000-fold higher than stocks produced using the modified cosmid set. Even though a large disparity existed between the differently prepared stocks, the effect of additionally expressed vhs on amplicon titers was analogous.

Figure 7A:
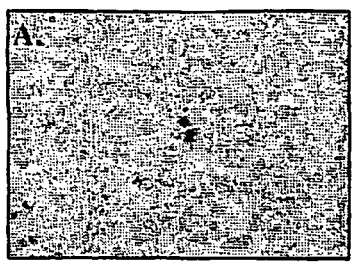
FIGS. 7A-G are images which illustrate the in vitro and in vivo analysis of vhs-mediated enhancement of helper-free amplicon titers. Ten microliters of BAC-packaged HSVlac produced without (FIG. 7A) or in the presence of pBS(vhs)
Figure 7B:
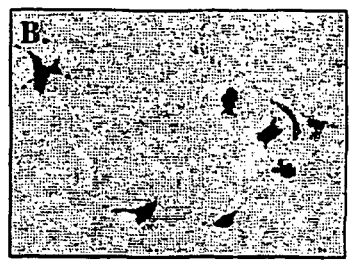
Figure 7C:
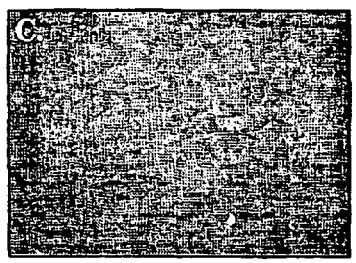
Figure 7D:

The punctate appearance of reporter gene product (pseudotransduction), a phenomenon associated with first-generation helper virus-free stocks, was drastically diminished in vitro when vhs was included in BAC-based packaging of an enhanced green fluorescent (GFP)-expressing virus (HSVPrPUC/CMVegfp) (FIGS. 7C-D). Pseudotransduction was not observed, as well, for cosmid-packaged amplicon stocks prepared in the presence of vhs.

Figure 7E:
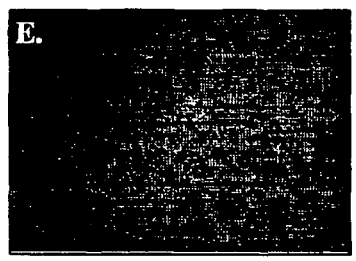
Figure 7F:
Figure 7G:
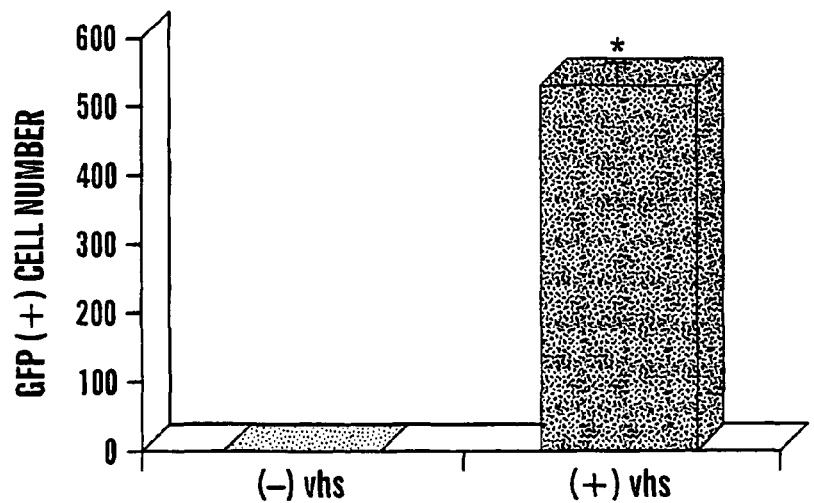

To assess the ability of the improved amplicon stocks to mediate gene delivery in vivo, 3 µl of BAC-packaged HSVPrPUC/CMVegfp virus prepared in the absence or presence of pBSKS(vhs) was injected stereotactically into the striata of C57BL/6 mice. Four days following infection, animals were sacrificed and analyzed for GFP-positive cells present in the striatum (FIGS. 7E-F). The numbers of cells transduced by HSVPrPUC/CMVegfp prepared in the presence of vhs were significantly higher than in animals injected with stocks produced in the absence of vhs (FIG. 7G). In fact, it was difficult to definitively identify GFP-positive cells in animals transduced with vhs(−) amplicon stocks.

The mechanism by which vhs expression resulted in higher apparent amplicon titers in helper virus-free packaging could be attributed to one or several properties of vhs. The UL41 gene product is a component of the viral tegument and could be implicated in structural integrity, and its absence could account for the appearance of punctate gene product material following transduction. For example, the viral particles may be unstable as a consequence of lacking vhs. Thus, physical conditions, such as repeated freeze-thaw cycles or long-term storage, may have led to inactivation or destruction of vhs-lacking virions at a faster rate than those containing vhs.

Figure 8A:
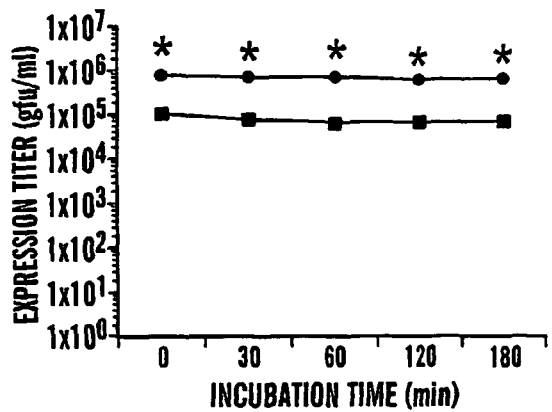
FIGS. 8A-D are graphs illustrating the effects of vhs presence during amplicon packaging on freeze/fracture stability and thermostability. BAC-packaged HSVPrPUC/CMVegfp stocks produced in the presence (circles) or absence (squares) of vhs were incubated at 0° C.
Figure 8B:
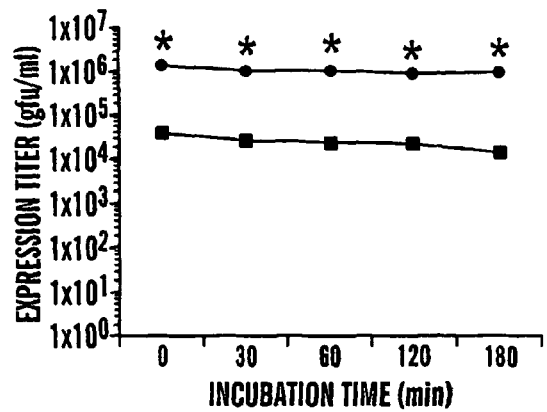
Figure 8C:
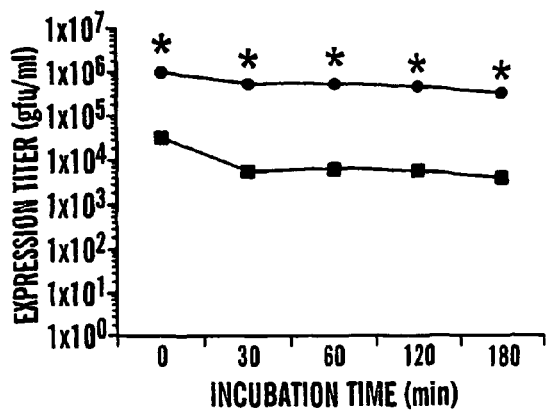
Figure 8D:
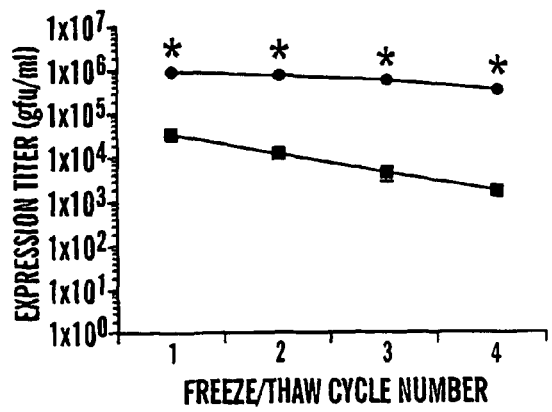

The stability of HSVPrPUC/CMVegfp packaged via the BAC method in the presence or absence of vhs was analyzed initially with a series of incubations at typically used experimental temperatures. Viral aliquots from prepared stocks of HSVPrPUC/CMVegfp were incubated at 4, 22, or 37° C. for periods up to three hours. Virus recovered at time points 0, 30, 60, 120, and 180 minutes were analyzed for their respective expression titer on NIH 3T3 cells. The rates of decline in viable amplicon particles, as judged by their ability to infect and express GFP, did not differ significantly between the vhs(+) and vhs(−) stocks (FIGS. 8A-C). Another condition that packaged amplicons encounter during experimental manipulation is freeze-thaw cycling. Repetitive freezing and thawing of virus stocks is known to diminish numbers of viable particles, and potentially the absence of vhs in the tegument of pBAC-V2 packaged amplicons leads to sensitivity to freeze fracture. To test this possibility, viral aliquots were exposed to a series of four freeze-thaw cycles. Following each cycle, samples were removed and titered for GFP expression on NIH 3T3 cells as described previously. At the conclusion of the fourth freeze-thaw cycle, the vhs(−) HSVPrPUC/CMVegfp stock exhibited a 10-fold diminution in expression titers as opposed to only a 2-fold decrease for vhs(+) stocks (FIG. 8D). This observation suggests that not only do vhs(+) stocks have increased expression titers, but the virions are more stable when exposed to temperature extremes, as determined by repetitive freeze-thaw cycling.

Wild-type HSV virions contain multiple regulatory proteins that prepare an infected host cell for virus propagation. One of these virally encoded regulators, which is localized to the tegument, is vhs. The UL41 gene-encoded vhs protein exhibits an essential endoribonucleolytic cleavage activity during lytic growth that destabilizes both cellular and viral mRNA species (Smibert et al., "Identification and characterization of the virion-induced host shutoff product of herpes simplex virus gene UL41," *J. Gen. Virol.*, 73:467-470 (1992), which is hereby incorporated by reference in its entirety). Vhs-mediated ribonucleolytic activity appears to prefer the 5' ends of mRNAs over 3' termini, and the activity is specific for mRNA, as vhs does not act upon ribosomal RNAs (Karr and Read, "The virion host shutoff function of herpes simplex virus degrades the 5' end of a target mRNA before the 3' end," *Virology*, 264:195-204 (1999), which is hereby incorporated by reference in its entirety). Vhs also serves a structural role in virus particle maturation as a component of the tegument HSV isolates that possess disruptions in UL41 demonstrate abnormal regulation of IE gene transcription and significantly lower titers than wild-type HSV-1 (Read and Frenkel, "Herpes simplex virus mutants defective in the virion-associated shutoff of host polypeptide synthesis and exhibiting abnormal synthesis of α (immediate early) viral polypeptides," *J. Virol.* 46:498-512 (1983), which is hereby incorporated by reference in its entirety), presumably due to the absence of vhs activity. Therefore, because vhs is essential for efficient production of viable wild-type HSV particles, it likely plays a similarly important role in packaging of HSV-1-derived amplicon vectors.

The term "pseudotransduction" refers to virion expression-independent transfer of biologically active vector-encoded gene product to target cells (Liu et al., "PseudotRansduction of hepatocytes by using concentrated pseudotyped vesicular stomatitis virus G glycoprotein (VSV-G)-Moloney murine leukemia virus-derived retrovirus vectors: comparison of VSV-G and amphotrophic vectors for hepatic gene transfer," *J. Virol.*, 70: 2497-2502 (1996); Alexander et al., "Transfer of contaminants in adeno-associated virus vector stocks can mimic transduction and lead to artifactual results," *Hum. Gene Ther.* 8:1911-1920 (1997); Yu et al., "High efficiency in vitro gene transfer into vascular tissues using a pseudotyped retroviral vector without pseudotransduction," *Gene Ther.*, 6:1876-1883 (1999), which are hereby incorporated by reference in their entirety). This phenomenon was originally described with retrovirus and adeno-associated virus vector stocks and was shown to result in an overestimation of gene transfer efficiencies. β-galactosidase and alkaline phosphatase are two commonly expressed reporter proteins that have been implicated in pseudotransduction, presumably due to their relatively high enzymatic stability and sensitivity of their respective detection assays (Alexander et al., "Transfer of contaminants in adeno-associated virus vector stocks can mimic transduction and lead to artifactual results," *Hum. Gene Ther.* 8:1911-1920 (1997), which is hereby incorporated by reference in its entirety). Stocks of β-galactosidase-expressing HSVlac and GFP-expressing HSVPrPUC/CMVegfp exhibited high levels of pseudotransduction when packaged in the absence of vhs. Upon addition of vhs to the previously described helper virus-free packaging protocols (Fraefel et al., "Helper virus-free transfer of herpes simplex virus type 1 plasmid vectors into neural cells," *J. Virol.* 70:7190-7197 (1996); Stavropoulos and Strathdee, "An enhanced packaging system for helper-dependent herpes simplex virus vectors," *J. Virol.*, 72:7137-43 (1998), which are hereby incorporated by reference in their entirety), a 10-fold increase in expression titers and concomitant decrease in pseudotransduction were observed in vitro.

Vhs-mediated enhancement of HSV amplicon packaging was even more evident when stocks were examined in vivo. GFP-expressing cells in animals transduced with vhs(+) stocks were several hundred-fold greater in number than in animals receiving vhs(−) stocks. This could have been due to differences in virion stability, where decreased particle stability could have led to release of co-packaged reporter gene product observed in the case of vhs(−) stocks. Additionally, the absence of vhs may have resulted in packaging of reporter gene product into particles that consist of only tegument and envelope (Rixon et al., "Assembly of enveloped tegument structures (L particles) can occur independently of virion maturation in herpes simplex virus type 1-infected cells," *J. Gen. Virol.*, 73:277-284 (1992), which is hereby incorporated by reference in its entirety). Release of co-packaged reporter gene product in either case could potentially activate a vigorous immune response in the CNS, resulting in much lower than expected numbers of vector-expressing cells.

Interestingly, the HSV-encoding cosmid set harbored an intact UL41 gene locus (Cunningham and Davison, "A cosmid-based system for construction mutants of herpes simplex type 1," *Virology* 197:116-124 (1993), which is hereby incorporated by reference), while the BAC reagent that was utilized for helper virus-free packaging did not because of a disruption introduced during its initial construction (Stavropoulos and Strathdee, "An enhanced packaging system for helper-dependent herpes simplex virus vectors," *J. Virol.*, 72:713743 (1998), which is hereby incorporated by reference). Expression of vhs via a co-transfected plasmid containing the entire UL41 gene plus its cognate transcriptional regulatory regions resulted in pronounced increases in packaged amplicon produced via either cosmid- or BAC-based method. For BAC-based packaging, the explanation appears rather clear: vhs is not expressed due to disruption of the UL41 locus, and therefore, inclusion of a vhs expression plasmid results in a more productive packaging. In the case for cosmid-based packaging, the copy number of the co-transfected vhs-encoding plasmid greatly exceeded the number of vhs transcription units present in the cosmid set. This likely led to a more rapid accumulation of vhs during the early stages of packaging. Additionally, because the cosmid set is believed to undergo recombination of its overlapping homologous regions to produce a HSV genome-sized unit following introduction into the packaging cell, perhaps viral gene expression is delayed (Cunningham and Davison, "A cosmid-based system for construction mutants of herpes simplex type 1," *Virology*, 197:116-124 (1993), which is hereby incorporated by reference). As a result, amplicon propagation cannot optimally initiate.

Figure 13:
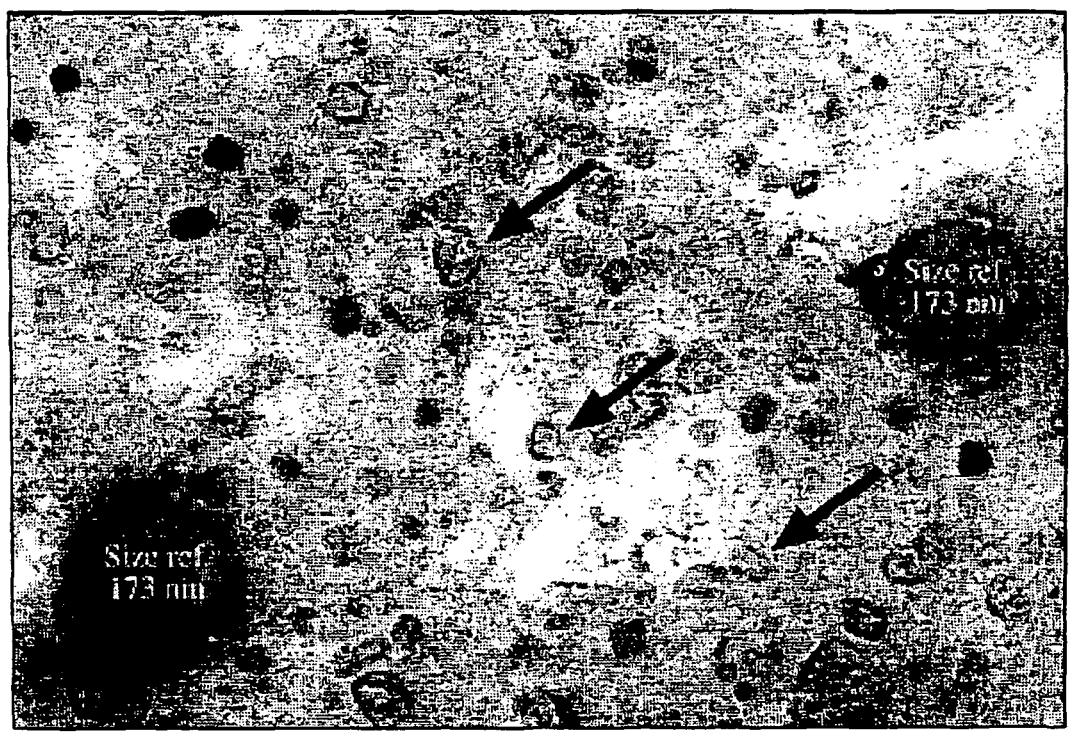
FIG. 13 is a scanning electron micrograph image of purified helper-virus free HSV-1 amplicon virion stocks prepared using a negative staining technique. Arrows denote individual amplicon particles.

The resulting HSV amplicon particles were also examined by scanning electron micrography using a standard negative staining technique (Monroe and Brandt, "Rapid semiquantitative method for screening large numbers of virus samples by negative staining electron microscopy," Appl Microbiol 20(2):259-62 (1970), which is hereby incorporated by reference in its entirety). As shown in FIG. 13, the HSV amplicon particles, denoted by arrows, are substantially smaller in size than the 173 nm reference spheres and rather heterogeneous in structure. In contrast, helper virus-containing stocks are characterized by the production of HSV amplicon particles which are approximately 150 nm in size and more homogeneous in shape. Thus, the HSV amplicon particles of the present invention are physically different from previously known helper virus-prepared HSV amplicon particles.

Example 2

Effect of VP16 Expression in Host Cells Prior to Amplicon Co-Transfection

The native HSV genome enters the host cell with several viral proteins besides vhs, including the strong transcriptional activator VP16. Once within the cell, VP16 interacts with cellular transcription factors and HSV genome to initiate immediate-early gene transcription. Under helper virus-free conditions, transcriptional initiation of immediate-early gene expression from the HSV genome may not occur optimally, thus leading to lower than expected titers. To address this issue, a VP16 expression construct was introduced into packaging cells prior to cosmid/BAC, amplicon, and pBSKS(vhs) DNAs, and resultant amplicon titers were measured. To achieve regulated expression a glucocorticoid-controlled VP16 expression vector was used (pGRE$_5$vp16).

Figure 9A:
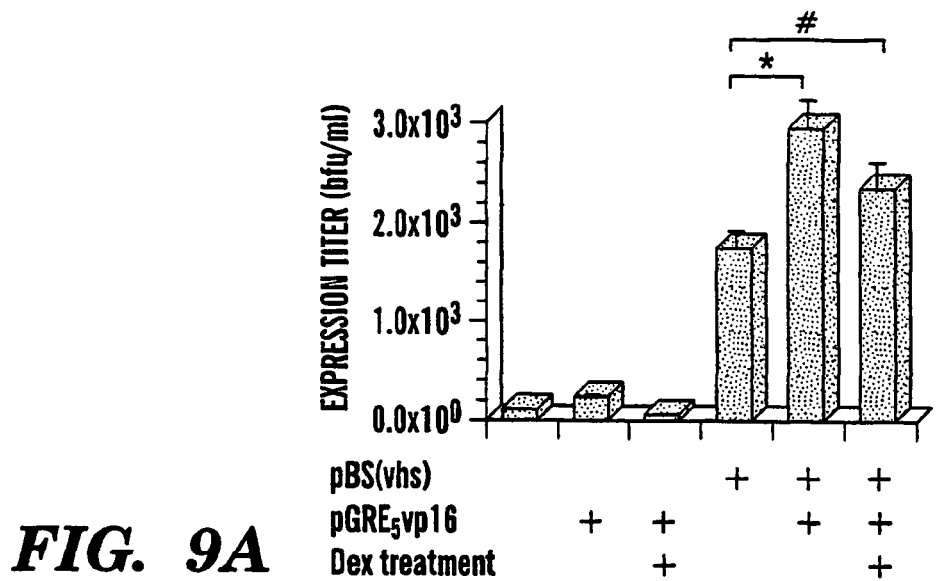
FIGS. 9A-C illustrate the effect of the pre-loading of packaging cells with VP16 on enhancement of amplicon expression titers only in presence of vhs. BHK cells were plated and 6 hours later, were transfected with a glucocorticoid-regulated VP16 expression vector (pGRE$_5$vp16). A subset of cultures received 100 nM dexamethasone following the VP16 plasmid transfection. The following day, HSVlac, a β-galactosidase-expressing amplicon, was cosmid-(FIG. 9A) or BAC-packaged (FIG. 9B) in the absence or presence of the pBS(vhs) plasmid using the modified BHK cultures. Resultant amplicon stocks were titered on NIH 3T3 cells using X-gal histochemistry and titers represented as blue-forming units per milliliter (bfu/ml.
Figure 9B:
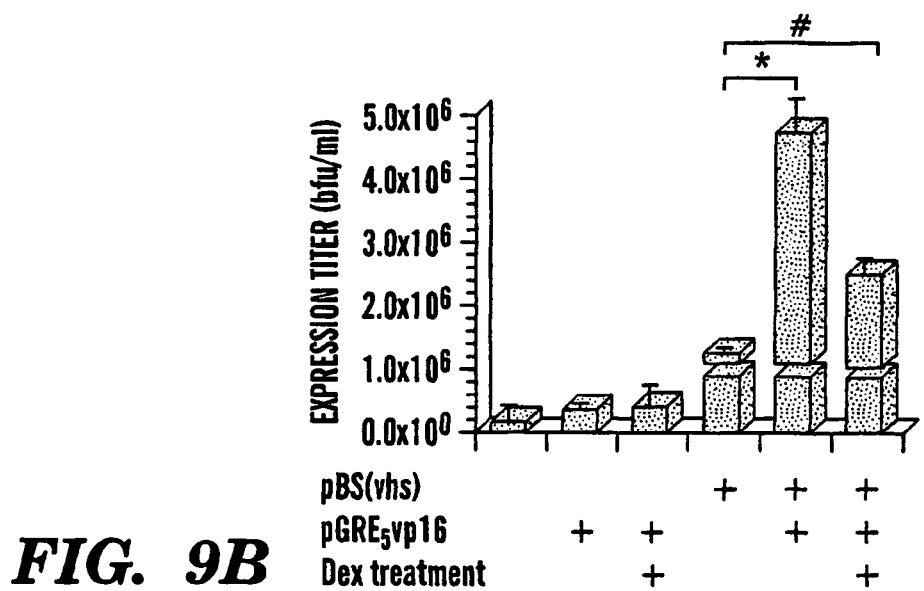
Figure 9C:
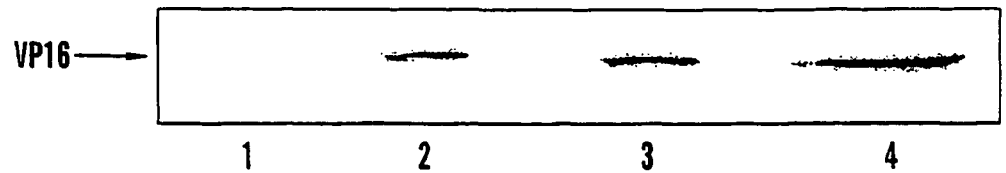

The pGRE$_5$vp16 vector was introduced into the packaging cells 24 hours prior to transfection of the regular packaging DNAs. HSVlac was packaged in the presence or absence of vhs and/or VP16 and resultant amplicon stocks were assessed for expression titer. Some packaging cultures received 100 nM dexamethasone at the time of pGRE$_5$vp16 transfection to strongly induce VP16 expression; others received no dexamethasone. Introduction of pGRE$_5$vp16 in an uninduced (basal levels) or induced state (100 nM dexamethasone) had no effect on HSVlac titers when vhs was absent from the cosmid- or BAC-based protocol (FIGS. 9A-B). In the presence of vhs, addition of pGRE$_5$vp16 led to either a two- or five-fold enhancement of expression titers over those of stocks packaged with only vhs (cosmid- and BAC-derived stocks, respectively; FIGS. 9A-B). The effect of "uninduced" pGRE$_5$vp16 on expression titers suggested that VP16 expression was occurring in the absence of dexamethasone. To demonstrate this, Western blot analysis with a VP16-specific monoclonal antibody was performed using lysates prepared from BHK cells transfected with the various packaging components. Cultures transfected with pGRE$_5$vp16/BAC/pBSKS(vhs) in the absence of dexamethasone did show VP16 levels intermediate to cultures transfected either with BAC alone (lowest) or those transfected with pGRE$_5$vp16/BAC/pBSKS(vhs) in the presence of 100 nM dexamethasone (highest)(FIG. 9C).

Figure 10:
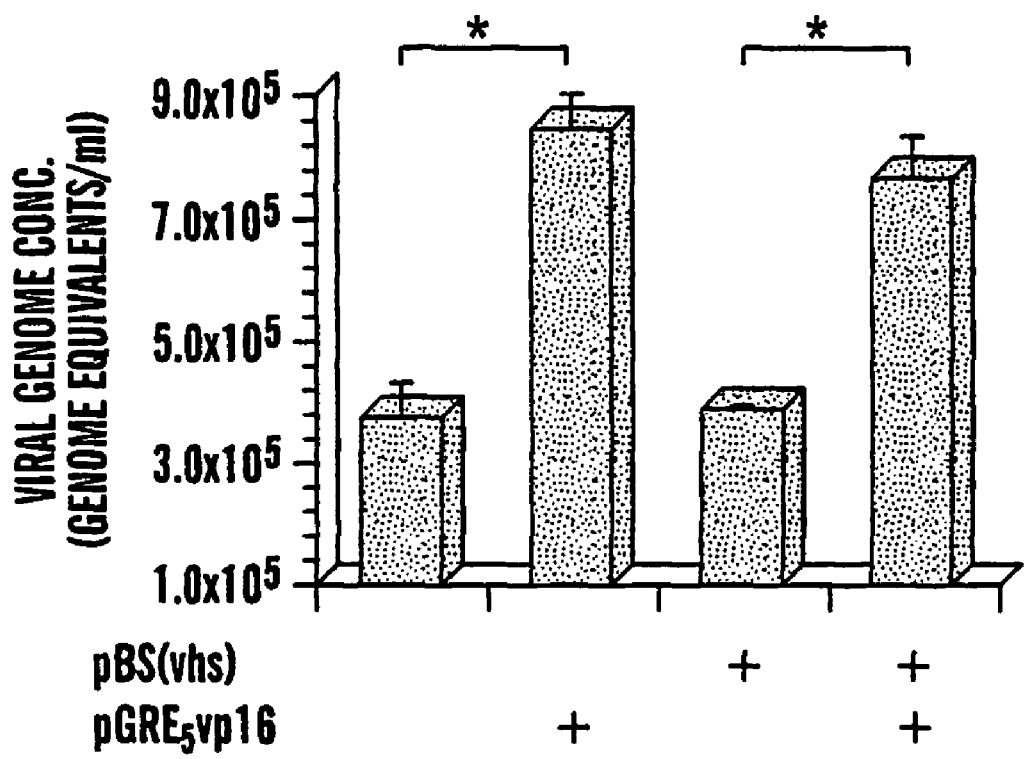
FIG. 10 is a graph illustrating that the virion-incorporated amplicon genome levels are enhanced by ectopic expression of VP16. BAC-packaged HSVlac stocks prepared in the presence or absence of VP16 and/or vhs were analyzed for levels of genome content using a "real-time" quantitative PCR technique. Nanogram quantities of vector genome were assayed for each sample and data were expressed as detected amplicon genome per milliliter. Error bars represent standard deviation.
Figure 11:
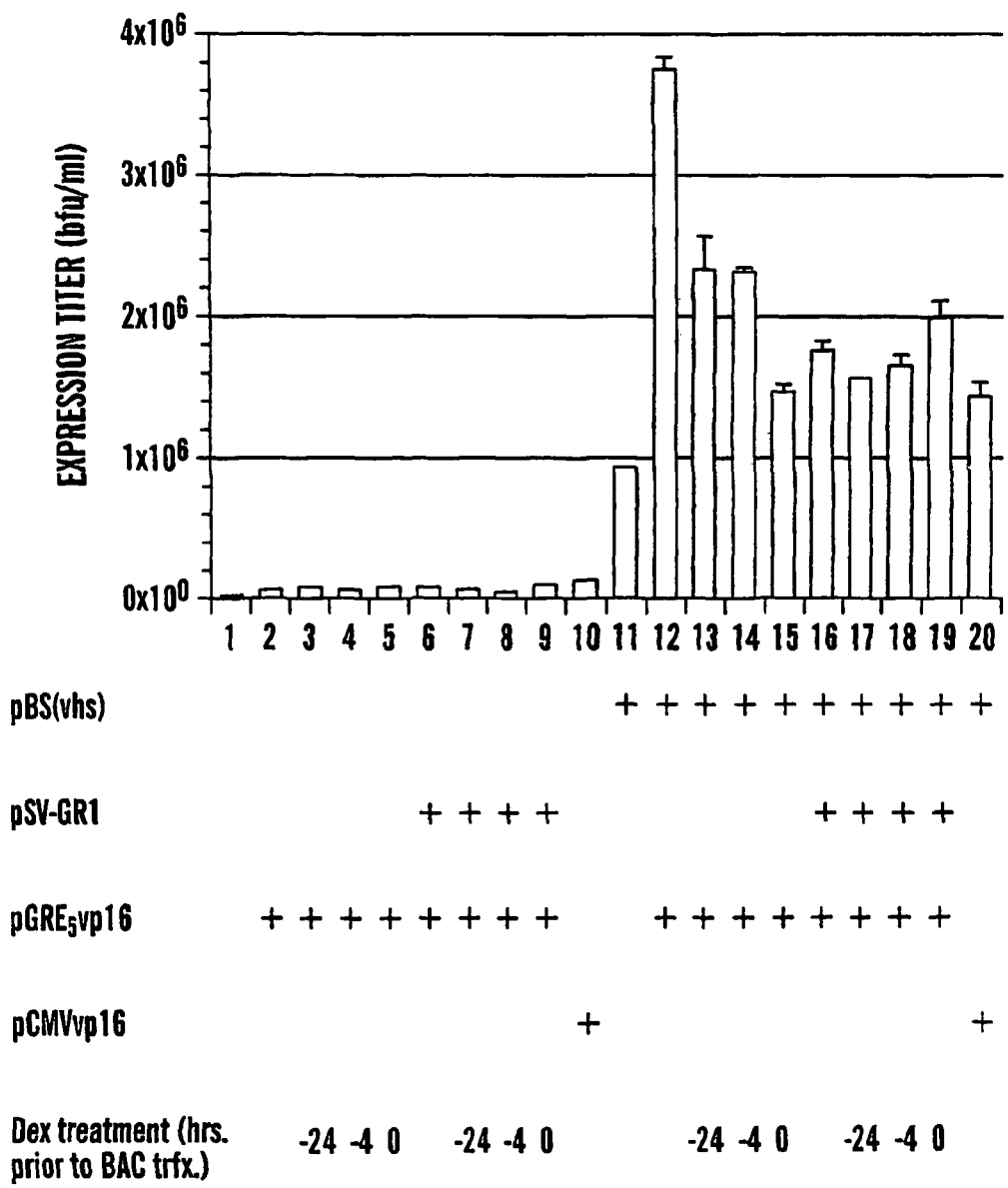
FIG. 11 is a graph illustrating the virion-incorporated amplicon genome levels are enhanced by ectopic expression of VP16. BAC-packaged HSVlac stocks prepared in the presence or absence of VP16 and/or vhs were analyzed for amplicon titer (bfu/ml) using a "real-time" analysis. Error bars represent standard deviation.

VP16-mediated enhancement of packaged amplicon expression titers could be due to increased DNA replication and packaging of amplicon genomes. Conversely, the additional VP16 that is expressed via pGRE$_5$vp16 could be incorporated into virions and act by increasing vector-directed expression in transduced cells. To test the possibility that VP16 is acting by increasing replication in the packaging cells, concentrations of vector genomes in BAC-derived vector stocks were determined. HSVlac stocks produced in the presence or absence of vhs and/or VP16 were analyzed using a "real-time" quantitative PCR method. The concentration of vector genome was increased two-fold in stocks prepared in the presence of VP16 and this increase was unaffected by the presence of vhs (FIG. 10). VP16 expression was induced with 100 nM dexamethasone treatment at varying time points prior to introduction of the packaging components. Dexamethasone-induced production of VP16 prior to transfection of the packaging components did not appear to enhance amplicon titers over that observed with basal pGRE$_5$vp16-mediated expression (FIG. 11). This suggests that low levels of VP16 are sufficient to enhance amplicon packaging in the presence of vhs.

Pre-loading of packaging cells with low levels of the potent HSV transcriptional activator VP16 led to a 2- to 5-fold additional increase in amplicon expression titers only in the presence of vhs for cosmid- and BAC-based packaging systems, respectively. This observation indicates the transactivation and structural functions of VP16 were not sufficient to increase viable viral particle production when vhs was absent, and most likely led to generation of incomplete virions containing amplicon genomes as detected by quantitative PCR. When vhs was present for viral assembly, however, VP16-mediated enhancement of genome replication led to higher numbers of viable particles formed. The effect of VP16 on expression titers was not specific to amplicons possessing the immediate-early 4/5 promoter of HSV, as amplicons with other promoters were packaged to similar titers in the presence of VP16 and vhs.

VP16 is a strong transactivator protein and structural component of the HSV virion (Post et al., "Regulation of alpha genes of herpes simplex virus: expression of chimeric genes produced by fusion of thymidine kinase with alpha gene promoters," *Cell*, 24:555-565 (1981), which is hereby incorporated by reference). VP16-mediated transcriptional activation occurs via interaction of VP16 and two cellular factors, Oct-1 (O'Hare and Goding, "Herpes simplex virus regulatory elements and the immunoglobulin octamer domain bind a common factor and are both targets for virion transactivation," *Cell*, 52:435-445 (1988); Preston et al., "A complex formed between cell components and an HSV structural polypeptide binds to a viral immediate early gene regulatory DNA sequence," *Cell*, 52:425-434 (1988); Stern et al., "The Oct-1 homoeodomain directs formation of a multiprotein-DNA complex with the HSV transactivator VP16," *Nature*. 341:624-630 (1989), which are hereby incorporated by reference in their entirety) and HCF (Wilson et al., "The VP16 accessory protein HCF is a family of polypeptides processed from a large precursor protein," *Cell* 74:115-125 (1993); Xiao and Capone, "A cellular factor binds to the herpes simplex virus type 1 transactivator Vmw65 and is required for Vmw65-dependent protein-DNA complex assembly with Oct-1," *Mol. Cell Biol.*, 10:4974-4977 (1990), which are hereby incorporated by reference in their entirety), and subsequent binding of the complex to TAATGARAT elements found within HSV IE promoter regions (O'Hare, "The virion transactivator of herpes simplex virus," *Semin. Virol.* 4:145-155 (1993), which is hereby incorporated by reference). This interaction results in robust up-regulation of IE gene expression. Neuronal splice-variants of the related Oct-2 transcription factor have been shown to block IE gene activation via binding to TAATGARAT elements (Lillycrop et al., "The octamer-binding protein Oct-2 represses HSV immediate-early genes in cell lines derived from latently injectable sensory neurons," *Neuron,* 7:381-390 (1991), which is hereby incorporated by reference), suggesting that cellular transcription factors may also play a role in limiting HSV lytic growth.

The levels of VP16 appear to be important in determining its effect on expression titers. Low, basal levels of VP16 (via uninduced $pGRE_5vp16$) present in the packaging cell prior to introduction of the packaging components induced the largest effect on amplicon expression titers. Conversely, higher expression of VP16 (via dexamethasone-induced $pGRE_5vp16$) did not enhance virus production to the same degree and may have, in fact, abrogated the process. The presence of glucocorticoids in the serum components of growth medium is the most likely reason for this low-level VP16 expression, as charcoal-stripped sera significantly reduces basal expression from this construct. Perhaps only a low level or short burst of VP16 is required to initiate IE gene transcription, but excessive VP16 leads to disruption of the temporal progression through the HSV lytic cycle, possibly via inhibition of vhs activity. Moreover, evidence has arisen to suggest vhs activity is downregulated by newly synthesized VP16 during the HSV lytic cycle, thereby allowing for accumulation of viral mRNAs after host transcripts have been degraded (Smibert et al., "Herpes simplex virus VP16 forms a complex with the virion host shutoff protein vhs," *J. Virol.* 68(4):233-236 (1994); Lam et al., "Herpes simplex virus VP16 rescues viral mRNA from destruction by the virion host shutoff function," *EMBO J.,* 15:2575-2581 (1996), which are hereby incorporated by reference in their entirety). Therefore, a delicate regulatory protein balance may be required to attain optimal infectious particle propagation. Additionally, the 100-nM dexamethasone treatment used to induce VP16 expression may have a deleterious effect on cellular gene activity and/or interfere with replication of the OriS-containing amplicon genome in packaging cells. High levels of dexamethasone have been shown previously to repress HSV-1 OriS-dependent replication by an unknown mechanism (Hardwicke and Schaffer, "Differential effects of nerve growth factor and dexamethasone on herpes simplex virus type 1 oriL- and oriS-dependent DNA replication in PC12 cells," *J. Virol.,* 71:3580-3587 (1997), which is hereby incorporated by reference in its entirety).

Example 3

Examination of Amplicon Cytotoxicity

Figure 12:
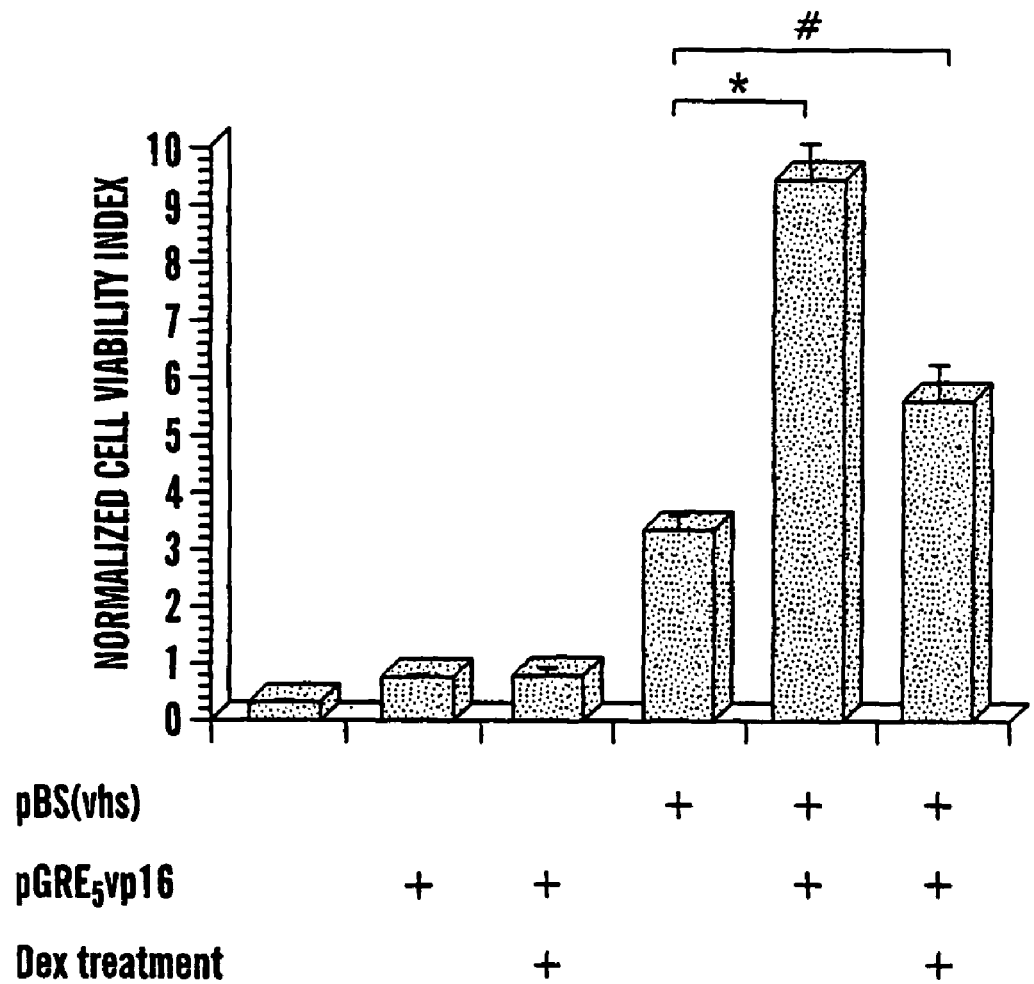
FIG. 12 is a graph illustrating that amplicon stock-mediated cytotoxicity is not increased by additional expression of vhs and VP16 during packaging. BAC-packaged HSVlac stocks prepared in the presence or absence of VP16 and/or vhs were analyzed on confluent monolayers of NIH 3T3 cells for elicited cytotoxicity as determined by an LDH release-based assay. Two of the packaging samples that received pGRE$_5$vp16 were also treated with 100 nM dexamethasone 24 hours prior to the packaging transfection. Equivalent expression units of virus from each packaging sample were used in the transductions. Viability data were represented as normalized cell viability index.

There is a possibility that addition of viral proteins, like vhs and VP16, to the packaging process may lead to vector stocks that are inherently more cytotoxic. The amplicon stocks described above were examined for cytotoxicity using a lactate dehydrogenase (LDH) release-based cell viability assay. Packaged amplicon stocks were used to transduce NIH 3T3 cells and 48 hours following infection, viability of the cell monolayers was assessed by the LDH-release assay. Amplicon stocks produced in the presence of vhs and VP16 displayed less cytotoxicity on a per virion basis than stocks packaged using the previously published BAC-based protocol (FIG. 12) (Stavropoulos and Strathdee, "An enhanced packaging system for helper-dependent herpes simplex virus vectors," *J. Virol.,* 72:7137-43 (1998), which is hereby incorporated by reference in its entirety)).

Ectopic expression of vhs and VP16 did not lead to amplicon stocks that exhibited higher cytotoxicity than helper virus-free stocks prepared in the traditional manner when examined by an LDH-release assay. Stocks prepared by the various methods were equilibrated to identical expression titers prior to exposure to cells. The heightened cytotoxicity in stocks produced in the absence of vhs and/or VP16 may reflect that larger volumes of these stocks were required to obtain similar expression titers as the vhs/VP16-containing samples or the levels of defective particles in the former may be significantly higher. Contaminating cellular proteins that co-purify with the amplicon particles are most likely higher in concentration in the traditional stocks, and probably impart the higher toxicity profiles observed.

Example 4

Comparative Analysis of Helper Virus-Free HSV Amplicon Particles and Helper Virus HSV Amplicon Particles Helper virus-free HSV amplicon particles were prepared as described above in Example 1 and helper virus-containing HSV amplicon particles were prepared according to known procedures.

Figure 14:
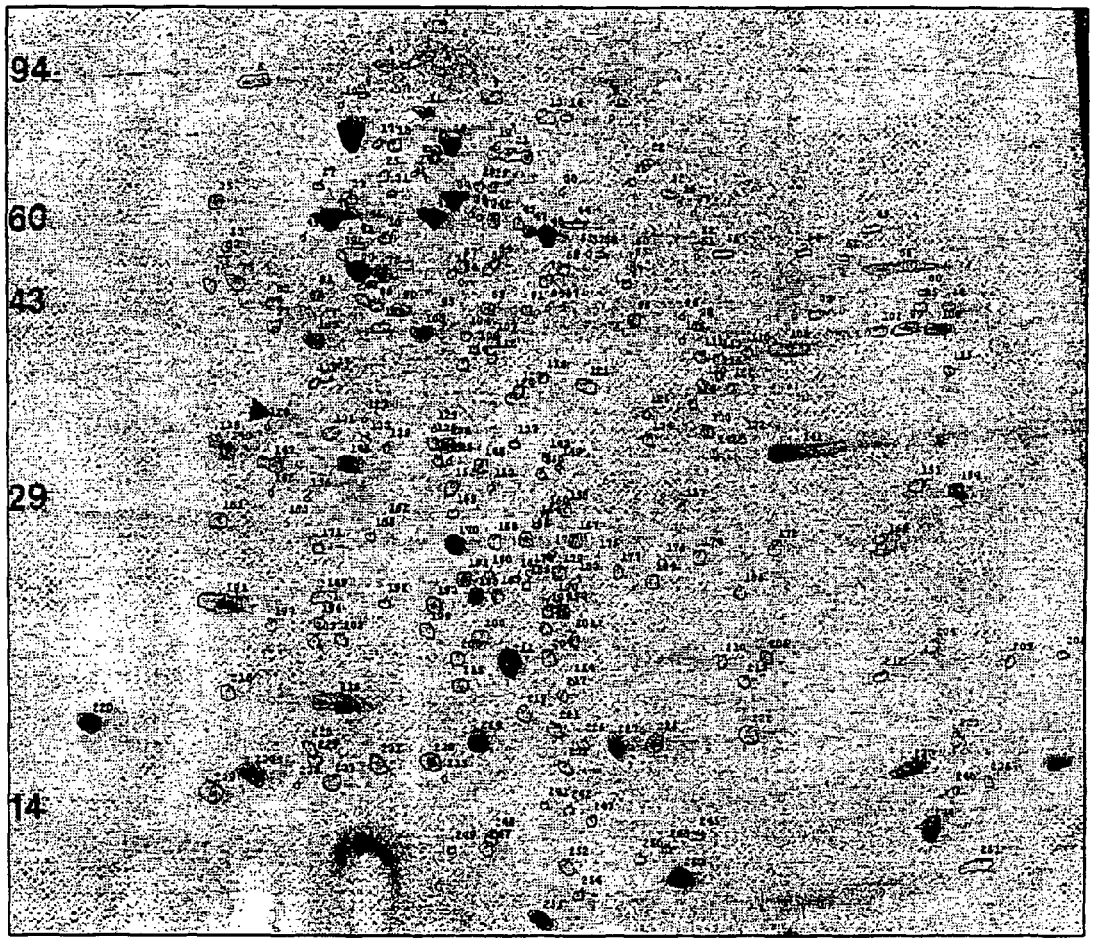
FIG. 14 is an image of a two-dimension gel for polypeptide analysis of virion particle stock prepared using helper virus-free procedure according to the present invention. Individual spots have been numbered. See Table 2, Example 4, for spot numbering and measurements.
Figure 15:
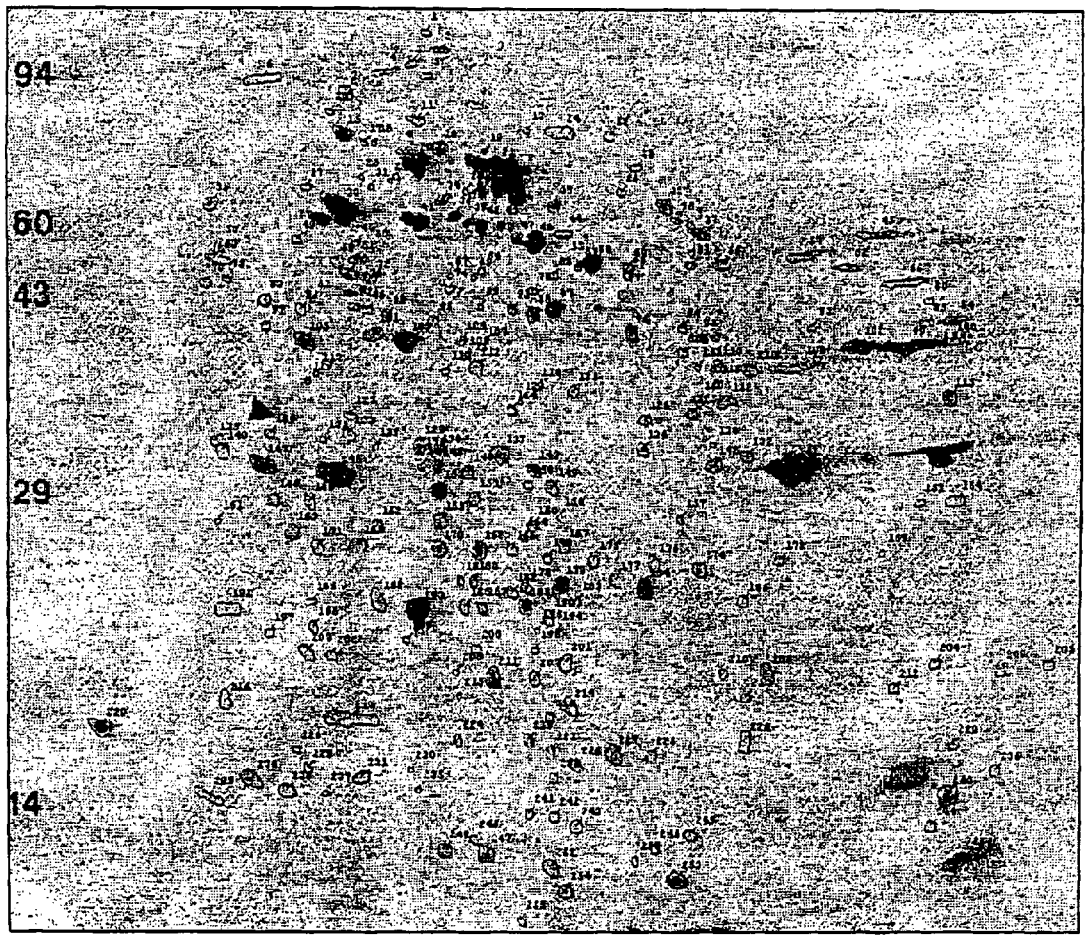
FIG. 15 is an image of a two-dimension gel for polypeptide analysis of virion particle stock prepared using helper virus procedure which is known in the art. Individual spots have been numbered. See Table 2, Example 4, for spot numbering and measurements.
Figure 16A:
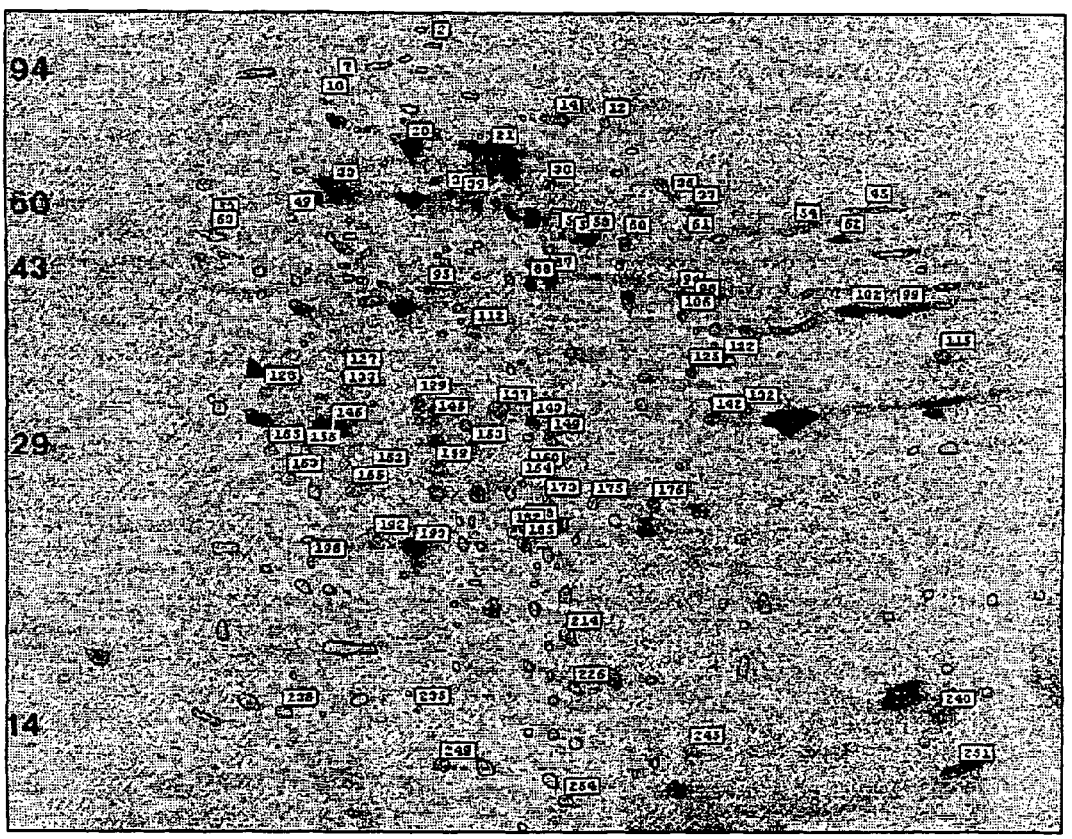
FIGS. 16A-B are difference images of gels shown in FIGS. 14 and 15, showing spots which are increased in FIG. 15 as compared to FIG. 14.
Figure 16B:
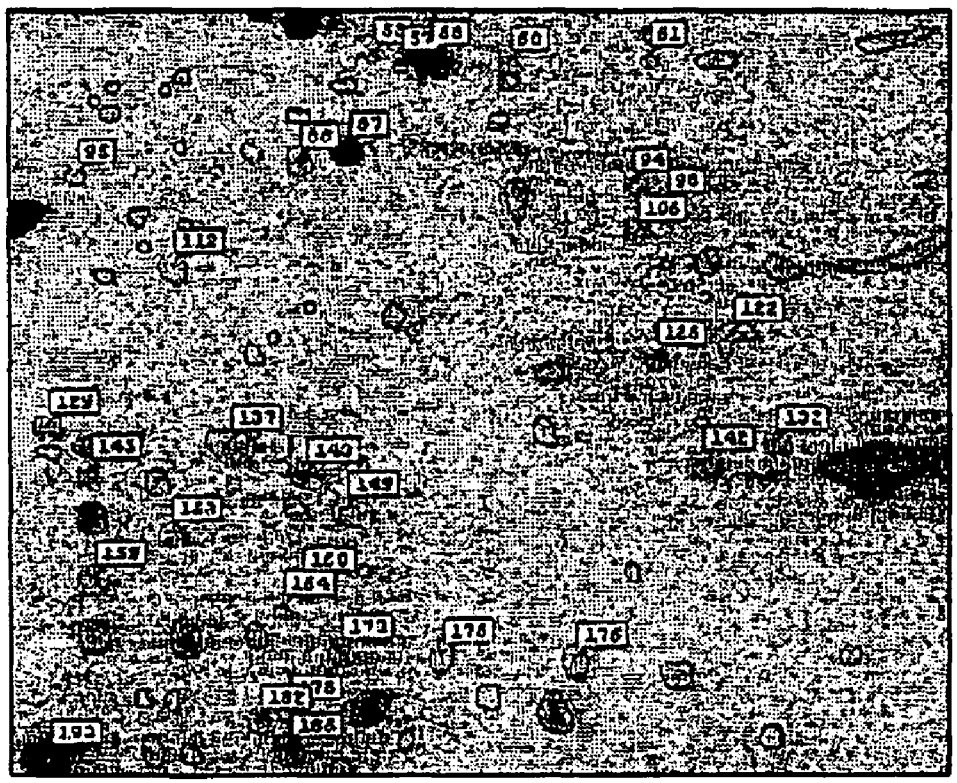
Figure 17A:
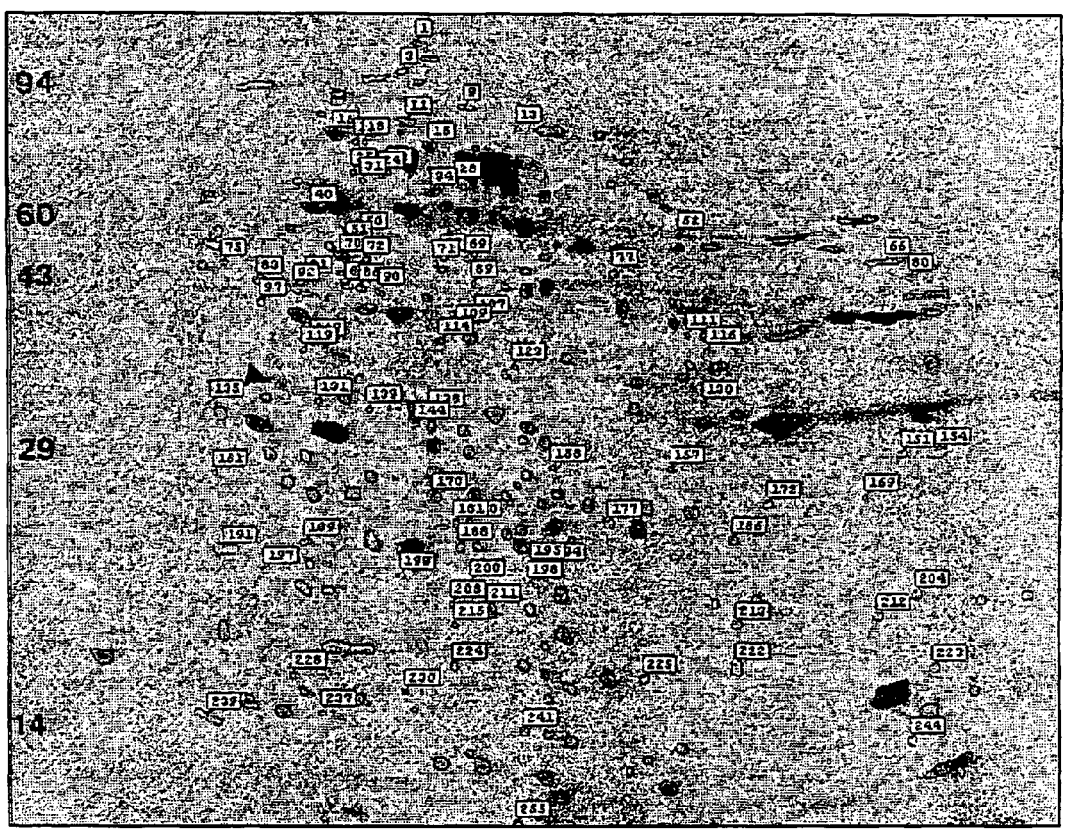
FIGS. 17A-C are difference images of gels shown in FIGS. 14 and 15, showing spots which are decreased in FIG. 15 as compared to FIG. 14.
Figure 17B:
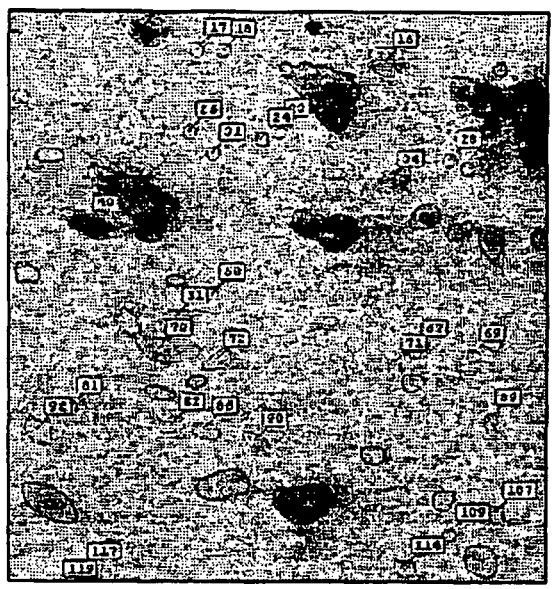
Figure 17C:
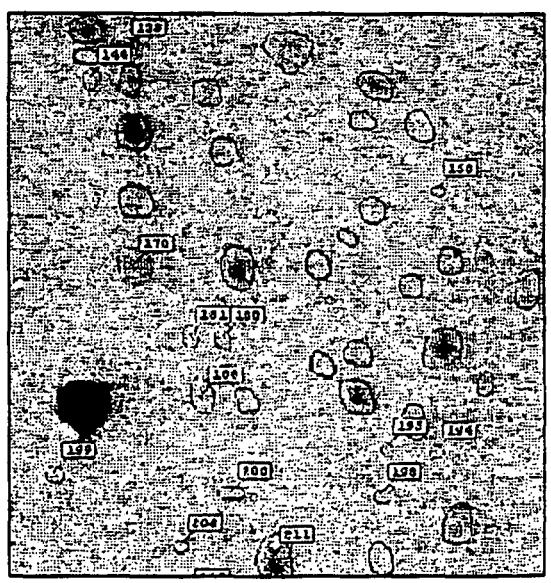

Two-dimensional gel analyses were performed on stocks containing the helper virus-free (HVF) virion particles (FIG. 14) and helper virus-containing (HVC) virion particles (FIG. 15) to determine differences in their protein composition. Virion particles from both helper virus-containing and helper virus-free amplicon stocks were purified by ultracentrifugation on a 30%/60% discontinuous sucrose gradient. Bands containing viral particles were extracted from the gradient at the 30%/60% interface and stored at −80° C. until 2-D gel analyses were performed. Prior to gel analyses, protein concentration was determined by the Bradford assay and 100 μg of each sample was resuspended in urea sample buffer (9.5 M ultrapure urea, 2% w/v Nonidet P-40, 5% beta-mercaptoethanol, and 2% ampholines consisting of 1.6% pH 5-7 and 0.4% pH 3.5-10). Fifty μg of each sample was run 2X's on 2-D gels (ampholines pH of 3.5-10), the gels were silver-stained, digitized, and analyzed by comparison of 2-D patterns and spot intensity of helper virus-containing vs. helper virus-free amplicon stocks.

As shown in Table 2 below, the reference spot number, pI, and molecular weight (daltons) are given for polypeptide spots analyzed in the samples obtained from the stocks of HVF and HVC virion particles. Also indicated in Table 2 are the fold increase or decrease (difference) of the polypeptides for gel bands from the two samples. Spot percentages were calculated as individual spot density divided by total density of all measured spots. The difference is calculated from spot density as follows:

$$\text{Difference} = \frac{(1 - \text{Spot Percentage of } HVC)}{(\text{Spot Percentage of } HVF)} \times -100$$

A significant increase in the polypeptide spot density is considered to be a difference ≧+300, where a significant decrease in the polypeptide spot density is considered to be a difference ≦−67. Significantly increased and decreased polypeptide spots are highlighted (outlined) in FIGS. 16A-B and 17A-C, respectively.

TABLE 2

Summary of Two-Dimensional Gel Protein Analysis

| Spot No. | pI | MW | Helper Virus-Free Spot Percent | Helper Virus-Containing Spot Percent | Difference |
|---|---|---|---|---|---|
| 1 | 6.04 | 150,730 | 0.24 | 0.05 | −79 |
| 2 | 6.14 | 121,290 | 0.02 | 0.09 | 341 |
| 3 | 5.94 | 103,956 | 0.61 | 0.01 | −99 |
| 4 | 5.74 | 96,220 | 0.34 | 0.17 | −49 |
| 5 | 6.02 | 93,124 | 0.07 | 0.03 | −55 |
| 6 | 5.1 | 92,212 | 0.71 | 0.36 | −49 |
| 7 | 5.59 | 89,821 | 0.00 | 0.18 | 66661 |
| 8 | 5.6 | 87,909 | 0.02 | 0.06 | 220 |
| 9 | 6.28 | 87,423 | 0.44 | 0.03 | −93 |
| 10 | 5.48 | 85,649 | 0.00 | 0.05 | 3970 |
| 11 | 5.92 | 83,910 | 0.96 | 0.14 | −85 |
| 12 | 6.97 | 83,902 | 0.01 | 0.15 | 1032 |
| 13 | 6.59 | 83,729 | 0.18 | 0.01 | −97 |
| 14 | 6.7 | 83,729 | 0.02 | 0.61 | 3080 |
| 15 | 5.53 | 79,043 | 5.94 | 0.99 | −83 |
| 16 | 6.06 | 77,562 | 1.91 | 0.48 | −75 |
| 17 | 5.68 | 77,304 | 0.06 | 0.00 | −100 |
| 18 | 5.76 | 76,957 | 0.19 | 0.00 | −99 |
| 19 | 6.31 | 76,697 | 0.02 | 0.02 | −8 |
| 20 | 5.98 | 90,963 | 0.63 | 3.27 | 421 |
| 21 | 6.4 | 74,967 | 0.78 | 7.29 | 840 |
| 22 | 7.19 | 74,742 | 0.10 | 0.05 | −53 |
| 23 | 5.89 | 72,089 | 0.09 | 0.01 | −88 |
| 24 | 5.87 | 70,698 | 0.02 | 0.00 | −94 |
| 25 | 5.7 | 70,177 | 0.19 | 0.01 | −94 |
| 26 | 7.08 | 70,482 | 0.03 | 0.09 | 235 |
| 27 | 5.36 | 68,090 | 0.04 | 0.06 | 57 |
| 28 | 6.21 | 68,220 | 0.09 | 0.00 | −99 |
| 29 | 6.29 | 67,874 | 0.05 | 0.03 | −38 |
| 30 | 6.67 | 67,406 | 0.01 | 0.25 | 2639 |
| 31 | 5.75 | 66,526 | 0.03 | 0.01 | −76 |
| 32 | 7.31 | 68,097 | 0.12 | 0.40 | 239 |
| 33 | 5.52 | 65,483 | 0.12 | 3.41 | 2693 |
| 34 | 6.08 | 65,279 | 2.04 | 0.19 | −91 |
| 35 | 4.99 | 64,885 | 0.45 | 0.41 | −9 |
| 36 | 7.39 | 66,052 | 0.02 | 0.11 | 375 |
| 37 | 7.48 | 64,007 | 0.00 | 0.32 | 14050 |
| 38 | 6.17 | 62,165 | 0.01 | 0.22 | 3946 |
| 39 | 6.22 | 61,473 | 0.02 | 0.12 | 676 |
| 40 | 5.43 | 61,136 | 5.90 | 1.38 | −77 |
| 41 | 5.96 | 61,136 | 3.24 | 2.28 | −30 |
| 42 | 6.3 | 61,127 | 0.27 | 0.46 | 69 |
| 43 | 6.42 | 61,784 | 0.16 | 0.11 | −31 |
| 44 | 6.74 | 62,286 | 0.06 | 0.06 | −8 |
| 45 | 8.44 | 61,726 | 0.02 | 0.79 | 4651 |
| 46 | 5.61 | 59,227 | 0.02 | 0.02 | −12 |
| 47 | 6.48 | 58,874 | 0.52 | 0.22 | −57 |
| 48 | 6.59 | 58,365 | 3.00 | 2.01 | −33 |
| 49 | 5.28 | 57,586 | 0.00 | 0.04 | ++++ |
| 50 | 5.71 | 57,586 | 0.13 | 0.02 | −89 |
| 51 | 5.57 | 56,355 | 0.08 | 0.02 | −73 |
| 52 | 7.48 | 57,859 | 0.07 | 0.02 | −68 |
| 53 | 5.02 | 55,634 | 0.04 | 0.20 | 366 |
| 54 | 8.08 | 57,487 | 0.00 | 0.52 | ++++ |
| 55 | 6.76 | 55,915 | 0.00 | 0.06 | 33872 |
| 56 | 7.63 | 57,152 | 0.08 | 0.15 | 81 |
| 57 | 6.83 | 55,786 | 0.00 | 0.12 | 9161 |
| 58 | 6.9 | 55,658 | 0.05 | 1.59 | 3038 |
| 59 | 5.48 | 54,714 | 0.17 | 0.11 | −38 |
| 60 | 7.1 | 56,317 | 0.01 | 0.10 | 1799 |
| 61 | 7.48 | 56,189 | 0.01 | 0.03 | 412 |
| 62 | 8.28 | 56,540 | 0.02 | 0.30 | 1849 |
| 63 | 5.01 | 53,293 | 0.01 | 0.14 | 2347 |
| 64 | 6.29 | 53,761 | 0.07 | 0.04 | −42 |
| 65 | 7.09 | 54,647 | 0.06 | 0.05 | −28 |
| 66 | 8.54 | 54,366 | 1.44 | 0.39 | −73 |
| 67 | 6.12 | 53,106 | 0.22 | 0.01 | −98 |
| 68 | 6.68 | 53,208 | 0.10 | 0.11 | 11 |
| 69 | 6.26 | 52,582 | 0.11 | 0.01 | −92 |
| 70 | 5.57 | 51,842 | 2.29 | 0.48 | −79 |
| 71 | 6.06 | 51,926 | 0.07 | 0.00 | −100 |
| 72 | 5.71 | 51,295 | 0.60 | 0.12 | −80 |
| 73 | 6.58 | 51,403 | 0.25 | 0.11 | −58 |
| 74 | 6.12 | 50,615 | 0.02 | 0.04 | 160 |
| 75 | 5.05 | 49,049 | 0.31 | 0.02 | −94 |
| 76 | 5.64 | 49,790 | 0.07 | 0.07 | 8 |
| 77 | 7.06 | 51,693 | 0.05 | 0.00 | −92 |
| 78 | 4.97 | 48,610 | 0.13 | 0.06 | −57 |
| 79 | 5.59 | 49,380 | 0.06 | 0.09 | 44 |
| 80 | 8.68 | 50,067 | 0.05 | 0.01 | −82 |
| 81 | 5.35 | 47,876 | 0.09 | 0.01 | −88 |
| 82 | 5.6 | 47,055 | 0.21 | 0.05 | −75 |
| 83 | 5.16 | 45,244 | 0.23 | 0.06 | −74 |
| 84 | 8.79 | 47,487 | 0.15 | 0.40 | 167 |
| 85 | 8.66 | 47,344 | 0.06 | 0.08 | 34 |
| 86 | 5.67 | 45,961 | 0.23 | 0.05 | −81 |
| 87 | 6.67 | 47,149 | 0.00 | 0.85 | 33868 |
| 88 | 6.59 | 47,020 | 0.01 | 0.41 | 6309 |
| 89 | 6.26 | 46,289 | 0.21 | 0.02 | −90 |
| 90 | 5.79 | 45,277 | 0.54 | 0.05 | −91 |
| 91 | 6.47 | 46,027 | 0.09 | 0.14 | 51 |
| 92 | 5.3 | 44,867 | 0.18 | 0.04 | −77 |
| 93 | 8.15 | 46,934 | 0.13 | 0.10 | −26 |
| 94 | 7.39 | 46,426 | 0.00 | 0.07 | 10326 |
| 95 | 5.99 | 44,836 | 0.01 | 0.10 | 2005 |
| 96 | 7.11 | 45,912 | 0.22 | 0.46 | 109 |
| 97 | 5.31 | 42,479 | 0.29 | 0.06 | −80 |
| 98 | 7.48 | 44,885 | 0.01 | 0.11 | 1789 |
| 99 | 8.59 | 46,413 | 0.65 | 3.08 | 377 |
| 100 | 8.74 | 46,413 | 0.81 | 0.28 | −65 |
| 101 | 5.69 | 42,870 | 0.15 | 0.49 | 227 |
| 102 | 8.46 | 44,092 | 0.21 | 1.50 | 617 |
| 103 | 5.91 | 42,296 | 1.30 | 2.59 | 99 |
| 104 | 6.14 | 42,491 | 0.05 | 0.07 | 63 |
| 105 | 5.33 | 41,888 | 1.11 | 0.81 | −27 |
| 106 | 7.39 | 45,972 | 0.02 | 0.08 | 409 |
| 107 | 6.29 | 42,187 | 0.11 | 0.02 | −81 |
| 108 | 7.97 | 42,453 | 1.24 | 0.92 | −26 |
| 109 | 6.19 | 41,629 | 0.05 | 0.00 | −100 |
| 110 | 7.74 | 42,193 | 0.16 | 0.49 | 211 |
| 111 | 7.46 | 41,779 | 0.16 | 0.01 | −94 |
| 112 | 6.28 | 41,122 | 0.03 | 0.31 | 1004 |
| 113 | 7.57 | 41,828 | 0.13 | 0.23 | 80 |
| 114 | 6.13 | 40,666 | 0.21 | 0.02 | −92 |
| 115 | 8.78 | 40,105 | 0.11 | 0.51 | 364 |
| 116 | 7.57 | 40,735 | 0.03 | 0.00 | −96 |
| 117 | 5.39 | 39,543 | 0.10 | 0.01 | −96 |
| 118 | 6.56 | 40,020 | 0.04 | 0.02 | −61 |
| 119 | 5.33 | 39,135 | 0.05 | 0.00 | −100 |
| 120 | 7.49 | 40,094 | 0.17 | 0.13 | −24 |
| 121 | 6.81 | 39,557 | 0.36 | 0.14 | −60 |
| 122 | 7.64 | 39,903 | 0.05 | 0.28 | 439 |
| 123 | 6.42 | 38,992 | 0.15 | 0.00 | −100 |
| 124 | 6.38 | 38,536 | 0.13 | 0.10 | −23 |
| 125 | 7.42 | 38,728 | 0.03 | 0.16 | 528 |
| 126 | 7.17 | 38,056 | 0.09 | 0.14 | 61 |
| 127 | 5.6 | 36,841 | 0.01 | 0.07 | 1279 |
| 128 | 5.13 | 35,384 | 0.00 | 0.11 | ++++ |
| 129 | 5.98 | 36,178 | 0.00 | 0.43 | 45454 |
| 130 | 7.52 | 37,007 | 0.21 | 0.00 | −100 |
| 131 | 5.42 | 35,924 | 0.17 | 0.03 | −85 |
| 132 | 7.71 | 36,520 | 0.02 | 0.33 | 2141 |
| 133 | 5.62 | 35,516 | 0.03 | 0.15 | 473 |
| 134 | 7.18 | 36,349 | 0.09 | 0.23 | 153 |
| 135 | 4.99 | 34,526 | 0.33 | 0.05 | −84 |
| 136 | 5.98 | 35,312 | 0.19 | 0.09 | −50 |
| 137 | 6.39 | 35,645 | 0.03 | 0.66 | 1837 |
| 138 | 6.05 | 35,544 | 0.67 | 0.21 | −69 |
| 139 | 5.73 | 35,006 | 0.03 | 0.01 | −76 |

TABLE 2-continued

Summary of Two-Dimensional Gel Protein Analysis

| | Helper Virus-Free | | | Helper Virus-Containing | |
|---|---|---|---|---|---|
| Spot No. | pI | MW | Spot Percent | Spot Percent | Difference |
| 140 | 5.02 | 33,830 | 0.53 | 0.21 | −60 |
| 141 | 8.04 | 35,162 | 3.36 | 7.90 | 135 |
| 142 | 7.55 | 35,584 | 0.05 | 0.35 | 553 |
| 143 | 6.57 | 34,883 | 0.04 | 0.47 | 1204 |
| 144 | 6 | 34,316 | 0.12 | 0.01 | −92 |
| 145 | 6.06 | 34,479 | 0.03 | 0.14 | 396 |
| 146 | 5.51 | 33,986 | 1.43 | 6.43 | 349 |
| 147 | 5.14 | 32,919 | 0.55 | 1.79 | 225 |
| 148 | 6.23 | 34,225 | 0.32 | 0.18 | −45 |
| 149 | 6.65 | 34,318 | 0.00 | 0.26 | 14364 |
| 150 | 6.54 | 33,855 | 0.06 | 0.08 | 40 |
| 151 | 8.64 | 31,837 | 0.36 | 0.07 | −79 |
| 152 | 6.07 | 32,856 | 0.24 | 0.48 | 96 |
| 153 | 6.27 | 32,856 | 0.01 | 0.18 | 1132 |
| 154 | 8.83 | 31,493 | 0.39 | 0.13 | −68 |
| 155 | 5.14 | 31,043 | 0.00 | 0.14 | ++++ |
| 156 | 5.29 | 31,794 | 0.01 | 0.16 | 2152 |
| 157 | 7.37 | 32,005 | 0.03 | 0.01 | −72 |
| 158 | 6.69 | 31,595 | 0.11 | 0.00 | −100 |
| 159 | 6.08 | 31,233 | 0.04 | 0.33 | 697 |
| 160 | 6.56 | 31,287 | 0.02 | 0.12 | 409 |
| 161 | 4.99 | 30,334 | 0.45 | 0.00 | −99 |
| 162 | 5.72 | 30,214 | 0.01 | 0.17 | 3364 |
| 163 | 5.18 | 30,157 | 0.00 | 0.20 | 6047 |
| 164 | 6.52 | 30,619 | 0.00 | 0.03 | 23471 |
| 165 | 5.63 | 30,329 | 0.05 | 0.38 | 686 |
| 166 | 6.46 | 29,610 | 0.43 | 0.15 | −66 |
| 167 | 6.75 | 29,643 | 0.33 | 0.17 | −49 |
| 168 | 6.28 | 29,186 | 0.22 | 0.85 | 285 |
| 169 | 8.48 | 30,519 | 0.98 | 0.00 | −100 |
| 170 | 6.07 | 28,978 | 1.99 | 0.43 | −78 |
| 171 | 5.33 | 29,767 | 0.08 | 0.15 | 87 |
| 172 | 7.88 | 28,993 | 0.33 | 0.09 | −73 |
| 173 | 6.6 | 28,890 | 0.00 | 0.10 | 6034 |
| 174 | 7.45 | 28,896 | 0.24 | 0.42 | 72 |
| 175 | 6.86 | 28,657 | 0.00 | 0.18 | 197412 |
| 176 | 7.23 | 28,654 | 0.00 | 0.39 | 145023 |
| 177 | 6.98 | 28,210 | 0.05 | 0.01 | −74 |
| 178 | 6.47 | 27,932 | 0.03 | 0.15 | 452 |
| 179 | 6.64 | 27,992 | 0.26 | 0.88 | 247 |
| 180 | 6.24 | 27,822 | 0.05 | 0.02 | −72 |
| 181 | 6.11 | 27,639 | 0.55 | 0.00 | −100 |
| 182 | 6.39 | 27,639 | 0.01 | 0.15 | 2823 |
| 183 | 6.74 | 27,677 | 0.05 | 0.06 | 16 |
| 184 | 7.17 | 27,827 | 0.22 | 0.87 | 295 |
| 185 | 6.45 | 27,347 | 0.02 | 0.55 | 2959 |
| 186 | 7.65 | 27,379 | 0.12 | 0.04 | −68 |
| 187 | 6.29 | 26,871 | 0.22 | 0.09 | −59 |
| 188 | 6.17 | 26,834 | 0.84 | 0.13 | −84 |
| 189 | 5.36 | 26,421 | 0.37 | 0.02 | −95 |
| 190 | 6.61 | 26,767 | 0.34 | 0.21 | −38 |
| 191 | 5 | 25,206 | 2.23 | 0.18 | −92 |
| 192 | 5.69 | 26,122 | 0.08 | 0.90 | 978 |
| 193 | 5.95 | 26,047 | 0.55 | 2.48 | 350 |
| 194 | 6.67 | 26,347 | 0.34 | 0.00 | −100 |
| 195 | 6.57 | 26,312 | 0.13 | 0.00 | −99 |
| 196 | 5.33 | 25,186 | 0.00 | 0.09 | 2843 |
| 197 | 5.13 | 24,166 | 0.06 | 0.00 | −97 |
| 198 | 6.56 | 25,542 | 0.20 | 0.00 | −99 |
| 199 | 5.91 | 24,812 | 0.35 | 0.04 | −88 |
| 200 | 6.2 | 24,931 | 0.32 | 0.03 | −90 |
| 201 | 6.72 | 25,122 | 0.32 | 0.36 | 13 |
| 202 | 5.45 | 24,363 | 0.08 | 0.03 | −63 |
| 203 | 5.29 | 24,326 | 0.14 | 0.21 | 53 |
| 204 | 8.69 | 23,726 | 0.16 | 0.04 | −78 |
| 205 | 9.31 | 22,854 | 0.05 | 0.04 | −28 |
| 206 | 7.81 | 24,487 | 0.30 | 0.49 | 67 |
| 207 | 6.58 | 24,212 | 0.33 | 0.12 | −65 |
| 208 | 6.07 | 23,906 | 0.22 | 0.00 | −100 |
| 209 | 9.06 | 22,562 | 0.12 | 0.04 | −64 |
| 210 | 7.55 | 24,313 | 0.08 | 0.04 | −49 |
| 211 | 6.36 | 23,723 | 5.41 | 0.97 | −82 |
| 212 | 8.45 | 23,160 | 0.10 | 0.03 | −71 |
| 213 | 7.68 | 23,407 | 0.07 | 0.02 | −76 |
| 214 | 6.71 | 23,127 | 0.01 | 0.72 | 5995 |
| 215 | 6.09 | 22,699 | 0.29 | 0.00 | −100 |
| 216 | 5.01 | 20,971 | 0.27 | 0.25 | −5 |
| 217 | 6.66 | 22,567 | 0.10 | 0.08 | −20 |
| 218 | 5.42 | 21,406 | 2.46 | 1.17 | −52 |
| 219 | 6.43 | 21,381 | 0.20 | 0.17 | −16 |
| 220 | 4.61 | 19,596 | 2.30 | 1.27 | −45 |
| 221 | 6.62 | 21,063 | 0.19 | 0.08 | −56 |
| 222 | 7.7 | 21,143 | 0.67 | 0.20 | −71 |
| 223 | 8.81 | 19,769 | 0.23 | 0.05 | −81 |
| 224 | 6.18 | 20,173 | 1.76 | 0.06 | −97 |
| 225 | 7.19 | 20,828 | 0.72 | 0.06 | −92 |
| 226 | 6.78 | 20,503 | 0.01 | 0.10 | 679 |
| 227 | 6.98 | 20,433 | 1.18 | 0.57 | −52 |
| 228 | 5.28 | 19,348 | 0.14 | 0.03 | −81 |
| 229 | 5.31 | 18,787 | 0.10 | 0.05 | −49 |
| 230 | 5.93 | 18,712 | 0.76 | 0.00 | −100 |
| 231 | 5.64 | 18,600 | 0.31 | 0.22 | −28 |
| 232 | 6.67 | 19,523 | 0.14 | 0.11 | −20 |
| 233 | 8.59 | 18,575 | 1.65 | 5.90 | 259 |
| 234 | 5.07 | 17,292 | 2.11 | 0.73 | −66 |
| 235 | 6 | 18,046 | 0.00 | 0.01 | 6403 |
| 236 | 8.95 | 18,029 | 0.11 | 0.05 | −58 |
| 237 | 5.4 | 17,776 | 0.49 | 0.00 | −99 |
| 238 | 5.21 | 17,627 | 0.01 | 0.15 | 1079 |
| 239 | 4.96 | 16,512 | 1.00 | 0.17 | −83 |
| 240 | 8.79 | 17,586 | 0.10 | 0.65 | 562 |
| 241 | 6.55 | 17,843 | 0.05 | 0.01 | −87 |
| 242 | 6.69 | 17,703 | 0.03 | 0.11 | 222 |
| 243 | 6.83 | 17,213 | 0.10 | 0.15 | 59 |
| 244 | 8.68 | 16,051 | 1.61 | 0.01 | −99 |
| 245 | 7.4 | 16,897 | 0.02 | 0.21 | 824 |
| 246 | 6.25 | 15,855 | 0.27 | 0.10 | −64 |
| 247 | 6.23 | 15,342 | 0.25 | 0.71 | 180 |
| 248 | 7.25 | 16,345 | 0.05 | 0.06 | 12 |
| 249 | 6.04 | 15,269 | 0.01 | 0.21 | 2260 |
| 250 | 7.11 | 15,932 | 0.07 | 0.03 | −61 |
| 251 | nd | nd | 0.26 | 1.52 | 496 |
| 252 | 6.69 | 14,760 | 0.22 | 0.51 | 136 |
| 253 | 7.32 | 14,729 | 2.34 | 0.82 | −65 |
| 254 | nd | nd | 0.07 | 0.46 | 598 |
| 255 | nd | nd | 1.39 | 0.03 | −98 | nd = not determined;
++++ = greater than 200,000

Based on the number of differences in the 2D gels for HVF and HVC virion particle polypeptide analyses and the different size and morphology of the HVF virion particles shown in FIG. 13 (as compared to particles produced using helper virus), it is clear the HSV amplicon particles produced according to the present invention are different in kind from the HSV amplicon particles produced using a helper virus in accordance with previously known techniques.

Although the invention has been described in detail for purposes of illustration, it is to be understood that such detail is solely for that purpose, and variations can be made therein by those skilled in the art without departing from the spirit and scope of the invention which is defined by the following claims.

SEQUENCE LISTING

<160> NUMBER OF SEQ ID NOS: 13

<210> SEQ ID NO 1
<211> LENGTH: 4266
<212> TYPE: DNA
<213> ORGANISM: Human herpes simplex virus 1
<220> FEATURE:
<223> OTHER INFORMATION: human herpes

<400> SEQUENCE: 1

| | | | | | |
|---|---|---|---|---|---|
| cgtcgacgac | cacagagaag | gtgcgatggg | tattttcccc | gtacaccgtc | ttggcgttgg | 60 |
| cggccgcctg | gcccgccttg | gtgagcgcgt | tggacaggat | ctggacctgg | gtgctggtgc | 120 |
| tggacgacac | gccctcctcg | cgggcagcaa | aggtgacgca | ggtactcgtg | gtgaacacgg | 180 |
| aaaatttgcc | gttaaccccg | agctcgaacg | tggtgggcgt | ggcactatcg | gccccggtcg | 240 |
| cgttaaggac | cttggtgagc | tgcggcctcg | tcaggcgcaa | ctgaacgtcg | ggggttccct | 300 |
| ggggaaccag | caccacaaag | ctcgtcagtt | cgcgcttcat | cagcgtctcg | ctggctagct | 360 |
| caacggcctc | gccgtcggac | gtcgtcgtcc | atatgcgctg | aaccagcgtg | cgaaacgggg | 420 |
| cctggcccgt | gatcgccaac | tccacccgac | gtaggtccgg | gtactggttg | gcgcgaaaca | 480 |
| cgctcaggag | ggagcgcttc | tggtccacga | gagacaggaa | cgccgccgtg | ggtccgcgcc | 540 |
| agcgataccg | actgaattgc | gagtgttcca | ggggcaggaa | cacctgctcc | ccaaagatcg | 600 |
| tgttatggat | aaggatgccc | cggtcgccca | taaccagaag | cgagtccaga | aggctcgtgc | 660 |
| gcagcgggc | aaacgcctgt | aggattccat | taagttcggc | gccctgcagg | accacctggc | 720 |
| agggcgcccc | ctcctccggc | tgcccgaggg | acgcgtccga | cgcgtcctcc | acggggagg | 780 |
| cgggggccac | accgccaggg | gaatccgtca | tcccaacgcg | ggctgggaac | accccacagt | 840 |
| gacgaggtgg | gcttcggtgg | tgagggcagc | cgggccgggg | tctcgggtgc | gggacgcgga | 900 |
| gggggcgtat | gccgctgcga | gggtgggtt | ttgatggcag | ccaggggacc | caagcaaccg | 960 |
| gaccgtcgct | caccgagcca | gaaactacgg | caggcccgcc | gcgctagcct | gattaaatac | 1020 |
| gccccagct | cgttaggcca | cacccttttg | gaagaggcaa | tgagcggggg | gaaggttggc | 1080 |
| ccgcaccggc | gcatgcaggg | tgctgcacca | atccgcgtgg | agttgggcca | tcgaaattat | 1140 |
| aaagagcgtc | ccctaacgga | ttattgtcct | cttgtgtcgg | tgttgttgtc | tgggtcacca | 1200 |
| tacacagaga | gacaggctcg | ggtgtcccgg | accgtcgcac | caaccacgcc | ttagttaggc | 1260 |
| cgatccgcag | ttacaattga | cctgacatgg | gtttgttcgg | gatgatgaag | tttgcccaca | 1320 |
| cacaccatct | ggtcaagcgc | cggggccttg | gggccccggc | cgggtacttc | accccccattg | 1380 |
| ccgtggacct | gtgaacgtc | atgtacacgt | tggtggtcaa | atatcagcgc | cgataccca | 1440 |
| gttacgaccg | cgaggccatt | acgctacact | gcctctgtcg | cttattaaag | gtgtttaccc | 1500 |
| aaaagtccct | tttccccatc | ttcgttaccg | atcgcgggt | caattgtatg | gagccggttg | 1560 |
| tgtttggagc | caaggccatc | ctggcccgca | cgacggccca | gtgccggacg | gacgaggagg | 1620 |
| ccagtgacgt | ggacgcctct | ccaccgcctt | cccccatcac | cgactccaga | cccagctctg | 1680 |
| cctttttccaa | catgcgccgg | cgcggcacct | ctctggcctc | ggggaccggg | ggacggccg | 1740 |
| ggtccggagc | cgcgctgccg | tccgccgcgc | cctcgaagcc | ggccctgcgt | ctggcgcatc | 1800 |
| tgttctgtat | tcgcgttctc | cgggccctgg | ggtacgccta | cattaactcg | ggtcagctgg | 1860 |
| aggcggacga | tgcctgcgcc | aacctctatc | acaccaacac | ggtcgcgtac | gtgtacacca | 1920 |
| cggacactga | cctcctgttg | atgggctgtg | atattgtgtt | ggatattagc | gcctgctaca | 1980 |

```
ttcccacgat caactgtcgc gatatactaa agtactttaa gatgagctac ccccagttcc   2040
tggccctctt tgtccgctgc cacaccgacc tccatcccaa taacacctac gcctccgtgg   2100
aggatgtgct gcgcgaatgt cactggaccc ccccgagtcg ctctcagacc cggcgggcca   2160
tccgccggga acacaccagc tcgcgctcca cggaaaccag gcccccctctg ccgccggcc   2220 ccggcggcac cgagacgcgc gtctcgtgga ccgaaattct aacccaacag atcgccggcg   2280
gatacgaaga cgacgaggac ctcccccctgg atccccggga cgttaccggg ggccaccccg   2340
gccccaggtc gtcctcctcg gagatactca ccccgcccga gctcgtccag gtcccgaacg   2400
cgcagctgct ggaagagcac cgcagttatg tggccaaccc gcgacgccac gtcatccacg   2460
acgccccaga gtccctggac tggctccccg atcccatgac catcaccgag ctggtggaac   2520
accgctacat taagtacgtc atatcgctta tcggccccaa ggagcggggg ccgtggactc   2580
ttctgaaacg cctgcctatc taccaggaca tccgcgacga aaacctggcg cgatctatcg   2640
tgacccggca tatcacggcc cctgatatcg ccgacaggtt tctggagcag ttgcggaccc   2700
aggccccccc acccgcgttc tacaaggacg tcctggccaa attctgggac gagtagccca   2760
aacgtcagac gagcgcgctt gtccccgaac aaacgaccca ccaataaaat tatggtatcc   2820
tatgcccgca gaatctggac ggacctggtt actgcttttt gcgccgcctt ttatcctctc   2880
ccacccccgc gtccctgaca agaatcacaa tgagacccaa agtttggttc agaggtttat   2940
tatgggcaaa cacgggtaga agcgcgccgc gacactcaca gatcgttgac gaccgccccg   3000
gcgtaggagg tgctgcgaca ctcgaaaaaa ttggtgtgtt tgtcggtgga catgaggctc   3060
agcggaaagc tggcgtcggg gggtgggcg gaaaacagtg gcttcatgtg gataaggccc   3120
aacaggcgat ccgcgctgaa tcgcacgtag ttttcgatgg ccgccagcgc cgccgggctc   3180
aggatatggc tgtccgtcgg cgcctgggat cggataaatc cgatctcgat ctcgaccgcc   3240
tggcggaaca gcccgtacac gcggtcgggc ggggcttgg cgtgcccgcc gaggtagttg   3300
ttgtagatgt aacacgaggc cgtcgtgtgc acggcctcgt cccggctgat gaggtcgttt   3360
gactggcagg tgacccgcag aaggttgttg gtgcgaaggt aggcgatggc ggcaaacgag   3420
gcggcaaaaa agatgccctc gatgaggatc atgagaatga acttttccgg aacggaggcg   3480
cattcccgca cccgcgcttc caaccagtcc accttggcgc ggatggccgg gtggttgatg   3540
gtaccggcca cgtactcgcg gcgcgcctgg tcgttgttgt ggaaaagcac cagctggatg   3600
atgttgtaca cgcgcgagtg tacgacttcg atgcattcct gctccacgta gtagtggaga   3660
atgtccttct gctcaaacag gccggagagg ccgcccaggt tttccgtaac caggtcgtcg   3720
gcggccgaca ggaaagcgaa gaggaagcgg taaaagctga gctcgccctc ggaaagcttg   3780
gagacgtcct cctcgtcccc cacgaaaaca agctcggttt ccagccagcg gttaaggatg   3840
ctgagggagc gcaggtggtt aatgtcggga cactgggagg tgtagaagta cctctcgggg   3900
tcggggcact ttggaatctg gatcgccagg tccgccgtcg cgctctggtc cgtaagggcc   3960
gtcagagcgg gggagagggc tggggccgcg gaatccatgg cagcagggga gagcgtggga   4020
cggcgacgac agtggcggcg ggcctggcgc ggaggggggtt tgtcggtcac agcgcgcagc   4080
tcatgcagac aatgttgtcg tcgccgccaa agaccccgct gttggtcgcc ttgcgaacct   4140
tgcagtagta catccctgtt tttagtccgc gcttatatgc gtggaccaga aggcggacca   4200
gggtggaggc tgggagggtc ccgtccgcct tctccgtgac atacagggtc atggattggc   4260
tatggt                                                            4266
```

<210> SEQ ID NO 2

<211> LENGTH: 489
<212> TYPE: PRT
<213> ORGANISM: Human herpes simplex virus 1

<400> SEQUENCE: 2

```
Met Gly Leu Phe Gly Met Met Lys Phe Ala His Thr His His Leu Val
 1               5                  10                  15

Lys Arg Arg Gly Leu Gly Ala Pro Ala Gly Tyr Phe Thr Pro Ile Ala
            20                  25                  30

Val Asp Leu Trp Asn Val Met Tyr Thr Leu Val Val Lys Tyr Gln Arg
        35                  40                  45

Arg Tyr Pro Ser Tyr Asp Arg Glu Ala Ile Thr Leu His Cys Leu Cys
50                  55                  60

Arg Leu Leu Lys Val Phe Thr Gln Lys Ser Leu Phe Pro Ile Phe Val
65                  70                  75                  80

Thr Asp Arg Gly Val Asn Cys Met Glu Pro Val Val Phe Gly Ala Lys
                85                  90                  95

Ala Ile Leu Ala Arg Thr Thr Ala Gln Cys Arg Thr Asp Glu Glu Ala
            100                 105                 110

Ser Asp Val Asp Ala Ser Pro Pro Ser Pro Ile Thr Asp Ser Arg
        115                 120                 125

Pro Ser Ser Ala Phe Ser Asn Met Arg Arg Gly Thr Ser Leu Ala
    130                 135                 140

Ser Gly Thr Arg Gly Thr Ala Gly Ser Gly Ala Ala Leu Pro Ser Ala
145                 150                 155                 160

Ala Pro Ser Lys Pro Ala Leu Arg Leu Ala His Leu Phe Cys Ile Arg
                165                 170                 175

Val Leu Arg Ala Leu Gly Tyr Ala Tyr Ile Asn Ser Gly Gln Leu Glu
            180                 185                 190

Ala Asp Asp Ala Cys Ala Asn Leu Tyr His Thr Asn Thr Val Ala Tyr
        195                 200                 205

Val Tyr Thr Thr Asp Thr Asp Leu Leu Leu Met Gly Cys Asp Ile Val
    210                 215                 220

Leu Asp Ile Ser Ala Cys Tyr Ile Pro Thr Ile Asn Cys Arg Asp Ile
225                 230                 235                 240

Leu Lys Tyr Phe Lys Met Ser Tyr Pro Gln Phe Leu Ala Leu Phe Val
                245                 250                 255

Arg Cys His Thr Asp Leu His Pro Asn Asn Thr Tyr Ala Ser Val Glu
            260                 265                 270

Asp Val Leu Arg Glu Cys His Trp Thr Pro Ser Arg Ser Gln Thr
        275                 280                 285

Arg Arg Ala Ile Arg Arg Glu His Thr Ser Ser Arg Ser Thr Glu Thr
    290                 295                 300

Arg Pro Pro Leu Pro Pro Ala Ala Gly Gly Thr Glu Thr Arg Val Ser
305                 310                 315                 320

Trp Thr Glu Ile Leu Thr Gln Gln Ile Ala Gly Gly Tyr Glu Asp Asp
                325                 330                 335

Glu Asp Leu Pro Leu Asp Pro Arg Asp Val Thr Gly Gly His Pro Gly
            340                 345                 350

Pro Arg Ser Ser Ser Ser Glu Ile Leu Thr Pro Pro Glu Leu Val Gln
        355                 360                 365

Val Pro Asn Ala Gln Leu Leu Glu Glu His Arg Ser Tyr Val Ala Asn
    370                 375                 380

Pro Arg Arg His Val Ile His Asp Ala Pro Glu Ser Leu Asp Trp Leu
385                 390                 395                 400
```

```
Pro Asp Pro Met Thr Ile Thr Glu Leu Val Glu His Arg Tyr Ile Lys
            405                 410                 415

Tyr Val Ile Ser Leu Ile Gly Pro Lys Glu Arg Gly Pro Trp Thr Leu
            420                 425                 430

Leu Lys Arg Leu Pro Ile Tyr Gln Asp Ile Arg Asp Glu Asn Leu Ala
            435                 440                 445

Arg Ser Ile Val Thr Arg His Ile Thr Ala Pro Asp Ile Ala Asp Arg
    450                 455                 460

Phe Leu Glu Gln Leu Arg Thr Gln Ala Pro Pro Ala Phe Tyr Lys
465                 470                 475                 480

Asp Val Leu Ala Lys Phe Trp Asp Glu
            485

<210> SEQ ID NO 3
<211> LENGTH: 1469
<212> TYPE: DNA
<213> ORGANISM: Human herpes simplex virus 1

<400> SEQUENCE: 3
atgggtttgt cgggatgat  gaagtttgcc cacacacacc atctggtcaa gcgccggggc      60
cttggggccc cggccgggta cttcaccccc attgccgtgg acctgtggaa cgtcatgtac     120
acgttggtgg tcaaatatca gcgccgatac cccagttacg accgcgaggc cattacgcta     180
cactgcctct gtcgcttatt aaaggtgttt acccaaaagt ccctttttcc catcttcgtt     240
accgatcgcg gggtcaattg tatggagccg gttgtgtttg gagccaaggc catcctggcc     300
cgcacgacgg cccagtgccg gacggacgag gaggccagtg acgtggacgc ctctccaccg     360
ccttccccca tcaccgactc cagacccagc tctgcctttt ccaacatgcg ccggcgcggc     420
acctctctgg cctcggggac ccggggggacg gccgggtccg gagccgcgct gccgtccgcc     480
gcgccctcga agccggccct gcgtctggcg catctgttct gtattcgcgt ctccgggcc      540 ctggggtacg cctacattaa ctcgggtcag ctggaggcgg acgatgcctg cgccaacctc     600
tatcacacca cacggtcgc gtacgtgtac accacggaca ctgacctcct gttgatgggc      660
tgtgatattg tgttggatat tagcgcctgc tacattccca cgatcaactg tcgcgatata     720
ctaaagtact ttaagatgag ctaccccag ttcctggcct cttcgtccgc tgccacaccg       780
acctccatcc caataacacc tacgcctccg tggaggatgt gctgcgcgaa tgtcactgga     840 ccccccgag tcgctctcag acccggcggg ccatccgccg gaacacacc agctcgcgct       900 ccacggaaac caggcccccct ctgccgccgg ccgccggcgg caccgagacg cgcgtctcgt    960
ggaccgaaat tctaacccaa cagatcgccg gcggatacga agacgacgag gacctccccc    1020 tggatcccccg ggacgttacc gggggccacc ccggcccccag gtcgtcctcc tcggagatac    1080 tcacccccgcc cgagctcgtc caggtcccga acgcgcagct gctggaagag caccgcagtt    1140
atgtggccaa cccgcgacgc cacgtcatcc acgacgcccc agagtccctg gactggctcc    1200
ccgatcccat gaccatcacc gagctggtgg aacaccgcta cattaagtac gtcatatcgc    1260
ttatcggccc caaggagcgg gggccgtgga ctcttctgaa acgcctgcct atctaccagg    1320
acatccgcga cgaaaacctg gcgcgatcta tcgtgacccg gcatatcacg gcccctgata    1380
tcgccgacag gtttctggag cagttgcgga cccaggcccc cccacccgcg ttctacaagg    1440
acgtcctggc caaattctgg gacgagtag                                       1469

<210> SEQ ID NO 4
<211> LENGTH: 490
```

```
<212> TYPE: PRT
<213> ORGANISM: Human herpes simplex virus 1

<400> SEQUENCE: 4
```

| | | | | | | | | | | | | | | |
|---|---|---|---|---|---|---|---|---|---|---|---|---|---|---|
| Met | Asp | Leu | Leu | Val | Asp | Glu | Leu | Phe | Ala | Asp | Met | Asn | Ala | Asp | Gly |
| 1 | | | | 5 | | | | | 10 | | | | | 15 | |

| Ala | Ser | Pro | Pro | Pro | Arg | Pro | Ala | Gly | Gly | Pro | Lys | Asn | Thr | Pro |
|---|---|---|---|---|---|---|---|---|---|---|---|---|---|---|
| | | | 20 | | | | 25 | | | | 30 | | | |

| Ala | Ala | Pro | Pro | Leu | Tyr | Ala | Thr | Gly | Arg | Leu | Ser | Gln | Ala | Gln | Leu |
|---|---|---|---|---|---|---|---|---|---|---|---|---|---|---|---|
| | | 35 | | | | | 40 | | | | | 45 | | | |

| Met | Pro | Ser | Pro | Pro | Met | Pro | Val | Pro | Pro | Ala | Ala | Leu | Phe | Asn | Arg |
|---|---|---|---|---|---|---|---|---|---|---|---|---|---|---|---|
| | 50 | | | | | 55 | | | | | 60 | | | | |

| Leu | Leu | Asp | Asp | Leu | Gly | Phe | Ser | Ala | Gly | Pro | Ala | Leu | Cys | Thr | Met |
|---|---|---|---|---|---|---|---|---|---|---|---|---|---|---|---|
| 65 | | | | | 70 | | | | | 75 | | | | | 80 |

| Leu | Asp | Thr | Trp | Asn | Glu | Asp | Leu | Phe | Ser | Ala | Leu | Pro | Thr | Asn | Ala |
|---|---|---|---|---|---|---|---|---|---|---|---|---|---|---|---|
| | | | | 85 | | | | | 90 | | | | | 95 | |

| Asp | Leu | Tyr | Arg | Glu | Cys | Lys | Phe | Leu | Ser | Thr | Leu | Pro | Ser | Asp | Val |
|---|---|---|---|---|---|---|---|---|---|---|---|---|---|---|---|
| | | | 100 | | | | | 105 | | | | | 110 | | |

| Val | Glu | Trp | Gly | Asp | Ala | Tyr | Val | Pro | Glu | Arg | Thr | Gln | Ile | Asp | Ile |
|---|---|---|---|---|---|---|---|---|---|---|---|---|---|---|---|
| | | 115 | | | | | 120 | | | | | 125 | | | |

| Arg | Ala | His | Gly | Asp | Val | Ala | Phe | Pro | Thr | Leu | Pro | Ala | Thr | Arg | Asp |
|---|---|---|---|---|---|---|---|---|---|---|---|---|---|---|---|
| | 130 | | | | | 135 | | | | | 140 | | | | |

| Gly | Leu | Gly | Leu | Tyr | Tyr | Glu | Ala | Leu | Ser | Arg | Phe | Phe | His | Ala | Glu |
|---|---|---|---|---|---|---|---|---|---|---|---|---|---|---|---|
| 145 | | | | | 150 | | | | | 155 | | | | | 160 |

| Leu | Arg | Ala | Arg | Glu | Glu | Ser | Tyr | Arg | Thr | Val | Leu | Ala | Asn | Phe | Cys |
|---|---|---|---|---|---|---|---|---|---|---|---|---|---|---|---|
| | | | | 165 | | | | | 170 | | | | | 175 | |

| Ser | Ala | Leu | Tyr | Arg | Tyr | Leu | Arg | Ala | Ser | Val | Arg | Gln | Leu | His | Arg |
|---|---|---|---|---|---|---|---|---|---|---|---|---|---|---|---|
| | | | 180 | | | | | 185 | | | | | 190 | | |

| Gln | Ala | His | Met | Arg | Gly | Arg | Asp | Arg | Asp | Leu | Gly | Glu | Met | Leu | Arg |
|---|---|---|---|---|---|---|---|---|---|---|---|---|---|---|---|
| | | 195 | | | | | 200 | | | | | 205 | | | |

| Ala | Thr | Ile | Ala | Asp | Arg | Tyr | Tyr | Arg | Glu | Thr | Ala | Arg | Leu | Ala | Arg |
|---|---|---|---|---|---|---|---|---|---|---|---|---|---|---|---|
| | 210 | | | | | 215 | | | | | 220 | | | | |

| Val | Leu | Phe | Leu | His | Leu | Tyr | Leu | Phe | Leu | Thr | Arg | Glu | Ile | Leu | Trp |
|---|---|---|---|---|---|---|---|---|---|---|---|---|---|---|---|
| 225 | | | | | 230 | | | | | 235 | | | | | 240 |

| Ala | Ala | Tyr | Ala | Glu | Gln | Met | Met | Arg | Pro | Asp | Leu | Phe | Asp | Cys | Leu |
|---|---|---|---|---|---|---|---|---|---|---|---|---|---|---|---|
| | | | | 245 | | | | | 250 | | | | | 255 | |

| Cys | Cys | Asp | Leu | Glu | Ser | Trp | Arg | Gln | Leu | Ala | Gly | Leu | Phe | Gln | Pro |
|---|---|---|---|---|---|---|---|---|---|---|---|---|---|---|---|
| | | | 260 | | | | | 265 | | | | | 270 | | |

| Phe | Met | Phe | Val | Asn | Gly | Ala | Leu | Thr | Val | Arg | Gly | Val | Pro | Ile | Glu |
|---|---|---|---|---|---|---|---|---|---|---|---|---|---|---|---|
| | | 275 | | | | | 280 | | | | | 285 | | | |

| Ala | Arg | Arg | Leu | Arg | Glu | Leu | Asn | His | Ile | Arg | Glu | His | Leu | Asn | Leu |
|---|---|---|---|---|---|---|---|---|---|---|---|---|---|---|---|
| | 290 | | | | | 295 | | | | | 300 | | | | |

| Pro | Leu | Val | Arg | Ser | Ala | Ala | Thr | Glu | Glu | Pro | Gly | Ala | Pro | Leu | Thr |
|---|---|---|---|---|---|---|---|---|---|---|---|---|---|---|---|
| 305 | | | | | 310 | | | | | 315 | | | | | 320 |

| Thr | Pro | Pro | Thr | Leu | His | Gly | Asn | Gln | Ala | Arg | Ala | Ser | Gly | Tyr | Phe |
|---|---|---|---|---|---|---|---|---|---|---|---|---|---|---|---|
| | | | | 325 | | | | | 330 | | | | | 335 | |

| Met | Val | Leu | Ile | Arg | Ala | Lys | Leu | Asp | Ser | Tyr | Ser | Ser | Phe | Thr | Thr |
|---|---|---|---|---|---|---|---|---|---|---|---|---|---|---|---|
| | | | 340 | | | | | 345 | | | | | 350 | | |

| Ser | Pro | Ser | Glu | Ala | Val | Met | Arg | Glu | His | Ala | Tyr | Ser | Arg | Ala | Arg |
|---|---|---|---|---|---|---|---|---|---|---|---|---|---|---|---|
| | | 355 | | | | | 360 | | | | | 365 | | | |

| Thr | Lys | Asn | Asn | Tyr | Gly | Ser | Thr | Ile | Glu | Gly | Leu | Leu | Asp | Leu | Pro |
|---|---|---|---|---|---|---|---|---|---|---|---|---|---|---|---|
| | 370 | | | | | 375 | | | | | 380 | | | | |

| Asp | Asp | Asp | Ala | Pro | Glu | Glu | Ala | Gly | Leu | Ala | Ala | Pro | Arg | Leu | Ser |
|---|---|---|---|---|---|---|---|---|---|---|---|---|---|---|---|
| 385 | | | | | 390 | | | | | 395 | | | | | 400 |

```
Phe Leu Pro Ala Gly His Thr Arg Arg Leu Ser Thr Ala Pro Pro Thr
                405                 410                 415

Asp Val Ser Leu Gly Asp Glu Leu His Leu Asp Gly Glu Asp Val Ala
            420                 425                 430

Met Ala His Ala Asp Ala Leu Asp Asp Phe Asp Leu Asp Met Leu Gly
        435                 440                 445

Asp Gly Asp Ser Pro Gly Pro Gly Phe Thr Pro His Asp Ser Ala Pro
    450                 455                 460

Tyr Gly Ala Leu Asp Met Ala Asp Phe Glu Phe Glu Gln Met Phe Thr
465                 470                 475                 480

Asp Ala Leu Gly Ile Asp Glu Tyr Gly Gly
                485                 490

<210> SEQ ID NO 5
<211> LENGTH: 1473
<212> TYPE: DNA
<213> ORGANISM: Human herpes simplex virus 1

<400> SEQUENCE: 5
atggacctct tggtcgacga gctgtttgcc gacatgaacg cggacggcgc ttcgccaccg      60 ccccccgcc cggccggggg tcccaaaaac accccggcgg ccccccgct gtacgcaacg      120 gggcgcctga ccaggcccca gctcatgccc tccccacca tgcccgtccc cccgccgcc      180 ctctttaacc gtctcctcga cgacttgggc tttagcgcgg gccccgcgct atgtaccatg    240
ctcgatacct ggaacgagga tctgttttcg gcgctaccga ccaacgccga cctgtaccgg    300
gagtgtaaat tcctatcaac gctgcccagc gatgtggtgg aatgggggga cgcgtacgtc    360
cccgaacgca cccaaatcga cattcgcgcc cacggcgacg tggccttccc tacgcttccg    420
gccacccgcg acggcctcgg gctctactac gaagcgctct ctcgtttctt ccacgccgag    480
ctacgggcgc gggaggagag ctatcgaacc gtgttggcca acttctgctc ggccctgtac    540
cggtacctgc gcgccagcgt ccggcagctg caccgccagg cgcacatgcg cggacgcgat    600
cgcgacctgg gagaaatgct gcgcgccacg atcgcggaca ggtactaccg agagaccgct    660
cgtctggcgc gtgttttgtt tttgcatttg tatctatttt tgacccgcga gatcctatgg    720
gccgcgtacg ccgagcagat gatgcggccc gacctgtttg actgcctctg ttgcgacctg    780
gagagctggc gtcagttggc gggtctgttc cagcccttca tgttcgtcaa cggagcgctc    840
accgtccggg gagtgccaat cgaggcccgc cggctgcggg agctaaacca cattcgcgag    900
caccttaacc tcccgctggt gcgcagcgcg gctacgaggg agccagggg gccgttgacg    960 accccctccca ccctgcatgg caaccaggcc cgcgcctctg gtactttat ggtgttgatt   1020 cgggcgaagt tggactcgta ttccagcttc acgacctcgc cctccgaggc ggtcatgcgg   1080
gaacacgcgt acagccgcgc gcgtacgaaa aacaattacg ggtctaccat cgagggcctg   1140
ctcgatctcc ggacgacga cgcccccgaa gaggcgggc tggcggctcc gcgcctgtcc   1200
tttctccccg cgggacacac gcgcagactg tcgacggccc cccgaccga tgtcagcctg   1260 ggggacgagc tccacttaga cggcgaggac gtggcgatgg cgcatgccga cgcgctagac   1320
gatttcgatc tggacatgtt gggggacggg gattccccgg ggccgggatt tacccccac   1380 gactccgccc cctacggcgc tctggatatg gccgacttcg agtttgagca gatgtttacc   1440
gatgcccttg gaattgacga gtacggtggg tag                                1473

<210> SEQ ID NO 6
<211> LENGTH: 35
<212> TYPE: DNA
```

```
<213> ORGANISM: Artificial Sequence
<220> FEATURE:
<223> OTHER INFORMATION: primer

<400> SEQUENCE: 6
cggaattccg caggttttgt aatgtatgtg ctcgt                              35

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
ctccgaagct taagcccgat atcgtctttc ccgtatca                           38

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
accccgtacg tcttcccgag cg                                            22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gggatctgcc attgtcagac at                                            22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tggtgtgggc cataattcaa                                               20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tgctggcacc agacttgccc tc                                            22

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cggctaccac atccaaggaa                                               20
```

```
<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
gctggaatta ccgcggct                                                 18
```

What is claimed is:

1. A method for producing herpes simplex virus (HSV) amplicon particles, comprising:
   co-transfecting a host cell with the following:
   (i) an amplicon vector comprising an HSV origin of replication, an HSV cleavage/packaging signal, and a heterologous transgene expressible in a patient,
   (ii) one or more vectors individually or collectively encoding all essential HSV genes but excluding all cleavage/packaging signals, and
   (iii) a vhs expression vector encoding a virion host shut-off protein; and
   isolating HSV amplicon particles produced by the host cell, the HSV amplicon particles including the transgene.

2. The method according to claim 1, wherein the isolated HSV amplicon particles are substantially pure.

3. The method according to claim 1, wherein the virion host shutoff protein is selected from the group consisting of HSV-1 virion host shutoff protein, HSV-2 virion host shutoff protein, HSV-3 virion host shutoff protein, bovine herpesvirus 1 virion host shutoff protein, bovine herpesvirus 1.1 virion host shutoff protein, gallid herpesvirus 1 virion host shutoff protein, gallid herpesvirus 2 virion host shutoff protein, suid herpesvirus 1 virion host shutoff protein, baboon herpesvirus 2 virion host shutoff protein, pseudorabies virus virion host shutoff protein, cercopithecine herpesvirus 7 virion host shutoff protein, meleagrid herpesvirus 1 virion host shutoff protein, equine herpesvirus 1 virion host shutoff protein, and equine herpesvirus 4 virion host shutoff protein.

4. The method according to claim 3, wherein the virion host shutoff protein is selected from the group consisting of HSV-1 virion host shutoff protein, HSV-2 virion host shutoff protein, and HSV-3 virion host shutoff protein.

5. The method according to claim 4, wherein the vhs expression vector comprises:
   a DNA molecule encoding the HSV virion host shutoff protein operatively coupled to its native transcriptional control elements.

6. The method according to claim 1, wherein the vhs expression vector comprises:
   a DNA molecule encoding the virion host shutoff protein;
   a promoter element operatively coupled 5' to the DNA molecule; and
   a transcription termination element operatively coupled 3' to the DNA molecule.

7. The method according to claim 1, wherein the host cell expresses a VP16 protein.

8. The method according to claim 7, wherein the VP16 protein is selected from the group consisting of HSV-1 VP16, HSV-2 VP16, bovine herpesvirus 1 VP16, bovine herpesvirus 1.1 VP16, gallid herpesvirus 1 VP16, gallid herpesvirus 2 VP16, meleagrid herpesvirus 1 VP16, and equine herpesvirus 4 VP16.

9. The method according to claim 7 further comprising:
   transfecting the host cell, prior to said co-transfecting, with a vector encoding the VP16 protein.

10. The method according to claim 9, wherein said transfecting is carried out at least about 4 hours prior to said co-transfecting.

11. The method according to claim 7, wherein the host cell stably expresses the VP16 protein.

12. The method according to claim 1, wherein the isolated HSV amplicon particles are present at a concentration of greater than $1 \times 10^6$ particles per milliliter.

13. The method according to claim 1 further comprising:
   concentrating the isolated HSV amplicon particles to a concentration of at least about $1 \times 10^7$ particles per milliliter.

14. The method according to claim 1 wherein the transgene encodes a therapeutic transgene product.

15. The method according to claim 14, wherein the therapeutic transgene product is a protein or an RNA molecule.

16. The method according to claim 15, wherein the therapeutic transgene product is an RNA molecule selected from the group consisting of antisense RNA, an inhibitory RNA, and an RNA ribozyme.

17. The method according to claim 15, wherein the therapeutic transgene product is a protein selected from the group consisting of receptors, signaling molecules, transcription factors, growth factors, apoptosis inhibitors, apoptosis promoters, DNA replication factors, enzymes, structural proteins, neural proteins, and histone or non-histone proteins.

18. An HSV amplicon particle produced according to the process of claim 1.

19. An HSV amplicon particle produced according to the process of claim 14.

20. A kit for preparing HSV amplicon particles comprising:
   an amplicon vector comprising an HSV origin of replication, an HSV cleavage/packaging signal, and a transgene insertion site;
   one or more vectors individually or collectively encoding all essential HSV genes but excluding all cleavage/packaging signals;
   a vhs expression vector encoding an virion host shutoff protein;
   a population of host cells susceptible to transfection by the amplicon vector, the vhs expression vector, and the one or more vectors; and
   directions for transfecting the host cells under conditions to produce HSV amplicon particles.

21. The kit according to claim 20 further comprising:
   a vector encoding a VP16 protein.

22. The kit according to claim 21, wherein the VP16 protein is selected from the group consisting of HSV-1 VP16, HSV-2 VP16, bovine herpesvirus 1 VP16, bovine herpesvirus 1.1 VP16, gallid herpesvirus 1 VP16, gallid herpesvirus 2 VP16, meleagrid herpesvirus 1 VP16, and equine herpesvirus 4 VP16.

23. The kit according to claim 20, wherein the host cell stably expresses a VP 16 protein.

24. The kit according to claim 23, wherein the VP16 protein is selected from the group consisting of HSV-1 VP16, HSV-2 VP16, bovine herpesvirus 1 VP16, bovine herpesvirus 1.1 VP16, gallid herpesvirus 1 VP16, gallid herpesvirus 2 VP16, meleagrid herpesvirus 1 VP16, and equine herpesvirus 4 VP16.

25. The kit according to claim 20, wherein the virion host shutoff protein is selected from the group consisting of HSV-1 virion host shutoff protein, HSV-2 virion host shutoff protein, HSV-3 virion host shutoff protein, bovine herpesvirus 1 virion host shutoff protein, bovine herpesvirus 1.1 virion host shutoff protein, gallid herpesvirus 1 virion host shutoff protein, gallid herpesvirus 2 virion host shutoff protein, suid herpesvirus 1 virion host shutoff protein, baboon herpesvirus 2 virion host shutoff protein, pseudorabies virus virion host shutoff protein, cercopithecine herpesvinis 7 virion host shutoff protein, meleagrid herpesvirus 1 virion host shutoff protein, equine herpesvirus 1 virion host shutoff protein, and equine herpesvirus 4 virion host shutoff protein.

26. The kit according to claim 25, wherein the virion host shutoff protein is selected from the group consisting of HSV-1 virion host shutoff protein, HSV-2 virion host shutoff protein, and HSV-3 virion host shutoff protein.

27. The kit according to claim 26, wherein the vhs expression vector comprises: a DNA molecule encoding the HSV virion host shutoff protein operatively coupled to its native transcriptional control elements.

28. The kit according to claim 20, wherein the vhs expression vector comprises:
 a DNA molecule encoding the virion host shutoff protein;
 a promoter element operatively coupled 5' to the DNA molecule; and
 a transcription termination element operatively coupled 3' to the DNA molecule.

\* \* \* \* \*

UNITED STATES PATENT AND TRADEMARK OFFICE
CERTIFICATE OF CORRECTION

PATENT NO. : 8,092,791 B2  
APPLICATION NO. : 10/296551  
DATED : January 10, 2012  
INVENTOR(S) : Howard J. Federoff and William J. Bowers It is certified that error appears in the above-identified patent and that said Letters Patent is hereby corrected as shown below:

Column 54, line 45, "process of claim 1" should read  
--method of claim 1--

Column 54, line 47, "process of claim 14" should read  
--method of claim 14--

Column 56, line 1, "cercopithecine herpesvinis 7" should read  
--cercopithecine herpesvirus 7--

Signed and Sealed this  
Twenty-fifth Day of September, 2012

David J. Kappos  
*Director of the United States Patent and Trademark Office*